United States Patent [19]

Lewis et al.

[11] Patent Number: 4,973,725
[45] Date of Patent: Nov. 27, 1990

[54] DIRECT SYNTHESIS PROCESS FOR ORGANOHALOHYDROSILANES

[75] Inventors: Kenrick M. Lewis, Queens; Rudolph A. Cameron, Bronx, both of N.Y.; Jeffrey M. Larnerd, Dunbar, W. Va.; Bernard Kanner, West Nyack, N.Y.

[73] Assignee: Union Carbide Chemicals and Plastics Company Inc., Danbury, Conn.

[21] Appl. No.: 364,031

[22] Filed: Jun. 13, 1989

Related U.S. Application Data

[63] Continuation-in-part of Ser. No. 213,299, Jun. 28, 1988, abandoned.

[51] Int. Cl.$^5$ .............................................. C07F 7/16
[52] U.S. Cl. .............................. 556/472; 252/182.33; 252/186.24
[58] Field of Search ............ 556/472; 252/182, 186.24

[56] References Cited

U.S. PATENT DOCUMENTS

| | | | |
|---|---|---|---|
| 2,380,995 | 8/1945 | Rochow et al. | 556/472 |
| 2,380,996 | 8/1945 | Rochow et al. | 260/607 |
| 2,380,997 | 8/1945 | Patnode | 252/225 |
| 2,380,998 | 8/1945 | Sprung et al. | 260/607 |
| 2,595,620 | 5/1952 | Wagner et al. | 23/14 |
| 2,598,435 | 5/1952 | Mohler et al. | 260/448.2 |
| 2,681,355 | 6/1954 | Barry et al. | 260/448.2 |
| 2,709,176 | 5/1955 | Bluestein | 260/448.2 |
| 2,842,580 | 7/1958 | Gilbert et al. | 260/448.2 |
| 3,445,200 | 5/1969 | Dunogues et al. | 23/366 |
| 3,639,105 | 2/1972 | Atwell et al. | 23/366 |
| 3,704,260 | 11/1972 | Wynn | 260/448.2 |
| 3,704,261 | 11/1972 | Berger et al. | 260/448.2 |
| 4,059,608 | 11/1977 | Calas et al. | 260/448.2 |
| 4,079,071 | 3/1978 | Neale | 260/448.2 |
| 4,088,669 | 5/1978 | Malek et al. | 556/472 |
| 4,115,426 | 9/1978 | Hillros et al. | 260/448.2 |
| 4,181,673 | 1/1980 | Schumann et al. | 260/448.2 |
| 4,314,908 | 2/1982 | Downing et al. | 252/182 |
| 4,450,282 | 5/1984 | Ritzer et al. | 556/472 |
| 4,487,949 | 12/1984 | Mallon | 556/472 |
| 4,500,724 | 2/1985 | Ward et al. | 556/472 |
| 4,645,851 | 2/1987 | Prud' Homme | 556/472 |
| 4,656,301 | 4/1987 | Prud' Homme et al. | 556/472 |
| 4,661,613 | 4/1987 | Prud' Homme et al. | 556/472 |
| 4,684,741 | 8/1987 | Prud' Homme | 556/472 |
| 4,762,940 | 8/1988 | Halm et al. | 556/472 |

FOREIGN PATENT DOCUMENTS

| | | |
|---|---|---|
| 859164 | 12/1952 | Fed. Rep. of Germany. |
| 1523912 | 3/1968 | France. |
| 57-47917 | 10/1982 | Japan. |
| 590654 | 7/1947 | United Kingdom. |
| 575674 | 6/1948 | United Kingdom. |

OTHER PUBLICATIONS

Voorhoeve, "Organohalosilanes" Elsevier, N.Y., 1967, 190–201.
Turetskaya et al., "Direct Synthesis of Ethylchlorosilanes", Khim. Prom., 18–20 (1963) (English Abstract).
Calas et al., "Some Practical Uses of Disilane—etc.", J. Organomet. Chem., 225, 117–130 (1982).
Chalk, "The Use of Sodium Hydride—etc.", J. Organomet. Chem. 21, 95–101 (1970).
Antipin et al., "Selective Reduction of Organochlorosilanes", Russ. J. Gen. Chem., 40, 789–791 (1970).
Simon et al., "Nouvelles Syntheses de—etc.", J. Organomet. Chem., 206, 279–286 (1981).
Eaborn et al., "Organosilicon Compounds", J. Organomet. Chem. 18, 371–372 (1969).
Gorbunov et al., "Mechanism of Formation of—etc.", Trans. from Dokl. Akad. Nauk, SSSR, 194, 92–94 (1970).
Gorbunov et al., "Reactions of Silicon and Germanium—etc.", Russ. Chem. Rev., 43, 291–304 (1974).
DeCooker et al., "The Direct Synthesis of—etc.", J. Organomet. Chem., 99, 371–377 (1975).
DeCooker, "Kinetics & Mechanism of—etc." Ph.D. Diss. Univ. Delft, 57–73 (1976).
Lobusevich et al., "Phase Transformations of—etc.", Russ. Jour. Appl. Chem. 49, 2168–2174 (1976).
Lobusevich et al., "Transformations in the Direct Synthesis of Alkylchlorosilanes", Series of 4 papers; Russ. J. Gen. Chem. 48, 2055–2060, 2290–2294, 2295–2301, 2302–2307 (1978).

*Primary Examiner*—Paul F. Shaver
*Attorney, Agent, or Firm*—Bonnie L. Deppenbrock

[57] ABSTRACT

Direct Synthesis processes for the selective production of organohalohydrosilanes at high rates, selectivities and conversions by the catalytic reaction of activated silicon with mixtures of organohalides and hydrogen in the presence of controlled concentrations of selected metal atoms.

30 Claims, No Drawings

4,973,725

DIRECT SYNTHESIS PROCESS FOR ORGANOHALOHYDROSILANES

This application is a continuation-in-part of U.S. Ser. No. 07/213,299, filed 6/28/88, now abandoned.

FIELD OF THE INVENTION

This invention relates to a Direct Synthesis process for the production of organohalohydrosilanes by the catalytic reaction of activated silicon with mixtures of organohalides and hydrogen and the activated silicon catalysts per se. More particularly it relates to Direct Synthesis processes that exhibit enhanced reaction rates and selectivities by control of the concentration of trace metals permitted in the reaction mixture and the type of reactor used, and improved rate, stability and selectivity of the reaction by the judicious addition of selected metal additives, judicious addition of exogenous quantities of halosilanes and/or organohalosilanes during the course of the reaction.

DEFINITIONS

Throughout this document various terms and abbreviations are repeatedly used. To facilitate an early understanding of their meanings, their definitions follow:

Direct Synthesis = the one step synthesis process of this invention whereby organohalohydrosilanes are selectively and directly produced by the reaction of activated silicon with a mixture of an organohalide and hydrogen in the presence of controlled amounts of specified metal atoms and specified reaction conditions (both as hereinafter defined), and in contact with a catalyst in a fixed-bed, stirred-bed, fluidized bed or slurry-phase reactor.

Organohalohydrosilane(s) = one or more of the compounds of the general formula $R_aH_bSiX_c$, as hereinafter more fully defined, as applicable in the particular situation involved.

MeSiH = one or more of the organosilane compounds of the methylchlorohydrosilanes of the formulas $CH_3SiHCl_2$, $(CH_3)_2SiHCl$ and $CH_3SiH_2Cl$.

DH = $CH_3SiH_2Cl$.
DM = $(CH_3)_2SiHCl$.
MD = $CH_3SiHCl_2$.

Organohalosilane(s) = one or more of the organosilane compounds of the general formula $R_dSiX_{4-d}$, as hereinafter more fully defined, as applicable in the particular situation involved.

M = $(CH_3)_3SiCl$.
T = $CH_3SiCl_3$.
D = $(CH_3)_2SiCl_2$.

Halosilane(s) = one or more of the compounds of the general formula $H_dSiX_{4-d}$, as hereinafter more fully defined, as applicable in the particular situation involved.

TC = $HSiCl_3$.

HVS = the higher boiling fraction, above about 70° C. at atmospheric pressure, generally principally methylchlorodisilanes.

tr = trace, less than 0.05 weight percent by gas chromatography.

GC = gas chromatography.
GC/MS = gas chromatography/mass spectrometer.
GC/FTIR = gas chromatography/Fourier transform infrared spectroscopy.
o.d. = outside diameter.
i.d. = inside diameter.
$M^2/g$ = meters squared per gram.
BET = Braunnaueer-Emmet-Teller.
NA = not analyzed
ND = not detected
Me = methyl

BACKGROUND

The production of silanes, whether halosilane or organohalosilane or organohalohydrosilane, has long been known. The organohalohydrosilanes have found many applications and are generally useful intermediates for the synthesis of organosilicon coupling agents, silicone surfactants and in hydrosilylation and redistribution reactions. In fact, these compounds have come into such demand that the supply of the organohalohydrosilanes obtainable by current processes often does not satisfy the demand.

The direct reaction process described in U.S. Pat. No. 2,380,995, issued to Rochow, discloses the reaction of silicon with a methylhalide in the presence of a catalyst. This process, however, produces a mixture of silicon products with the methylhalohydrosilanes being produced in low yield and constituting only a small amount of the mixture, generally less than about 5 wt. % $CH_3SiHCl_2$ and less than about 1 wt. % of $(CH_3)_2SiHCl$ with no $CH_3SiH_2Cl$ when the methylhalide is mechylchloride. The bulk of the products produced consisted of $HSiCl_3$, $SiCl_4$, $(CH_3)_3SiCl$, $CH_3SiCl_3$, $(CH_3)_2SiCl_2$ and disilanes of the structure $(CH_3)_xSi_2Cl_{6-x}$, as well as a number of disilamethanes, siloxanes and hydrocarbons as shown in U.S. Pat. Nos. 2,598,435, 2,681,355, and 2,709,176. These mixtures require complex distillation processes to isolate and purify the small quantities of methylchlorohydrosilanes produced from hydrocarbon by-products of similar boiling points, as can be seen in U.S. Pat. No. 3,704,260 issued Nov. 28, 1972 to M. J. Wynn, and U.S. Pat. No. 4,181,673 issued Jan. 1, 1980 to H. Schumann, et al.

Voorhoeve (Organohalosilanes: Precursors to Silicones, Elsevier, N.Y., 1967, pp. 190–201) reports $C_2H_5SiHCl_2$ as the principal product of the direct reaction of ethyl chloride with copper-activated silicon. The more desirable $(C_2H_5)_2SiHCl$ and $C_2H_5SiH_2Cl$ are reportedly not obtained even when hydrogen is added along with the ethyl chloride at pressurized reaction conditions, as further shown in German Offen. No. 859,164, published Dec. 11, 1952 and Turetskaya, et al., Khim. Prom., p 18 (1963). These procedures fail to produce all three of the desired organohalohydrosilanes at a satisfactory high rate and/or selectivity.

Though various methods for the preparation of silanes using hydrogen, hydrogen chloride or metal hydrides have been published, they have all failed to satisfy the burgeoning demand for organohalohydrosilanes. Catalytic hydrogenation processes for the synthesis of $(CH_3)_2SiHCl$ and $CH_3SiHCl_2$ from methylchlorodisilanes are disclosed in U.S. Pat. No. 3,639,105, issued Feb. 1, 1972 to W. H. Atwell, et al., U.S. Pat. No. 4,059,608, issued Nov. 22, 1977 to Calas, et al. and U.S. Pat. No. 4,079,071, issued Mar. 14, 1978 to R. S. Neale. These processes require use of the disilanes as a starting material, however, the disilanes represent only a small fraction of the product usually obtained in a direct reaction process. For instance, in U.S. Pat. No. 4,500,724, issued Feb. 19, 1985 to Ward, et al., the disilanes represent from about 1 to 6 wt. % of the silanes produced. Further, the disilanes produced are typically deficient in $[Cl(CH_3)_2Si]_2$, which leads to high yields of (CH$_3$)$_2$SiHCl. The hydrochlorination of disilanes, as disclosed in U.S. Pat. Nos. 2,709,176, loc. cit., 2,842,580, and in Calas, et al., J. Organomet. Chem, 225, 117–130 (1982) typically results in more CH$_3$SiCl$_3$, CH$_3$SiHCl$_2$ and (CH$_3$)$_2$SiCl$_2$ and no (CH$_3$)$_2$SiHCl or CH$_3$SiH$_2$Cl.

Attempts at direct hydrogenation of alkylhalosilanes to alkylhalohydrosilanes have also been unsuccessful. The reaction is slow even at temperatures as high as about 1000° C. and pressures of about 1500 psig using Pd catalysts (Japanese Patent No. 82-47917; U.S. Pat. No. 2,595,620). This reaction introduces a further complication since the organohalodyrosilanes of the formulas R$_2$SiHCl and RSiH$_2$Cl are not sufficiently stable to withstand such high temperatures.

Syntheses of alkylchlorohydrosilanes via the metal hydride reduction of alkylchlorosilanes with NaH, Chalk, J. Organomet. Chem., Vol. 21, 95–101 (1970); Antipin et al., Russ. J. Gen. Chem., Vol. 40, p. 789 (1970); U.S. Pat. No. 3,704,261 issued Nov. 28, 1972 to Berger, et al.; CaH$_2$ (Simon, et al., J. Organomet, Chem., Vol. 206, p. 279 (1981)), NaBH$_4$ (U.S. Pat. No. 4,115,426 issued Sept. 19, 1978 to Hillrod, et al.) and LiAlH$_4$ (Eaborn, et al., J. Organomet. Chem., Vol. 18, p. 371 (1969)) are also disclosed. These are not practiced commercially because of the relatively high cost of metal hydrides and the need to dispose of the stoichiometric amounts of metal chlorides that are formed during the reduction reactions.

The yield of organohalohydrosilanes of formula RHSiX$_2$ is increased by the use of organochloride (e.g. CH$_3$Cl) and hydrogen halide (e.g. HCl) mixtures in the Rochow direct reaction synthesis (see Gorbunow, et al., Dokl. Akad. Nauk. SSR., Vol. 194, p. 92 (1970)). However, large quantities of the much less desirable RSiX$_3$ are simultaneously formed and the method is uneconomic.

The use of hydrogen-organohalide (e.g. CH$_3$Cl, C$_2$H$_5$Cl) mixtures in the Rochow direct reaction synthesis is disclosed in the following references: U.S. Pat. No. 2,380,998 issued Aug. 7, 1945, issued to Sprung, et al.; Brit. Pat. Nos. 590,654; 575,674; Ger. Pat. No. 859,164; Turetskaya et al., Khim. Prom., p. 18 (1963). These disclosures report increased formation of RHSiCl$_2$, but not R$_2$SiHCl or RSiH$_2$Cl.

DeCooker, et al., (J. Organomet. Chem., Vol. 99, p. 371 (1975); Ph.D. Diss. Univ. Delft, The Netherlands, 1976, Chps. 5 and 6) disclose that the addition of Zn, Cd, and Al to the copper-activated silicon used in the direct reaction synthesis with mixtures of CH$_3$Cl and H$_2$ at 300° C.-370° C. lowers the selectivity to CH$_3$SiHCl$_2$ and (CH$_3$)$_2$SiHCl. A summary of their results is shown in Table 1. The data show that selectivity to the methylchlorohydrosilanes is favored by high hydrogen partial pressures and high temperatures. However, the reaction rates are low and erratic and stable contact mass activity is not attained (DeCooker, 1976, Ph.D. Diss., Chp. 5, pp. 57–63; Chp. 6, pp. 64–73) even with the use of 10–15 wt. % Cu catalyst. Additionally, reaction performance parameters such as the ratio of CH$_3$SiHCl$_2$ to (CH$_3$)$_2$SiHCl and the overall preference of the methylchlorohydrosilanes (i.e., CH$_3$SiHCl$_2$+(CH$_3$)$_2$SiHCl) are variable even for duplicate experiments. The dissertation presents kinetics data (Chp. 6) on the direct reaction synthesis of CH$_3$SiHCl$_2$ and (CH$_3$)$_2$SiHCl from a contact mass (i.e., intimate mixture of Si, Cu, and Cu alloyed with Si) containing 0.1 wt. % Zn and 0.05 wt. % f Al. However, the maximum tolerable levels of Zn, Cd, and Al conducive to high selectivity to the desired compounds and stable mass activity are not defined. It is noteworthy (Chp. 6, p. 64) that the authors associate low selectivity to the methylchlorohydrosilanes with low CuCl concentrations. There are no teachings with respect to operation at superatmospheric pressures.

TABLE 1

Direct Synthesis of CH$_3$SiHCl$_2$ and (CH$_3$)$_2$SiHCl According to DeCooker*

| H$_2$ Partial Press. (atom) | Si Conv., wt. % | Temp. °C. | Cu wt. % | Zn wt. % | Al wt. % | DM mole % | MD mole % | T mole % | D mole % | Rate gm CH$_3$Cl/ kg Si, Hr |
|---|---|---|---|---|---|---|---|---|---|---|
| 0.55 | 20 | 332 | 10 | — | — | 32.7 | 37.6 | 3.4 | 23.4 | 75 |
| 0.55 | 40 | 332 | 10 | — | — | 30.8 | 23.8 | 9.9 | 33.1 | 100 |
| 0.75 | 55 | 332 | 10 | — | — | 33.1 | 45.7 | 6.9 | 12.5 | 75 |
| 0.55 | 65 | 332 | 10 | — | — | 24.4 | 51.1 | 4.8 | 17.3 | 85 |
| 0.55 | 25 | 332 | 10 | 0.1 | 0.05 | 17.5 | 30.8 | 4.7 | 45.8 | 40 |
| 0.75 | 50 | 332 | 10 | 0.1 | 0.05 | 28.5 | 56.7 | 2.7 | 10.3 | 40 |
| 0.75 | 60 | 332 | 10 | 0.1 | 0.05 | 17.5 | 70.3 | 2.7 | 5.0 | 50 |
| 0.58 | 20 | 370 | 10 | 0.1 | 0.05 | 23.0 | 26.6 | 5.3 | 42.1 | 180 |
| 0.58 | 50 | 370 | 10 | 0.1 | 0.05 | 31.6 | 39.5 | 3.2 | 23.9 | 290 |
| 0.55 | 20 | 334 | 15 | 0.1 | 0.05 | 13.4 | 29.5 | 3.2 | 49.5 | 65 |
| 0.55 | 40 | 334 | 15 | 0.1 | 0.05 | 17.4 | 36.0 | 4.1 | 39.6 | 75 |
| 0.55 | 70 | 334 | 15 | 0.1 | 0.05 | 8.0 | 62.4 | 12.7 | 5.4 | 50 |

*Data from Ph. D. Dissertation, Univ. Delft (1976). Chp. 5 and 6.
DM = (CH$_3$)$_2$SiHCl, MD = CH$_3$SiHCl$_2$, T = CH$_3$SiCl$_3$, D = (CH$_3$)$_2$SiCl$_2$.

French Patent No. 1,523,912 discloses the direct reaction synthesis of CH$_3$SiHCl$_2$ and (CH$_3$)$_2$SiHCl with CH$_3$Cl—H$_2$ mixtures at 350° C.–380° C. and 0–2.5 atmospheres gauge in which selectivity to the methylchlorohydrosilanes is improved by the addition of salts of the Group VIII metals (e.g., chlorides, oxalates and formates of Fe, Co, Ni) at 0.3–10 wt. %, preferably 0.3–2 wt. %, of the silicon contact mass. The formation of (CH$_3$)$_2$SiHCl and CH$_3$SiHCl$_2$ under the conditions illustrated in the examples of the patent is shown in Table 2.

Contrary to the teachings of DeCooker (loc. cit.) this French patent discloses (Examples 5 and 8; Claim 6) that 0.25–0.5 wt. % ZnCl$_2$ (equivalent to 0.12–0.25 wt. % Zn) is advantageously included in the mass to improve selectivity to the methylchlorohydrosilanes. However, there are no teachings regarding the control of the ratio of CH$_3$SiHCl$_2$ to (CH$_3$)$_2$SiHCl, or of the useful range of hydrogen partial pressures or of the maximum tolerable levels of other metals such as Cd, Al, or Sn. Examples 8 employs 15 wt. % Cu, but the useful copper catalyst levels are not otherwise defined. The reaction performance in the absence of the Group VIII metal salts is also not reported. Additionally, the conduct of the synthesis at 2.5 atmospheres gauge and 350° C. with 2.5 wt. % NiCl$_2$ as additive destroys the selectivity to $(CH_3)_2SiHCl$ (compare examples 1 and 3 of Table 2).

silanes. However, the processes heretofore disclosed do not produce sufficient significant amounts of the or-

TABLE 2

Direct Synthesis of $(CH_3)_2SiHCl$ and $CH_3SiHCl_2$ According to Fr. Pat. 1,523,912

| Additive | Example | $H_2$ Vol. % | DM Wt. % | MD Wt. % | T Wt. % | D Wt. % | Rate gm/kg Si, Hr | MD/DM | D/T |
|---|---|---|---|---|---|---|---|---|---|
| 2.5 wt. % $NiCl_2$ | 1 | 35.7 | 8.0 | 27.3 | 20.8 | 40.4 | 149 | 3.41 | 1.94 |
| 2.5 wt. % $CoCl_2$ | 2 | 7.1 | 4.0 | 37.0 | 33.0 | 22.5 | 75 | 9.25 | 0.68 |
| 2 wt. % $Ni(C_2O_4)$ | 4 | 35.7 | 7.0 | 27.0 | 26.7 | 37.2 | 128.5 | 3.86 | 1.39 |
| 2 wt. % $Co(C_2O_4)$ | 6 | 35.7 | 8.8 | 30.8 | 17.6 | 36.8 | 97.6 | 3.5 | 2.09 |
| 2 wt. % $Fe(C_2O_4)$ + 0.25 wt. % $ZnCl_2$ | 5 | 35.7 | 15.5 | 32.9 | 13.2 | 34.2 | 145.8 | 2.12 | 2.59 |
| 2 wt. % $Fe(HCOO)_2$ + 0.5 wt. % $ZnCl_2$ | 8 | 35.7 | 6.3 | 52.1 | 17.9 | 17.2 | 8.6 | 8.27 | 0.96 |
| 2 wt. % $NiCl_2$ | 3 | 27.3 | — | 42.9 | 25.1 | 19.1 | 164 | — | 0.76 |

All experiments at 380° C., 0 atom. gauge except Example 3, which was run at 350° C., 2.5 atom. gauge.
DM = $(CH_3)_2SiHCl$, MD = $CH_3SiHCl_2$, T = $CH_3SiCl_3$, D = $(CH_3)_2SiCl_2$.

As is shown, the literature fails to disclose a suitable direct reaction process capable of satisfying the demand for organohalohydrosilanes. None of the references disclose or suggest process conditions leading to the stable, reproducible formation of organohalohydrosilanes, in particular, alkylchlorohydrosilanes, that yield both high reaction rates and high selectivity to organohalohydrosilanes with good reproducibility and process stability.

OBJECTS OF THE INVENTION

Among the objects achieved by the present invention one can mention a facile process for the Direct Synthesis of organohalohydrosilanes in a consistent and reproducible manner. Another is the Direct Synthesis of organohalohydrosilanes in which the rate is generally high and reproducible without adversely affecting selectivity to compounds having silicon-hydrogen bonds and overall conversion of silicon. Other objects will become apparent from the following.

SUMMARY OF THE INVENTION

This invention pertains to the Direct Synthesis processes for the production of organohalohydrosilanes that exhibits enhanced reaction rate, reproducibility and selectivity to the such silanes, as well as overall conversion of silicon. The processes entail control of the amount of trace metals present, the type of reactor system used, and the addition of certain additives to the system. The critical features of the Direct Synthesis process of this invention required to achieve the primary objectives of said process include control of the concentrations of certain specified metal atoms in the activated silicon bed; the specific auxiliary agents and promoters and the concentrations thereof used; the effect on the reaction of the addition of calcium silicide to the activated silicon; and the ability to directly produce organohalohydrosilanes of the formula $RH_2SiX$ by conducting the Direct Synthesis in a fixed-bed reactor at high selectivity and rate, a feat not heretofore reported.

DESCRIPTION OF THE INVENTION

The direct reaction process for the production of silanes disclosed by Rochow, supra, is conventionally performed in a gas-solid reactor such as a fixed-bed, a stirred-bed, or a fluidized-bed reactor, all of which are known. In this conventional process an organohalide is reacted with activated silicon in contact with catalyst, promoters and auxiliary agents to form mixtures of ganohalohydrosilanes of the general formula $R_aH_bSiX_c$, the formation of organohalosilanes of the general formula $R_dSiX_{4-d}$ being favored to a considerable extent. In view of the commercial demand and need for the organohalohydrosilanes though many attempts have been made to increase the formation of these compounds none has been sufficiently successful. The Direct Synthesis processes of this invention have been successful in doing so; they have permitted the production of organohalohydrosilanes consistently and reproducibly at higher reaction rates, yields and selectivities than heretofore achieved. The means by which these advantages are now achieved were completely unpredictable and unexpected.

In the processes of this invention organohalohydrosilanes of the general formula:

$$R_aH_bSiX_c \quad \text{(I)}$$

are produced by the Direct Synthesis process at enhanced quantities and selectivity. In this formula R is an aliphatic or aromatic, saturated or unsaturated hydrocarbyl radical having up to about 20 carbon atoms, e.g., alkyl or alkenyl having up to about 10 carbon atoms, preferably up to about 6 carbon atoms; aryl, alkaryl, aralkyl having 6 or 10 ring carbon atoms and wherein the alk-group is as defined above; cycloalkyl having from 4 to 7 ring carbon atoms and which can be substituted with alkyl or alkenyl groups as are defined above; X is a halogen atom, e.g., chlorine, bromine, iodine and fluorine; a, b and c are integers having a value of 1 or 2 with the proviso that the sum of a plus b plus c is 4. Subgeneric to formula (I) are compounds of the formulas $RH_2SiX$, $RHSiX_2$ and $R_2HSiX$. Illustrative of such compounds are those tabulated below, which show the R, X, a, b and c components and values of the compounds represented by the above formulas.

TABLE A

| R | X | a | b | c |
|---|---|---|---|---|
| Methyl | Cl | 1 | 2 | 1 |
| Methyl | Cl | 1 | 1 | 2 |
| Methyl | Cl | 2 | 1 | 1 |
| Ethyl | Cl | 1 | 2 | 1 |
| Ethyl | Cl | 1 | 1 | 2 |
| Ethyl | Cl | 2 | 1 | 1 |
| Methyl | Br | 1 | 2 | 1 |
| Methyl | Br | 2 | 1 | 1 |
| Methyl | I | 1 | 2 | 1 |
| Ethyl | Br | 1 | 2 | 1 |
| Ethyl | Br | 2 | 1 | 1 |

TABLE A-continued

| R | X | a | b | c |
|---|---|---|---|---|
| Pentyl | Cl | 1 | 2 | 1 |
| Phenyl | Cl | 1 | 2 | 1 |
| Phenyl | Cl | 1 | 1 | 2 |
| Phenyl | Cl | 2 | 1 | 1 |
| Phenyl | Br | 1 | 2 | 1 |
| Phenyl | Br | 1 | 1 | 2 |
| Phenyl | Br | 2 | 1 | 1 |

The improved Direct Synthesis processes of this invention react an organohalide of the formula RX, wherein R and X are as previously defined, with activated silicon. Illustrative of suitable organohalides one can mention methyl chloride, methyl bromide, methyl iodide, ethyl chloride, ethyl bromide, phenyl chloride, vinyl bromide, and the like. Any organohalide that is known to react with activated silicon can be used with the preferred being those that vaporize under the reaction conditions employed, these compounds being well known to those skilled in this art. Methyl chloride is preferred.

Standard commercial grade methyl chloride of about 99.6 wt. % minimum purity is a preferred suitable starting material. However, means to remove trace contaminants or to prevent the introduction of volatile inhibitors and poisons (e.g., CO, $CO_2$, $O_2$, $H_2O$, $SO_2$) could be provided, if desired.

The term activated silicon has an accepted meaning in this technology. It refers to silicon into which a catalyst, one or more promoters and one or more auxiliary agents have been incorporated.

In this invention activation may be accomplished by any convenient known method, for example, solidifying a melt containing the catalyst (e.g., copper) and silicon and comminuting the solid into particles; or by heating a mixture of silicon and catalyst as described in U.S. Pat. No. 2,380,996; or by heating mixtures of silicon, catalyst and promoters in the presence of hydrogen and/or hydrogen chloride as described in U.S. Pat. Nos. 2,380,997 and 4,314,908, issued Feb. 9, 1982 to Downing et al; or by heating a mix of a salt of the catalyst (e.g., cuprous chloride) and silicon as described in U.S. Pat. No. 2,119,808 at elevated temperature. These and many other activation methods, catalysts, promoters and auxiliary agents are known in the art.

As is known in the art, activation is the process of incorporating into the silicon quantities of catalyst, promoter and auxiliary agent. This may be done in the same reactor used for the reaction of the organohalide-hydrogen mixture, or in a separate reactor. In the latter situation, the activated silicon is typically and desirably transported to the organohalide hydrogen reactor in an anhydrous, non-oxidizing atmosphere.

A preferred method of activation for the Direct Synthesis of the present invention employs cuprous chloride and chlorosilanes ($HSiCl_3$, $SiCl_4$), methylchlorosilanes ($CH_3SiCl_3$, $(CH_3)_2SiCl_2$), or their mixtures. The chlorosilanes and methylchlorosilanes are vaporized and transported into the reactor in amounts sufficient to fluidize the mixture of silicon and cuprous chloride. Other gases such as hydrogen, nitrogen, argon, and helium which do not impair the subsequent performance of the activated silicon may be added along with the vaporized chlorosilanes and methylchlorosilanes to assist fluidization. Temperatures above 200° C. are necessary for this activation and values between 280°-380° C. are preferred.

The catalyst used in this invention is a metallic element, e.g., copper or silver, or their compounds. The suitable catalysts, including the above, are well known and are fully described in the literature. However, the literature contains no recognition of the significant effect the presence of trace amounts of other elements has on the reaction. The accepted theory is that the metal atom fuses with and diffuses into the silicon to form an alloy or solid solution, which is the phase that reacts with the organohalide.

The preferred catalysts for the Direct Synthesis process of the instant invention are powdered metallic copper, any anhydrous copper compound, or mixtures thereof. Metallic silver, its compounds and their mixtures, however, also are known to be effective catalysts. Examples of copper compounds suitable for use individually or in mixtures are cuprous oxide, cuprous chloride, cupric chloride, copper nitride, copper hydroxide, and copper carboxylates such as copper formate. This, however, is not a restrictive or exclusive list.

Copper compounds specifically contraindicated are those such as copper sulfides and intermetallic compounds of lead and copper, which introduce into the reaction intolerable levels of compounds or elements known to exert a negative effect on its rate and/or selectivity and/or stability. Additionally, Zn, Sn, Cd, and other promoters of dialkyldihalosilane formation which impair selectivity to the alkylhalohydrosilanes are to be avoided or their concentrations maintained at the levels prescribed, as hereinafter discussed.

A preferred copper catalyst is cuprous chloride. Another preferred catalyst is a powdered mixture of copper, cuprous oxide, and cupric oxide such as is produced by atomization and partial oxidation of molten copper, by the partial oxidation of electrolytically or chemically produced copper metal, or by the incomplete reduction of cupric oxide. Mixtures of copper and copper oxides produced by cementation generally contain quantities Zn, Cd, and Sn which lower the selectivity to the alkylhalohydrosilanes as is subsequently shown. During cementation, an aqueous copper-bearing solution is contacted with Al, Fe, Zn or another metal higher in the electrochemical series than copper. The copper precipitates and the metal dissolves. As a result of partial air oxidation, the precipitate is a mixture of copper, cuprous oxide and cupric oxide. Copper catalysts prepared in this way are known as cement catalysts. Those partially oxidized copper catalysts not so prepared are called non-cement catalysts. Copper formate is another preferred catalyst, in particular, copper formate with a layered or lamellar crystal structure is especially preferred. This crystal structure is characterized by intense reflections in the X-ray powder pattern of copper formate at d-spacings from 3.0-3.1 Angstroms and from 5.0-6.5 Angstroms. The preferred copper formate catalysts also undergo complete thermal decomposition from about 170° C. to about 200° C. The copper formate may be hydrated or anhydrous, but is desirably the anhydrous solid prepared by methods known to preserve the lamellar structures.

In order to achieve the selectivity and rate values which characterize the instant invention, the Cd and Zn concentrations in the catalyst should be as a total below 0.07 wt. % and preferably less than 0.01 wt. %. The Sn content should be <0.002 wt. %. The Pb content should be 0.07 wt. % at a maximum and is preferably less than 0.005 wt. %. The iron and aluminum content of the catalyst is each preferably 0.3 wt. % maximum.

The stated concentrations of Zn, Cd and Sn are critical for this invention.

Catalyst particles up to a maximum size of 100 microns are useable for the process of this invention. However, it is preferable that the particles be less than 50 microns and most preferable that they be 2-25 microns. A minimum BET surface area of 0.1 m$^2$/gm is generally acceptable. Values above 1 m$^2$/gm are preferred for good catalyst dispersion.

The amount of copper required to activate the silicon is usually less than about 10 wt. % of the silicon used. In general, amounts of copper in the range 0.05-3 wt. % have been found to be optimal. The prior art (see DeCooker, et al., Morozov, et al. loc. cit.) for the direct synthesis of alkylhalohydrosilanes discloses the use of copper in the range 10-15 wt. %. The present invention, however, can use copper concentrations of 0.5-1.5 wt. % and achieve the performance advantages recited hereinabove.

The silicon employed in the Direct Synthesis process of this invention is a technical grade material preferably containing at least about 98.5 wt . % Si. Trace metals which occur in the technical grade silicon used in the conventional direct reaction process have been identified by N. P. Lobusevich, et al., Russ. Jour. Appl. Chem., Vol. 49, No. 10, pp. 2168-2174 (1976). In general silicon employed in the conventional synthesis may be used in the instant invention provided about the following specifications are satisfied: Si $\geq$ 98.5 wt. %, Al=0.1-0.4 wt. %, Fe=0.3-0.6 wt. %, Ca=0.01-0.15 wt. %, Ti=0.03-0.06 wt. %, Mn=0.005-0.01 wt. %, Zn<0.005 wt. %, Sn$\leq$0.0005 wt. %, Pb<0.001 wt. %, Bi<0.005 wt. %, Sb<0.005 wt. %, Ni=0.001-0.2 wt. %, Cr=0.0005-0.02 wt. %, Co$\leq$0.005 wt. %, Cd$\leq$0.005 wt. %. The Al, Bi, Cd, Cr, Ni, Pb, Sb, Sn, and Zn levels are particularly critical to the selectivity to R$_2$SiHX and RSiHX$_2$ compounds. For example, Al values in excess of 0.4 wt % can lead to <10 wt. % Me$_2$SiHCl in the reaction product. Values lower than 0.1 wt. % Al may impair the reactivity of the silicon. Promoters of dimethyldichlorosilane formation and conventional auxiliary agents, e.g., Zn, Cd, Bi, Sb, Sn, if present at concentrations in excess of the ranges shown above inhibit the formation of the organohalohydrosilane compounds. The Pb specification is especially critical. Values as low as 0.005 wt. % can cause considerable loss of reactivity. A specially preferred silicon for this invention is that which contains 0.004-0.02 wt. % Ni and 0.002-0.01 wt. % Cr.

A broad range of silicon particles, e.g. 28 X D mesh (i.e. no larger than 500 microns), may be employed in the synthesis. It is preferred, however, that the silicon particles be smaller than about 48 mesh (i.e. less than 300 microns) and larger than about 325 mesh (i.e. larger than 45 microns). Smaller particle sizes tend to contribute to good fluidization of the bed and assist heat transfer. The particle size range employed in any given reaction depends on the size of the reactor and the scale of the synthesis. In laboratory experiments, the preferred particle size range has been found to be 65×150 mesh (i.e. 104-208 microns), but this distribution is not considered essential for the success of our process.

Preformed metal silicides such as those of calcium, magnesium and copper may also be present in the synthesis either as individual phases or admixed with elemental silicon. The presence of calcium silicides (e.g. CaSi$_2$) is particularly beneficial to the formation of R$_2$SiHX compounds even when present in the relatively modest amount of 1-10 wt. %. The preferred level is 2-8 wt. %. This is dictated by the need to maintain both the reaction temperature and the fluidization of the particles within controllable limits. The reaction of calcium silicides with alkyl halides is very exothermic. Consequently, the presence of >10 wt. % calcium silicides in silicon can have undesirable effects. It is also essential that the calcium silicide not contain quantities of Al, Fe, Zn, Sn and other metals which can exert negative effects on the rate of formation of the organohalohydrosilane compounds and on the selectivity to R$_2$SiHX in particular.

In the Direct Synthesis process of this invention the concentrations of various metal atoms present in the activated silicon bed undergoing reaction with the organohalide is critical. It is an important feature of this Direct Synthesis that the activated silicon bed contain the metal atoms in the following weight percent values. The amount of zinc, antimony and cadmium, either individually or totally, should be less than about 0.05 weight percent, preferably less than about 0.01 weight percent, and most preferably less than 0.005 weight percent. The tin concentration should be less than about 0.01 weight percent preferably less than about 0.005 weight percent, and most preferably less than 0.0005 weight percent. The nickel concentration should be from about 0.001 to about 0.02 weight percent, preferably from about 0.002 to about 0.01 weight percent, and most preferably from about 0.004 to about 0.008 weight percent. The chromium concentration should be from about 0.001 to about 0.06 weight percent, and most preferably from about 0.0005 to about 0.01 weight percent. The aluminum concentration can be from about 0.1 to about 0.4 weight percent, preferably from about 0.1 to about 0.2 weight percent.

In the prior conventional direct reaction processes promoters have been included at significant concentrations to potentiate the formation of diorganodihalosilanes of the formula R$_2$SiX$_2$, wherein R and X are as previously defined. These conventional promoters are the elements such as Zn, Cd, Hg, As, Sb, Bi and their compounds. In the Direct Synthesis processes of this instant invention, however, the presence of any significant amount of one or more of such conventional promoters is detrimental and serves to diminish the selectivity to organohalohydrosilane formation; thus, the amounts thereof must be controlled to the critical values herein defined.

In the Direct Synthesis process of the present invention, the term promoter refers to the elements Ni, Cr, Rh, Pd and their compounds. These promoters are those which have now been found to enhance the formation of the organohalohydrosilanes of Formula I.

The promoters used in the processes of this invention afford satisfactory rate and selectivity in the Direct Synthesis of organohalohydrosilanes. The promoters of this invention, when used at effective levels, favor the increased formation of RHSiX$_2$, R$_2$SiHX and/or RSiH$_2$X in the Direct Synthesis processes of this invention. The promoter is preferably in powdered form as the element, oxide, halide, or silicide, with a particle size distribution similar to that of the catalyst. For beneficial and sustained rate and selectivity it is desirable to employ activated silicon prepared from silicon containing the promoter(s) well distributed throughout the mass of the particles. Inhomogeneous distribution can lead to only transitory realization of the benefits.

French Patent No. 1,523,912 discloses the use of salts of the Group VIII elements (e.g., Fe, Co, Ni) at 0.3–10 wt. % in order to increase the overall selectivity (i.e. MeSiH or MeSiH/D) to the organohalohydrosilanes. However, there is no teaching or suggestion regarding the selection of promoters to favor $RSiHCl_2$ over $R_2SiHCl$ or vice versa (i.e. MD/DM). The present invention teaches the control of MD/DM both by the choice of promoter as well as by its concentration. In French Patent No. 1,523,912, nickel salts (e.g. nickel chloride, nickel oxalate, and nickel formate) are employed at 0.3–10 wt. % in the activated silicon. The lower limit of nickel salt concentration (i.e. 0.3 wt. %) is equivalent to 0.12–0.14 wt. % Ni.

The present invention is characterized by the advantageous use of Ni concentrations less than 0.1 wt %, preferably 0.002–0.08 wt % and most preferably 0.004–0.02 wt %. At concentrations in these ranges, nickel increases the rate of the reaction between the activated silicon and the organohalide-hydrogen mixture. Contrary to the teachings in the French Patent No. 1,523,912, the selectivity to organohalohydrosilanes of general formula, $R_2SiHCl$ (e.g. $(CH_3)_2SiHCl$), is maintained at these lower nickel concentrations when the reaction is performed at super-atmospheric pressures. Nickel concentrations in excess of 0.1 wt % favor the increased formation of organotrihalosilanes, $RSiX_3$ (e.g. $CH_3SiCl_3$), at the expense of the organohalohydrosilanes. Use of the preferred values of Ni will generally result in MD/DM=2–5, MeSiH/D>1.0, rate >1 wt % Si/hr when the reaction is performed at 290°–325° C. and 0–30 psig in a fluidized bed with 50:50 or 60:40 $H_2$—$CH_3Cl$ by volume.

Chromium additions of <0.5 wt % to the activated silicon provide improved selectivity to $R_2SiHX$ (e.g. $(CH_3)_2SiHCl$) relative to $RSiHX_2$ (e.g. $CH_3SiHCl_2$). Additions less than or equal to 0.1 wt % are particularly advantageous. Concentrations retained within the activated silicon mixture should preferably be 0.0005–0.006 wt %. Thus the use of silicon containing 0.005 wt % Cr afforded MD/DM=2–3 and MeSiH/D=6–8 when the reaction was conducted with 60 vol. % $H_2$–40 vol. % $CH_3Cl$ at 320° C. and 30 psig in a fluidized bed.

Rhodium also increases selectivity to organohalohydrosilanes of general formula, $R_2SiHX$ (e.g. $(CH_3)_2SiHCl$), when introduced at concentrations below 1 wt %. In contrast, inclusion of palladium at 0.5 wt % enhances the selectivity to the compounds, $RSiHX_2$ (e.g. $CH_3SiHCl_2$). Both Rh and Pd are Group VIII elements. However, their use for the control of $R_2SiHX$ and/or $RSiHX_2$ content is not disclosed in French Patent No. 1,523,912.

The auxiliary agents used in the past have generally been elements such as Sn and Cs, and their compounds. These have been added to improve the rate of the reaction and/or the selectivity of the reaction to the diorganodihalosilanes $R_2SiX_2$ and/or to reduce the formation of higher boiling compounds such as disilanes; a prerequisite being that both the catalyst and promoter are present in adequate amounts.

In the Direct Synthesis process of the instant invention, the auxiliary agents are the halosilanes of the formula $H_dSiX_e$ and the organohalosilanes of the formula $R'_fSiX_{4-f}$, wherein R' is alkyl of from 1 to 6 carbon atoms, preferably 1 or 2 carbon atoms, or phenyl, and is preferably methyl; X is halogen; d has a value of 0 to 3; e has a value of 1 to 4; the sum of d plus e is 4; and f has a value of 1 to 3. In addition, the organohalohydrosilanes of Formula I are also suitable auxiliary agents. The auxiliary agents are those compounds of the above formulas which when injected into the bed activate the mixture of silicon and catalyst particles as well as potentiate the selectivity to organohalohydrosilanes. Thus, they serve to increase the rate and selectivity, a dual benefit that was completely unexpected and unpredictable.

The auxiliary agents used in the Direct Synthesis process of the present invention are the halosilanes (e.g. $HSiCl_3$, $SiCl_4$), organohalohydrosilanes, organohalosilanes (e.g. $CH_3SiCl_3$) defined above and their mixtures which exert their principal effect on the rate of the Direct Syntheses of this invention of the organohalohydrosilanes. They may be employed in two different modes. First, the auxiliary agent may be used to activate the mixture of catalyst, promoter, and silicon. In this mode, the auxiliary agent is usually vaporized and its vapor used to fluidize the mixture of solids at the activation temperature (e.g., 280°–350° C.). The vapor may also be admixed with quantities of inert gases such as nitrogen, argon, helium, and hydrogen. In the second mode, the auxiliary agent may be introduced for short (i.e., less than one hour) or long periods during the course of the Direct Synthesis of this invention in order to improve the reaction rate and selectivity. Typically, the rate enhancement is observed following the termination of the auxiliary agent injection.

When used in the activation step, the auxiliary agent should be at least about 10 vol. % of the gases used to fluidize the bed. Lower values can be effective, but the reaction performance may be erratic. It is preferable to employ >50 vol. % of the fluidizing gas as the auxiliary agent and most preferable to employ 90–100 vol. %. The auxiliary agent is recovered from the activation by condensation of the vapors in a substantially unconverted form. It may be recycled and reused for subsequent activations.

When the halosilane or organohalosilane or organohalohydrosilane is injected during the course of the Direct Synthesis of this invention, it is essential that the injection be made rapidly if the full benefit of the use of the auxiliary agent is to be realized. During the period of the injection the overall rate of the synthesis is suppressed. Accordingly, it is desirable to limit this period to at most 6 hours and preferably one hour or less. Periods of about 1 to 20 minutes have been found to be advantageous in laboratory work. However, even shorter periods may be employed if the benefits are not removed by their use.

The quantity of the auxiliary agent injected should be at a minimum 0.0001 wt % per minute based on the weight of activated silicon in the reactor. The maximum quantity should not be so large as to make the total volume of gas (i.e. organohalide, hydrogen and auxiliary agent) capable of expelling the solid particles from the reactor. A value of about 10 wt % per minute is a practical upper limit. The preferable range is about 0.02–3 wt % per minute. Relative to the organohalide reactant, the auxiliary agent should be about 0.002–2 times on a weight basis and preferably about 0.2–2 times.

In order to avoid cross-contamination of products, it is desirable to use as auxiliary agents the halosilanes, organohalohydrosilanes and organohalosilanes having the same halogen and organo groups as the Direct Synthesis being performed by the process of this invention. For example, $CH_3SiCl_3$ is preferred as the auxiliary agent in the Direct Synthesis of methylchlorohydrosilanes over $C_2H_5SiBr_3$.

The use of the auxiliary agent during the silicon activation improves the dispersion of the copper catalyst on the silicon surface. Prolonged use of hydrogen (i.e. in the hydrogen-organohalide mixture) causes sintering of the copper particles and decrease of the reaction rate. Sintering can be reversed or forestalled, dispersion increased and reaction rate improved by the intermittent injection of the auxiliary agent.

The prior art (Russ J. App. Chem., Vol. 38, No. 12, pp. 2886 (1965); a series of articles by Lobusevich et al., Russ. J. Gen. Chem. Vol. 48, No. 12, pp. 2055-2060 (1978); Vol. 48, No. 11, pp. 2290-2307 (1978)) teaches that methylchloro-silanes and chlorosilanes may be recycled into the conventional reaction between methyl chloride and activated silicon. With the injection of methyltrichlorosilane, its additional formation during the reaction was suppressed and selectivity to dimethyldichlorosilane was enhanced. However, the overall rate of the reaction was also suppressed during the recycling experiment. Additionally, conventional promoters continuing Zn, Cd, Sb, or Al and their mixtures with alkali metal salts, such as KCl, were required for the high selectivity to dimethyldichlorosilane. The instant invention is concerned with the Direct Synthesis of methylchlorohydrosilanes and requires both methyl chloride and hydrogen as co-reactants. Conventional promoters are specifically contraindicated as additives to the activated silicon of the instant invention. Moreover, the post-injection rate increase attendant to this invention is observed only with the simultaneous use of methyl chloride hydrogen mixtures and the use of activated silicon having the composition defined hereinabove.

The hydrogen content of the organohalide-hydrogen mixture affects both the rate and selectivity of the Direct Synthesis of this invention. Rate decreased with increasing hydrogen partial pressure. However, selectivity to the organohalohydrosilanes increases with hydrogen partial pressure. The relationship between selectivity expressed as the total percentage of organohalohydrosilanes in the product (i.e. % MeSiH), and hydrogen partial pressure (or volume percent $H_2$ in the organohalide hydrogen mixture) is sigmoidal. Hydrogen concentrations less than 20 volume percent of the mixture give low selectivities (e.g. MeSiH<20 wt %, MeSiH/D<1). Concentrations in excess of 85 volume percent produce very high selectivities (e.g. MeSiH>75 wt %, MeSiH/D>3). The best balance between selectivity and rate is achieved by operating at about 40-75 volume percent hydrogen and preferably at about 45-60 volume percent. In this preferred range, rates are greater than 1.5% Si/hr and MeSiH/D≧1.5 under the preferred conditions of this invention.

The total amount of gaseous reactant (i.e. organohalide-hydrogen mixture and occasionally, auxiliary agent) employed in this invention must be, as a minimum, sufficient to fluidize the activated silicon particles and must, of course, be less than that flow which completely discharges or elutriates the activated mass from the reactor before the silicon particles have reacted. The minimum flow for fluidization may be computed from a knowledge of the gas densities, the density and particle size distribution of the activated silicon, and the temperature of the reaction, as described for example in the monograph, Fluidization Engineering, by D. Kunii and O. Levenspiel (John Wiley & Sons, N.Y., 1969). It is possible to operate the bed at many times this minimum flow and still keep the reacting, activated silicon particles contained in the reactor in a fluidized state. For example, in a laboratory glass reactor at atmospheric pressure and 325° C., the minimum linear fluidization velocity of silicon particles with average size 149 microns was found to be approximately 1.5 cm/sec. The minimum linear fluidization velocity of the particles in a carbon steel reactor at 30 psig and 300° C. was found to be 1.73 cm/sec. Voorhoeve (loc. cit. p. 154) has reported 1.8 cm/sec and Lobusevich, et al. (Soviet Chem. Ind. No. 2, p. 83 (1974)) 2.0 cm/sec as experimentally determined values for silicon particles 105-250 microns with a mean of 150 microns. Operational values of 2-5 times this minimum are preferred for the Direct Synthesis of $RSiHX_3$ and $R_2SiHX$ by the process of this invention. The Direct Synthesis of $RSiH_2X$ by the process of this invention is best performed in a fixed bed reactor.

The minimum temperature of the Direct Synthesis of this invention for the production of organohalohydrosilanes is set by the initiation temperature of the reaction between the organohalide and the activated silicon. These temperatures are recorded in the above-cited monograph by Voorhoeve and Petrov et al., Synthesis of Organosilicon Monomers, published by Consultants Bureau, N.Y. (1976). For example, at atmospheric pressure, the minimum temperature for methyl chloride reaction is about 290° C. The maximum acceptable temperature may be determined by the onset of organohalide pyrolysis. Such pyrolysis is usually accompanied by markedly increased formation of the less desirable organotrihalosilane, $RSiX_3$, and hydrocarbon by-products. Temperatures above 380° C. lead to low $R_2SiHX$ formation and/or $R_2SiHX$ decomposition.

Optimum temperatures are those which permit facile reaction and volatilization of the products without the complexities of organohalide pyrolysis or organohalohydrosilane thermal stability. When the organohalide is methyl chloride, and the hydrogen content is 50 vol. percent, the content of methylchlorohydrosilanes in the condensed reaction product is generally at least about 50 wt % in the optimum temperature range. This range extends from about 300°-370° C. and preferably about 320°-340° C. at atmospheric pressure. At 2-5 atmospheres gauge, the range is broadly about 260°-350° and preferably about 280°-330° C. Within these preferred ranges there are no statistically significant changes of product composition with temperature for reactions performed in fluidized bed reactors.

As may be appreciated from the foregoing, the Direct Synthesis process of this invention for the production of organohalohydrosilanes may be carried out at atmospheric or at superatmospheric pressures. It is advisable to conduct the synthesis under pressure since this increases the rate of the reaction and makes more efficient use of the hydrogen, organohalide, and activated silicon. A maximum pressure (measured at the top of the fluidized-bed reactor) of about 6, or more, atmospheres gauge assures controllable reaction rates. An optimum range of about 2-4 atmospheres gauge allows the process to be operated smoothly and controllably at acceptable selectivities for prolonged periods.

In its preferred form, the Direct Synthesis process of the present invention is conducted in a fluidized-bed reactor utilizing copper-activated silicon, a nickel promoter, a gaseous organohalide-hydrogen mixture, and a gaseous organohalosilane auxiliary agent. The reactor may have a single nozzle or multiple nozzles for continuous introduction of the gaseous mixture. Means of continuous or intermittent addition of copper-activated silicon, promoters and auxiliary agents are also provided. Means for the continuous removal of gaseous reaction products, unreacted organohalide and hydrogen and elutriated fine particles are also desirably provided. Conventional techniques and equipment are known and may be utilized. As will be shown in Example 11 the synthesis of $RSiH_2Cl$ is preferentially performed in a fixed bed reactor.

Conventional means are available for separating the solid particles from the hot gases (e.g. with cyclones and/or filters) as well as for cooling and condensing the hot product mixture in a vessel separate from, but connected to the fluidized-bed reactor, if desired. Other operational details relevant to the fluidized-bed reactor and the separation and recovery of the reaction products are well known to those skilled in the art, and thus will not be fully described herein.

Steady-state operation is typically defined as the condition in a direct reaction wherein the rate and selectivity parameters have attained stable values following an initial induction or unstable period. Provided the supply of activated silicon, promoter and reactive organohalide, or its mixture with another gas, are continued at their preferred rates the steady-state condition extends for a very long time, for example, from less than 10 percent Si conversion through more than 50 percent Si conversion.

Diorganodihalosilanes are the preferred products of the conventional prior art Rochow direct reaction process. A quantitative measure of this preference is the gravimetric ratio, wt % $R_2SiX_2$/wt % $RSiX_3$, usually abbreviated D/T and referred to as the selectivity of the direct synthesis; these values by our process are reported herein.

The instant invention concerns the preferred synthesis of the organohalohydrosilanes. Consequently, other quantitative measures of reaction selectivity are required. These performance parameters are defined hereinbelow for the case wherein the organohalide is methyl chloride (MeCl).

In the examples and tables the expression, MeSiH, denotes the overall content of methylchlorohydrosilanes in the reaction product. Thus, $$MeSiH = (MeHSiCl_2 + Me_2SiHCl + MeSiH_2Cl)$$

It is expressed either as a gravimetric or molar percentage.

The preference shown for $MeHSiCl_2$ relative to $Me_2SiHCl$ is denoted by the molar or gravimetric ratio, $MeHSiCl_2/Me_2SiHCl$, abbreviated MD/DM. The expression, $$\frac{MeSiH}{D} = \frac{(MeHSiCl_2 + Me_2SiHCl + MeSiH_2Cl)}{Me_2SiCl_2}$$

measures the overall selectivity of SiH compounds relative to the conventional main product, dimethyldichlorosilane. It may be either a gravimetric or molar ratio.

The overall rate of the Direct Synthesis process of this invention is defined as the quantity of raw material reacted per unit time, e.g. grams Si reacted per kilogram Si in the reactor per hour, or percent Si reacted per hour, or gram MeCl reacted per gram Si in the reactor per hour. These definitions are used in the instant invention. In addition, there are other definitions germane to the instant synthesis, specifically the weight or volume or molar fraction (or percentage) of hydrogen converted per unit time and the molar or gravimetric amount of organohalohydrosilane produced per gram Si per unit time. High selectivity to the organohalohydrosilanes ensures that the overall silicon conversion rate to produce all the reaction products will not be very much larger than the sum of the specific rates of formation of $RSiHX_2 + R_2SiHX + RSiH_2X$.

In accordance with the Direct Synthesis process of the present invention, utilizing the preferred and defined activated silicon affords both a high reaction rate and high selectivity to the organohalohydrosilanes. For the preferred case of methylchloride-hydrogen as the gaseous reaction mixture, reaction rates by our invention greater than 1 wt % Si converted per hour and selectivities, MeSiH > 50 wt % of the reaction product, MD/DM ≦ 5.0, MeSiH/D > 1.0 are simultaneously attained at steady-state. Preferably, the reaction rates by our invention are greater than 2 wt % Si conversion per hour, MeSiH > 70 wt %, MD/DM ≦ 3.0 and MeSiH/D > 2.0 at the steady-state condition. The obtention of these steady-state rates and selectivities may be achieved at a temperature of from about 290° to 330° C. and at a pressure up to about 4 atmospheres gauge.

Most important, however, this invention teaches the control of the rate and selectivity parameters of our Direct Synthesis of the methylchlorohydrosilanes. The values of the parameters depend on the trace metal content of the activated silicon as well as on the specific chlorosilanes or methylchlorosilanes injected. This flexibility is fully illustrated below in the Examples.

As stated previously, the principal products of the conventional prior art processes when using methyl chloride as the organohalide are $HSiCl_3$, $Me_2SiHCl$, $MeHSiCl_2$, $Me_3SiCl$, $SiCl_4$, $MeSiCl_3$, $Me_2SiCl_2$, $Me_xSi_2Cl_{6-x}$ ($0 < x \leq 6$, x is an integer), various methylchlorosilamethanes, methylchlorodisiloxanes, and methylchlorotrisilanes. In this list the compounds following $Me_2SiCl_2$ all have normal boiling points above 70° C. and comprise the heavies or higher boiling fraction. Typically $Me_2SiCl_2$ is at least 80 wt % of the reaction products, $MeSiCl_3$ is 1-5 wt % and the higher boiling fraction is 1-6 wt %.

The compounds formed by the process of the invention by the use of methyl chloride and hydrogen are the same except that $MeSiH_2Cl$ is also produced. The preferred compounds of the instant invention are $MeSiH_2Cl$, $Me_2SiHCl$, and $MeHSiCl_2$. Pursuant to this invention the overall content of these compounds in the reaction product is at least 50 wt % and, preferably, at least 70 wt %. $MeSiH_2Cl$ is at least 1 wt %; $Me_2SiHCl$ is at least 10 wt % and, preferably, at least 20 wt %; $MeHSiCl_2$ is at least 40 wt % and, preferably, at least 50 wt %. That these organohalohydrosilanes could be directly synthesized at such high selectivities was completely unexpected and unpredictable.

By use of this invention, the typical levels of certain of the by-products are as follows: $MeSiCl_3$ is at most 20 wt %, $Me_2SiCl_2$ is in the range 20-50 wt %, $Me_3SiCl$ is at least 1.0 wt % and the higher boiling fraction is at most 1.0 wt %. Indeed, the process of the instant Direct Synthesis can generally reduce the quantity of the higher boiling fraction to undetectable (i.e. <0.05 wt % by gas chromatography) levels.

The following examples serve to further illustrate this invention. In the examples certain catalysts and silicon materials were used; to facilitate matters these are tabulated in Tables 3 and 4.

Table 3 summarizes the analyses of the copper catalysts used in the examples.

TABLE 3

| | Composition of Copper Catalysts | | | | | |
|---|---|---|---|---|---|---|
| Element | C-1 | C-2 | C-3 | C-4 | C-5 | C-6 |
| Cu (a) | 64.1 | 64 | 65 | 81.8 | 87.9 | 64.2 |
| Al ppm | 90 | <1 | 2 | 2070 | <24 | 5 |
| As ppm | N.A. | <1 | N.A. | 892 | <20 | 4 |
| Cd ppm | <20 | <1 | <1 | <10 | <10 | <1 |
| Cr ppm | <12 | <12 | <12 | 44 | <23 | <12 |
| Fe ppm | <20 | 396 | <1 | 16400 | 190 | 12 |
| Ni ppm | <20 | <1 | <1 | 165 | <23 | <1 |
| Pb ppm | <50 | 95 | <1 | 358 | 106 | <1 |
| Sb ppm | <20 | <20 | <1 | <25 | <23 | <1 |
| Sn ppm | <20 | <20 | <10 | 1200 | 126 | <10 |
| Zn ppm | <100 | 750 | 300 | 987 | 42 | 300 |

(a) Weight percent copper

The silicon used in the examples was obtained from commercially available sources and all materials had particle sizes from abut 100 microns to about 208 microns. Table 4 presents a summary of the trace elements analyses of the silicon materials used in the examples.

TABLE 4

| | Trace Elements Content of Silicon Samples | | | | | |
|---|---|---|---|---|---|---|
| Element | Si-1 | Si-2 | Si-3 | Si-4 | Si-5 | Si-6 |
| Al wt % | 0.28 | 0.24 | 0.23 | 0.25 | 0.14 | 0.18 |
| Ca ppm | 149 | 176 | 244 | 317 | 196 | 318 |
| Cd ppm | <1 | <2.5 | 17 | <2.5 | <1.0 | <2 |
| Cr ppm | 60 | 46 | 22 | 7.9 | 66 | 181 |
| Cu ppm | 86 | 24 | 34 | 12 | 24 | 45 |
| Fe wt % | 0.44 | 0.39 | 0.18 | 0.27 | 0.36 | 0.26 |
| Mn ppm | 80 | 111 | 12 | 16 | 105 | 252 |
| Ni ppm | 16 | 20 | 13 | 81 | 53 | 20 |
| Pb ppm | <2 | <2.5 | <7 | <2.5 | <2.5 | <2 |
| Sb ppm | <2 | <2.5 | <3 | <2.5 | <2.5 | <2 |
| Sn ppm | <2 | <2.5 | <3 | <2.5 | <2.5 | <3 |
| Ti ppm | 365 | 339 | 254 | 386 | 321 | 546 |
| V ppm | 23 | 33 | 10 | 10 | 92 | 56 |
| Zn ppm | 3 | 4 | 3 | <3 | <2 | 8 |
| Zr ppm | 46 | 49 | 22 | 23 | 23 | 43 |

In the examples two different reactors were used. Reactor A was used only at atmospheric pressure and Reactor B was of adequate construction to enable its use at superatmospheric pressure; these are described below.

Reactor A

This was a conventional Vycor ® fluidized-bed reactor of overall length 91 cm and i.d. 3.5 cm. A sintered glass frit at the base of the reactor supports the bed of silicon or activated silicon particles and disperses the reactant gas (i.e. organohalide-hydrogen mixture) as it enters the bed. A Vycor ® reservoir, vented with nitrogen, is attached to the reactor near its base just above the frit to permit the intermittent addition of catalyst, promoter and/or additional silicon or activated silicon to the reactor. The junction of the reservoir and the reactor is normally kept closed by a valve. Two thermocouples are placed vertically through the top of the reactor into the bed of silicon or activated silicon particles. One thermocouple is connected to a digital thermometer. The other provides the feedback signal to the heater/controller device. Electrical heating wire and fiberglass insulation are wrapped along the entire length of the reactor. The two ends of the heating wire are connected to the heater/controller device. At its top, the reactor connects to the condensing chamber by a Vycor ® side arm 2.5 cm i.d. and 20 cm long. The condensing chamber is kept at −63° C. to −78° C. with solid carbon dioxide and isopropanol. Condensed samples of the reaction product are withdrawn, usually hourly, into weighed containers. Unreacted organohalide is allowed to distill off at 23° C.-30° C. and the residue analyzed by gc, gc/ms, and/or gc/FTIR.

Reactor B

This was a carbon steel fluidized-bed reactor 183 cm long × 5.08 cm i.d. A sintered metal frit at its base supports the silicon or activated silicon bed and disperses the gaseous reactant as it enters the bed. A flanged carbon steel reservoir, vented with nitrogen, is attached to the reactor near its base just above the frit to permit the intermittent addition of catalyst, promoter, and/or additional silicon or activated silicon to the reactor. The junction of the reservoir and the reactor is normally kept closed by a valve. Two thermocouples are located in the bed of silicon or activated silicon. One provides feedback to the heater/controller device; the other is attached to a digital thermometer. Electrical heaters covered with insulation on the outer surfaces are placed along the full length of the reactor. The heaters are connected to the heater/controller device. A gauge at the top of the reactor measures the reactor pressure. The outlet of the reactor is connected to a carbon steel cyclone which connects downstream to a sintered metal filter. Separation of elutriated solid from the gaseous reactor effluent is accomplished in the cyclone and filter. A back-pressure control valve located downstream of the condenser outlet permits operation of Reactor B at pressures up to 100 psig. Sampling and analysis are performed as described hereinabove for Reactor A.

For both reactors, the gaseous organohalide, hydrogen and nitrogen are conveyed from their respective commercial cylinders to a common reactor inlet through stainless steel tubing. All the gases are separately treated to remove traces of oxygen (e.g. with OXICLEAR ®, Labclear, Oakland, Calif.) and moisture (e.g. with Drierite ® and/or Linde 4A molecular sieve) prior to entry into the reactor. Liquid auxiliary agent (e.g. $CH_3SiCl_3$) is additionally fed into the common inlet by means of a syringe pump, metering pump, or pressurized gas ($N_2$, $H_2$ or organohalide) flow. The common inlet is heated to temperatures well above the boiling point of the auxiliary agent so that a fully gaseous stream enters the reactor. All flowmeters used are calibrated and check valves are provided in the conveying lines to prevent the inadvertent contamination of feed sources. All gas flow rates mentioned in the examples are referred to 21° C. and the stated pressure of the reaction.

EXAMPLE 1

This example illustrates the deleterious effect of zinc on the selectivity to total methylchlorohydrosilanes (MeSiH). Run 1A was carried out without further addition of zinc to the reactants whereas in Run 1B the zinc content was increased by addition of $ZnCO_3$. In both Runs 246.9 g of silicon, Si-1, and 3.1 g of cement copper catalyst, C-4, were mixed in Reactor A and heated to 325° C. under nitrogen fluidization at a nitrogen flow of one liter per minute. Thereafter, hydrogen chloride gas at a flow of one liter per minute was admitted through the base of the reactor for 30 minutes to activate the silicon. A 10° to 20° C. exotherm was observed during that time. During this activation about 1 to 2 weight percent of the silicon was converted to chlorosilanes, principally trichlorosilane, which were removed, condensed, collected and weighed.

Run 1A—Upon termination of the hydrogen chloride flow to activate the silicon, a mixture of 472 ml/min of hydrogen and 1,013 ml/min of methyl chloride (32 vol. % hydrogen) was introduced into the reactor bed through the frit and the reaction continued at 325° C. for 8 hours under fluidization conditions. At the outset the total zinc concentration of the activated silicon was 15.2 ppm; at conclusion of the reaction it was less than 5 ppm.

Run 1B—Upon termination of the hydrogen chloride flow to activate the silicon, 0.5 g of zinc carbonate mixed with 2.8 g of silicon, Si-1, was added to the reactor through the reservoir just prior to the introduction of the hydrogen-methyl chloride mixture. The flow of gaseous mixture was continued for 8 hours at a reaction temperature of 325° C. At the outset of the reaction the total zinc concentration of the activated silicon was 1,046 ppm; at conclusion it was about 70±20 ppm.

In both Runs, samples were collected hourly and, following removal of unreacted methyl chloride, were analyzed by gas chromatography. The average composition of the hourly samples is set forth in Table 5. The data support the following conclusions:

(1) Decreased total zinc concentration in the initial activated silicon caused an increase in the average hourly concentration of methylchlorohydrosilanes (DM+MD) of about 91.4 percent; from 15.1 weight percent in Run 1B to 28.9 percent in Run 1A.

(2) Selectivity to the methylchlorohydrosilanes was greater when the activated silicon contained less than 50 ppm zinc.

(3) Though the higher zinc content in Run 1B was associated with a higher reaction rate of the silicon and formation of larger gross weight of total products mixture over the eight hours reaction period in Run 1B as compared to Run 1A, the suppression of selectivity to total methylchlorohydorsilanes formation was so great in Run 1B that the absolute total weight of methylchlorohydrosilanes of 33.78 g produced in Run 1A far exceeded that of 17.84 g produced in Run 1B.

Runs 2A, 2B, 2C

These were performed in Reactor A and employed 300 gm of silicon Si-5, and a single copper catalyst chosen from the list in Table 3. 7.5 g. of the cement copper catalyst, C-4, was employed in 2A; 7.5 g. of the non-cement copper catalyst, C-5, was used in 2B and 24 g. of the cuprous chloride catalyst, C-1, in 2C. The procedure used for activating the silicon with HCl was that described in Example 1. Reaction was conducted at 325° C. with a mixture of 615.8 ml/min CH$_3$Cl and 653.3 ml/min H$_2$ (51.5 vol. % H$_2$), for eight hours. Sampling and analysis of the reaction product were performed hourly as described in Example 1.

Run 2D

In the experiment of Run 2D, Reactor B was charged with a mixture of 1400 g. of silicon Si-1, 75 g. cuprous chloride C-2, and 1.5 g. SnCl$_2$ and heated to 335° C. under a flow of 2.6 lit/min nitrogen at 1 atm. HCl was then introduced at 2.3 lit/min, 1 atm. for 1 hour, during which period the temperature increased to 348° C. The weight of crude trichlorosilane produced was 360.4 g. After the termination of HCl flow, a mixture of 1.84 lit/min CH$_3$Cl and 1.56 lit/min H$_2$ (46 vol. % H$_2$) was introduced. The gas flows are referred to 30 psig and 21° C. Reaction was continued at 335° C. and 30 psig for twenty hours. An exotherm of 30°-40° C. occurred during the first two hours of reaction. Samples were collected at the intervals shown in Table 8. The samples were analyzed by gas chromatography.

The initial concentrations of Cu, Sn, and Zn in the activated silicon samples of the four experiments are set forth in Table 6. Note the initial Zn concentrations were all less than 50 ppm.

Table 7 shows that the reaction of Run 2A, in which the initial Sn concentration was 29.3 ppm, was significantly less selective to the methylchlorohydrosilanes and afforded more methylchlorodisilanes (HVS) than the reactions of Runs 2B and 2C.

TABLE 6

| Bulk Concentration of Critical Trace Elements and Copper in the Activated Silicon of Runs 2A-2D | | |
|---|---|---|
| Sn | Zn | Cu |

TABLE 5

| | Average of Hourly Compositions of Samples Collected in Runs 1A and 1B | | | | | | | | | |
|---|---|---|---|---|---|---|---|---|---|---|
| Run | DM Wt. % | MD Wt. % | M Wt. % | T Wt. % | D Wt. % | HVS Wt. % | MD/DM | MeSiH Wt. % | MeSiH/D | Rate, % Si/hr[a] |
| 1A | 7.44 ± 1.22 | 21.45 ± 1.79 | 2.87 ± 0.41 | 11.97 ± 1.78 | 55.17 ± 2.52 | 0.58 ± 0.27 | 2.974 ± 0.70 | 28.90 ± 1.57 | 0.53 ± 0.05 | 1.13 ± 0.46 |
| 1B | 6.10 ± 1.92 | 9.01 ± 2.99 | 4.42 ± 0.40 | 7.96 ± 0.82 | 71.48 ± 3.97 | 0.94 ± 0.61 | 1.59 ± 0.51 | 15.10 ± 4.00 | 0.22 ± 0.08 | 1.78 ± 0.46 |

[a]Average rate of silicon reacted per hour.
Note: Each entry in this and subsequent tables should be read as follows:
e.g.
7.44 ± is 7.44 ± 1.22
1.22

EXAMPLE 2

This example illustrates the effect of tin content on the selectivity to methylchlorohydrosilanes (MeSiH).

| Run | (ppm) | (ppm) | (wt. %) |
|---|---|---|---|
| 2A | 29.3 | 24.1 | 1.97 |
| 2B | 3.1 | 1.0 | 2.14 |
| 2C | <1.5 | <7 | 4.94 |
| 2D | 671 | 40 | 3.53 |

TABLE 7

| | Average Hourly Composition of Samples Collected in Runs 2A-2C | | | | | | | | |
|---|---|---|---|---|---|---|---|---|---|
| Run | DM Wt. % | MD Wt. % | M Wt. % | T Wt. % | D Wt. % | HVS Wt. % | MD/DM | MeSiH Wt. % | MeSiH/D | Rate, % Si/hr |
| 2A | 2.52 ± 0.19 | 17.38 ± 1.60 | 2.66 ± 0.49 | 16.05 ± 6.56 | 58.48 ± 9.26 | 3.12 ± 1.27 | 6.59 ± 0.25 | 19.06 ± 0.82 | 0.33 ± 0.06 | 0.27 ± 0.03 |
| 2B | 14.22 ± 0.78 | 39.07 ± 1.35 | 3.04 ± 0.28 | 6.57 ± 0.47 | 36.81 ± 1.52 | 0.21 ± 0.14 | 2.75 ± 0.11 | 53.29 ± 1.96 | 1.45 ± 0.13 | 0.57 ± 0.07 |
| 2C | 12.70 ± 1.89 | 27.64 ± 3.97 | 5.38 ± 0.81 | 6.46 ± 1.45 | 47.66 ± 3.69 | 0.03 ± 0.03 | 2.18 ± 0.06 | 40.33 ± 5.85 | 0.86 ± 0.19 | 0.62 ± 0.12 |

TABLE 8

| | Composition of Cumulative Samples Collected During Run 2D | | | | | | | | |
|---|---|---|---|---|---|---|---|---|---|
| Time (hr) | TC Wt. % | DM Wt. % | MD Wt. % | M Wt. % | T Wt. % | D Wt. % | HVS Wt. % | MeSiH Wt. % | MeSiH/D | Rate, % Si/hr |
| 0-2 | 2.09 | — | 7.52 | 6.64 | 35.10 | 40.52 | 8.13 | 7.52 | 0.19 | 7.58 |
| 2-6 | 0.12 | 0.09 | 7.25 | 2.27 | 24.24 | 57.18 | 8.89 | 7.34 | 0.13 | 3.47 |
| 6-8 | — | — | 5.73 | 2.00 | 25.82 | 54.10 | 12.35 | 5.73 | 0.11 | 2.34 |
| 8-12 | — | 0.24 | 5.93 | 1.79 | 22.91 | 65.51 | 3.62 | 6.17 | 0.09 | 2.03 |
| 12-16 | 0.93 | 0.32 | 7.57 | 2.30 | 22.90 | 59.95 | 4.85 | 7.89 | 0.13 | 1.75 |
| 16-20 | 6.65 | 0.53 | 15.25 | 1.04 | 30.73 | 44.54 | 1.27 | 15.78 | 0.35 | 1.22 |

Table 8 sets forth the composition of the cumulative samples collected periodically during the 20 hour reaction of Run 2D. The data show that a steady-state rate and composition were not established during the twenty hour reaction. The high Sn concentration in the activated silicon caused very low selectivity (MeSiH and MeSiH/D) to the methylchlorohydrosilanes and considerable formation of methychlorodisilanes (HVS) and methyltrichlorosilane (T).

Taken together, the four runs of this example show that the total concentration (MeSiH) of methylchlorohydrosilanes in the product mixture can exceed 50 wt. % and the ratio, MeSiH/D, can be greater than 1.0 when the Sn concentration in the activated silicon is less than 10 pm and the Zn is less than 50 ppm and preferably less than 20 ppm.

EXAMPLE 3

This example illustrates the benefits to the reaction rate and on the selectivity to methylchlorohydrosilanes (MeSiH) of employing silicon containing 40-100 ppm nickel distributed throughout all the particles in the activated silicon.

Runs 3A, 3B, 3C

Three different silicon samples (Si-1, Si-4, Si-5) were used in the three separate runs summarized in this example; Reactor B was used for all three. The quantities of silicon and catalyst used in the experiments are set forth in Table 9. The table also shows the reaction temperature, pressure, hydrogen, and methyl chloride flow rates, the duration of each experiment, and the concentrations of Cu, Sn, Zn, and Ni initially present in the activated silicon.

Activation of the silicon and catalyst mixture was performed with gaseous HCl as described in Run 2D, except that the duration of HCl flow was 60 min. in Run 3A and 30 min. in each of Runs 3B and 3C.

Table 10 sets forth the total weights of crude (i.e., product still containing dissolved methyl chloride) product mixture obtained in each run, the composition of each product mixure adjusted for methyl chloride content, and the rate and selectivity parameters of the syntheses.

The data show that nickel concentrations from about 10-100 ppm in the activated silicon afford high selectivity to the methylchlorohydrosilanes. The MeSiH/D ratio was greater than 1.0 and MeSiH was greater than 50 wt. % in each of the three runs of this Example. However, comparing the rate in Run 3A, wherein the initial nickel concentration of the silicon particles was 16 ppm, with the rates in Runs 3B and 3C, wherein the initial nickel concentrations were 53 ppm and 83 ppm, respectively, shows that rates are higher at nickel concentrations from about 40 to 100 ppm. Additionally, the nickel promoter in the silicon samples Si-4 and Si-5 must have been present in a catalytically effective state.

TABLE 9

| | Reaction Conditions and Activated Mass Composition in the Runs 3A-3C | | | | | | | | | |
|---|---|---|---|---|---|---|---|---|---|---|
| Run | Si | Catalyst | Temp. °C. | Press. psig | H₂ lit/min | CH₃Cl lit/min | Duration Hr. | Cu wt % | Sn ppm | Zn ppm | Ni ppm |
| 3A | 1492.4 g Si-1 | 74.6 g C-2 | 315 ± 3 | 30 | 1.57 | 1.00 | 4 | 3.3 | <5 | 41 | 16 |
| 3B | 1382.0 g Si-5 | 73 g C-1 | 307 ± 3 | 30 | 2.03 | 1.19 | 8 | 3.0 | <5 | 7 | 53 |
| 3C | 900 g Si-4 | 45 g C-6 | 312 ± 2 | 30 | 2.17 | 2.17 | 8 | 3.3 | <3 | 18 | 83 |

TABLE 10

| | Composition of the Reaction Products of Runs 3A-3C | | | | | | | | | |
|---|---|---|---|---|---|---|---|---|---|---|
| Run | Vol. % H₂ | Weight of Crude (g) | TC wt. % | DM wt. % | MD wt. % | M wt. % | T wt. % | D wt. % | MD/DM | MeSiH wt. % | MeSiH/D | Rate, % Si/hr |
| 3A | 61.1 | 81.3 | 0.11 | 16.26 | 43.52 | 3.37 | 5.70 | 31.03 | 2.68 | 59.78 | 1.93 | 0.32 |
| 3B | 63.0 | 554 | 3.34 | 14.82 | 50.50 | 1.59 | 12.42 | 17.43 | 3.41 | 65.32 | 3.77 | 1.96 |

TABLE 10-continued

| | | | Composition of the Reaction Products of Runs 3A-3C | | | | | | | | |
|---|---|---|---|---|---|---|---|---|---|---|---|
| Run | Vol. % H$_2$ | Weight of Crude (g) | TC wt. % | DM wt. % | MD wt. % | M wt. % | T wt. % | D wt. % | MD/DM | MeSiH wt. % | MeSiH/D | Rate, % Si/hr |
| 3C | 50.0 | 356.6 | 1.55 | 16.84 | 37.96 | 4.68 | 9.16 | 29.81 | 2.25 | 54.80 | 1.84 | 1.30 |

EXAMPLE 4

This example shows that a silicon sample with inherently low or inactive nickel content (and thereby low reactivity in the Direct Synthesis of methylchlorohydrosilanes, MeSiH) can be promoted to react at faster sustained rates by adding nickel powder to maintain effective nickel concentrations within the activated silicon. This sample also illustrates the effects of nickel addition on the composition of the reaction product.

The three runs of this example were performed separately in Reactor B.

Run 4A: Silicon sample, Si-1, was used in this example. It was shown in Run 3A (Tables 9 and 10) that this silicon contained an inherently low level of nickel.

A mixture of 900 g of silicon, Si-1, and 45.1 gm cuprous chloride catalyst, C-6, was heated to 330° C. under nitrogen fluidization and then activated with 2.3 l/min gaseous HCl for 30 min. as described in Run 2D. During the activation, 9.0 g nickel powder (1 micron particle size from Alpha Inorganics, Andover, Mass.; Lot #100675) mixed with 30 g of silicon, Si-1, was added to the reactor. Following the termination of HCl flow, hydrogen at 2.2 lit/min for 30 min. was used to desorb chlorosilanes from the activated silicon.

For the reaction, both CH$_3$Cl and H$_2$ were set at 1.25 lit/min, the reaction pressure was set at 30 psig, and the temperature at 280° C. Samples were collected hourly for five hours. Thereafter the reaction temperature was increased to 310° C. and reaction continued at the above-mentioned conditions. After two hours, a mixture of 9 nickel powder and 30 g Si-1 was again charged through the reservoir into the reactor and the reaction performance monitored for another five hours.

Table 11 sets forth the composition, the rate and the selectivity parameters for the hourly samples taken during the experiment. The data show that the initial reaction rate (0.77% Si per hour) of the activated mass made with Si-1 and exogenously derived nickel was higher than that observed in Run 3A, despite the 35° C. lower temperature in Run 4A. The data also show that this initially higher rate deteriorated to very low levels in the absence of further nickel additions. The rate increase during 6-7 hours was brought about by the temperature increase to 310° C. A second nickel addition (equivalent to 1 wt. % based on silicon in the reactor) made after the seventh hour caused the reaction rate to increase to 1% Si per hour at the eighth hour. However, as the declining rates for 9-12 hours show, this rate increase was only temporary. Consequently, the effect of exogenously derived nickel is short lived unless the addition is made frequently or continuously so as to maintain both an effective chemical form of nickel and an effective nickel concentration in the activated silicon.

TABLE 11

| | | | Composition of Samples and Performance Parameters for Run 4A | | | | | | | | |
|---|---|---|---|---|---|---|---|---|---|---|---|
| Time (hr) | TC Wt. % | DM Wt. % | MD Wt. % | M Wt. % | T Wt. % | D Wt. % | MD/DM | MeSiH Wt. % | MeSiH/D | Rate, % Si/hr |
| 1 | 3.64 | 9.41 | 50.26 | 1.61 | 8.79 | 26.29 | 5.34 | 59.67 | 2.27 | 0.77 |
| 2 | 1.00 | 8.61 | 57.49 | 2.49 | 11.81 | 18.60 | 6.68 | 66.10 | 3.55 | 0.22 |
| 3 | 0.99 | 10.04 | 54.48 | 1.84 | 13.64 | 19.01 | 5.43 | 64.52 | 3.39 | 0.18 |
| 4 | 0.98 | 9.31 | 54.19 | 2.11 | 13.61 | 19.80 | 5.82 | 63.50 | 3.21 | 0.17 |
| 5 | 0.91 | 10.87 | 51.54 | 1.50 | 14.63 | 20.55 | 4.74 | 62.41 | 3.04 | 0.16 |
| 6$^a$ | 0.34 | 13.87 | 59.15 | 1.17 | 9.63 | 15.84 | 4.27 | 73.02 | 4.61 | 0.54 |
| 7 | 0.46 | 11.56 | 60.84 | 1.44 | 9.84 | 15.86 | 5.26 | 72.40 | 4.57 | 0.52 |
| 8$^b$ | 1.83 | 8.74 | 44.33 | 0.77 | 13.09 | 31.14 | 5.07 | 53.07 | 1.70 | 1.40 |
| 9 | 3.23 | 8.38 | 53.09 | 0355 | 11.71 | 23.04 | 6.34 | 61.47 | 2.67 | 0.61 |
| 10 | 4.23 | 8.50 | 56.82 | 0.69 | 11.52 | 18.24 | 6.69 | 65.32 | 3.58 | 0.42 |
| 11 | 3.55 | 7.76 | 57.12 | 0.93 | 12.10 | 18.54 | 7.36 | 64.88 | 3.50 | 0.04 |
| 12 | 3.63 | 8.06 | 56.33 | 0.94 | 13.07 | 17.97 | 6.99 | 64.39 | 3.58 | 03.4 |

$^a$Temperature raised to 310° C.
$^b$Nickel added

Run 4B: The experiment of this example was conducted by continuing the experiment of Run 3C beyond eight hours. Additions of 9.1-9.6 g nickel powder in 60 g of silicon, Si-4, were made at the beginning of the ninth hour, the seventeenth hour, and the twenty-fourth hour. Reaction was continued at 310°-320° C. and 30 psig with 2.17 lit/min CH$_3$Cl and 2.17 lit/min H$_2$ until twenty-one hours had elapsed. At the end of that time a sample of the cooled activated silicon was taken for nickel analysis.

Table 12 sets forth the composition of the hourly samples collected and the performance parameters (i.e. rate, selectivity) appertaining thereto. It is observed that following the addition of 9.1 g nickel to the reactor at the ninth hour and seventeenth hour and 9.6 g nickel at the twenty-fourth hour the reaction rate increased to values (1.6-2.6% Si per hour) beyond those reported in Example 3C. However, each rate increase was temporary as seen in the data for the periods 13-16 hours, 21-23 hours, and 28-29 hours. The experiment showed that the temporary rate increase caused by exogenous nickel seen with a silicon sample, Si-1, inherently deficient in nickel, was also observed with silicon sample Si-4 containing an inherently effective level of nickel. It is clear that a principal effect of exogenous nickel is a rate increase.

The nickel concentration of the activated silicon after reaction was found by analysis to be 0.318 wt %. However, at the twenty-eighth hour, the reaction rate had declined to less than 1% Si per hour. Consequently, this result shows that it is not sufficient to have nickel concentration in the activated silicon greater than 0.1 wt % in order to observe increased reaction rates. The nickel must also be present in a catalytically effective form, preferably, as in Example 3, distributed throughout all the activated silicon particles for best results.

a steady-state rate of 1.25±0.07 wt % Si per hour at 315°±4° C.

The composition of the reaction product also responded to the addition of Ni powder. Methyltri-

TABLE 12

Composition of Samples and Performance Parameters for Run 4B

| Time (hr) | TC Wt. % | DM Wt. % | MD Wt. % | M Wt. % | T Wt. % | D Wt. % | MD/DM | MeSiH Wt. % | MeSiH/D | Rate, % Si/hr |
|---|---|---|---|---|---|---|---|---|---|---|
| 9[a] | 1.20 | 12.50 | 20.07 | 2.09 | 16.45 | 47.69 | 1.61 | 32.57 | 0.68 | 1.12 |
| 10 | 0.74 | 16.34 | 28.59 | 2.99 | 12.07 | 39.27 | 1.75 | 44.93 | 1.14 | 1.77 |
| 11 | 0.28 | 17.62 | 30.68 | 3.31 | 10.94 | 37.17 | 1.74 | 48.30 | 1.30 | 1.57 |
| 12 | 0.83 | 13.72 | 37.09 | 3.63 | 9.42 | 35.31 | 2.70 | 50.81 | 1.61 | 1.53 |
| 13 | 1.31 | 16.05 | 39.13 | 3.32 | 8.57 | 31.62 | 2.44 | 55.18 | 1.75 | 0.99 |
| 14 | 1.12 | 13.69 | 39.82 | 3.36 | 9.39 | 32.62 | 2.91 | 53.51 | 1.64 | 1.06 |
| 15 | 1.56 | 17.54 | 39.83 | 2.97 | 8.83 | 29.27 | 2.27 | 57.37 | 1.96 | 0.96 |
| 16 | 1.78 | 16.33 | 39.76 | 3.62 | 9.25 | 29.96 | 2.44 | 56.09 | 1.92 | 0.60 |
| 17[a] | 0.58 | 11.23 | 21.42 | 2.29 | 18.70 | 45.78 | 1.91 | 32.65 | 0.71 | 2.42 |
| 18 | 1.31 | 14.50 | 31.01 | 2.77 | 13.64 | 36.77 | 2.14 | 45.51 | 1.24 | 2.04 |
| 19 | 2.05 | 14.78 | 31.99 | 2.34 | 13.77 | 35.07 | 2.16 | 46.77 | 1.33 | 1.44 |
| 20 | 2.24 | 14.87 | 33.34 | 2.46 | 13.67 | 33.42 | 2.24 | 28.21 | 1.44 | 1.30 |
| 21 | 2.33 | 15.63 | 35.26 | 2.04 | 13.34 | 31.40 | 2.26 | 50.89 | 1.62 | 0.93 |
| 22 | 2.46 | 16.09 | 36.45 | 1.97 | 12.86 | 30.17 | 2.27 | 52.54 | 1.74 | 0.81 |
| 23 | 2.29 | 16.48 | 39.22 | 2.28 | 11.62 | 28.11 | 2.38 | 55.70 | 1.98 | 0.63 |
| 24[b] | 0.88 | 9.22 | 19.80 | 1.73 | 23.72 | 44.63 | 2.15 | 29.02 | 0.65 | 2.32 |
| 25 | 1.46 | 12.47 | 30.28 | 2.05 | 17.41 | 36.33 | 2.43 | 42.75 | 1.18 | 2.33 |
| 26 | 2.00 | 12.71 | 33.16 | 1.84 | 17.06 | 33.23 | 2.61 | 45.87 | 1.38 | 1.65 |
| 27 | 2.18 | 12.40 | 33.96 | 1.70 | 17.65 | 32.11 | 2.74 | 46.36 | 1.44 | 1.15 |
| 28 | 2.11 | 12.86 | 36.65 | 1.66 | 16.92 | 29.80 | 2.85 | 49.51 | 1.66 | 0.82 |
| 29 | 2.03 | 13.39 | 39.29 | 1.65 | 15.93 | 27.71 | 2.93 | 52.68 | 1.90 | 0.65 |

[a] 9.1 g. Ni added
[b] 9.6 g. Ni added

Run 4C: The experiment of this example was performed at 310°-332°, 30 psig using 1.42 lit/min $H_2$ and 1.44 lit/min $CH_3Cl$. The activated silicon was prepared from 900 g silicon, Si-4, 45.0 g cuprous chloride, C-6, and 0.9 g nickel powder (1 micron particle size, Alfa Inorganics, Lot #100675) and gaseous HCl at 330°-343° C. as described in Run 2D. HCl activation was continued for 30 min. Thereafter, hydrogen at 2.4 lit/min, 0 psig, was introduced for 30 min. to desorb chlorosilanes from the activated silicon particles. The hydrogen-methyl chloride mixture was then injected. The initial reaction temperature was 330° C.

Except as noted in Table 13, hourly additions of nickel powder mixed with silicon, Si-4, were made to the reactor in order to maintain the catalytically active nickel at an effective level and prevent the rate decreases observed in Runs 4A and 4B. The quantities of solid added are recorded in Table 13. Also shown in Table 13 are the average hourly temperatures, the hourly weights of crude reaction product, and the weight of silicon calculated to be in the reactor at the beginning of each hour. The reaction was continued for a total of twenty-nine hours, at the end of which a cooled sample of the activated silicon was analyzed and found to contain 0.203 wt % Ni.

Table 14 sets forth the composition of the hourly samples as well as the rate and selectivity values for each sample. The data show that the frequent additions of nickel powder led to steady and exceptionally high reaction rates in comparison with those observed in Runs 4A and 4B. Maintaining the nickel addition at 0.1 wt % of the activated silicon contained in the reactor afforded rates as high as 3.34 wt % Si per hour at 330°±2° C. The steady-state average was 2.64±0.34 wt % Si per hour. At 320°±4° C., the steady-state rate was 1.40±0.18 wt % Si per hour with nickel additions equivalent to 0.05 wt % of the activated silicon. Nickel additions of 0.24 wt % of the activated silicon afforded chlorosilane and dimethyldichlorosilane increased in the hourly samples immediately following Ni addition. (See Table 11, sample 8; Table 12, samples 17, 24). The higher levels of nickel employed during 24–29 hours of Run 4C (see Table 13) also resulted in increased methyltrichlorosilane formation during that period (see Table 14) relative to the earlier part of the experiment. Consequently, nickel addition reduced the percentage of methylchlorohydrosilanes in the reaction product and also the ratio, MeSiH/D. (See Table 11, sample 8; Table 12, samples 17, 24). Accordingly, it is necessary to regulate the addition of nickel in order to obtain the rate benefits, minimize methyltrichlorosilane formation, and maintain selectivity to the methylchlorohydrosilanes within desirable limits. It is preferable to add nickel continuously or intermittently at values in the range 0.01–0.25 wt % of the activated silicon in the reactor to satisfy these objectives.

TABLE 13

Reaction Conditions During Run 4C

| Time (hr) | Temp, °C. | Si Added gm | Ni Added gm | Crude Product gm | Si in Reactor gm |
|---|---|---|---|---|---|
| 1 | 330 | — | 0.9 | 66.8 | 872.19 |
| 2 | 333 | 50.6 | 0.9 | 102.7 | 908.51 |
| 3 | 331 | 15.0 | 0.9 | 123.0 | 901.90 |
| 4 | 332 | 10.0 | 1.0 | 115.7 | 885.76 |
| 5 | 331 | 10.8 | 0.9 | 118.4 | 871.66 |
| 6 | 329 | 60.0 | 0.9 | 145.2 | 906.60 |
| 7 | 328 | 20.4 | 0.9 | 110.8 | 896.76 |
| 8 | 328 | 25.4 | 0.9 | 110.3 | 898.40 |
| 9 | 330 | 18.4 | 0.9 | 105.1 | 893.96 |
| 10 | 330 | 25.5 | 0.9 | 104.4 | 897.33 |
| 11 | 329 | 30.0 | 0.9 | 98.2 | 905.47 |
| 12 | 327 | 31.0 | 0.9 | 94.3 | 915.82 |
| 13 | 328 | 30.6 | 0.9 | 84.6 | 926.17 |
| 14 | 326 | 0 | 0 | 46.3 | 908.12 |
| 15 | 325 | 0 | 0 | 66.8 | 898.33 |
| 16 | 318 | 0 | 0 | 58.1 | 884.09 |
| 17 | 323 | 42.5 | 0.45 | 71.0 | 914.35 |
| 18 | 320 | 15.0 | 0.45 | 64.8 | 914.44 |
| 19 | 320 | 10.1 | 0.45 | 54.4 | 910.74 |

TABLE 13-continued

| | Reaction Conditions During Run 4C | | | |
|---|---|---|---|---|
| Time (hr) | Temp, °C. | Si Added gm | Ni Added gm | Crude Product gm | Si in Reactor gm |
| 20 | 317 | 20.5 | 0.45 | 50.7 | 919.50 |
| 21 | 318 | 20.1 | 0.45 | 51.2 | 928.66 |
| 22 | 311 | 0 | 0 | 31.2 | 917.65 |
| 23 | 307 | 0 | 0 | 39.1 | 911.08 |
| 24 | 314 | 26.2 | 2.25 | 52.9 | 928.99 |
| 25 | 314 | 19.0 | 2.25 | 54.5 | 937.70 |
| 26 | 317 | 15.0 | 2.25 | 55.5 | 940.97 |
| 27 | 318 | 20.0 | 2.25 | 59.1 | 949.45 |
| 28 | 319 | 15.1 | 2.25 | 61.0 | 952.25 |
| 29 | 318 | 10.0 | 2.25 | 57.4 | 949.56 |

TABLE 14

Composition of Samples and Performance Parameters for Run 4C

| Time (hr) | TC Wt. % | DM Wt. % | MD Wt. % | M Wt. % | T Wt. % | D Wt. % | MD/DM | MeSiH Wt. % | MeSiH/D | Rate, % Si/hr |
|---|---|---|---|---|---|---|---|---|---|---|
| 1 | 5.70 | 10.43 | 35.05 | 4.54 | 12.23 | 32.05 | 45.48 | 3.36 | 1.42 | 1.64 |
| 2 | 3.18 | 10.74 | 31.39 | 5.42 | 11.66 | 37.61 | 42.13 | 2.92 | 1.12 | 2.38 |
| 3 | 2.46 | 12.44 | 32.32 | 5.08 | 10.23 | 37.47 | 44.76 | 2.60 | 1.20 | 2.90 |
| 4 | 2.10 | 13.78 | 31.94 | 4.60 | 10.06 | 37.52 | 45.72 | 2.32 | 1.22 | 2.81 |
| 5 | 1.85 | 14.34 | 30.88 | 4.13 | 9.75 | 39.05 | 45.22 | 2.15 | 1.16 | 2.94 |
| 6 | 1.84 | 14.69 | 27.85 | 3.28 | 12.46 | 39.88 | 42.51 | 1.90 | 1.07 | 3.34 |
| 7 | 1.38 | 14.93 | 28.70 | 3.37 | 10.97 | 40.65 | 43.63 | 1.92 | 1.07 | 2.65 |
| 8 | 2.44 | 14.23 | 29.96 | 3.78 | 10.74 | 38.85 | 44.19 | 2.11 | 1.14 | 2.57 |
| 9 | 2.38 | 15.30 | 30.60 | 3.28 | 10.89 | 37.55 | 45.90 | 2.00 | 1.22 | 2.45 |
| 10 | 2.49 | 14.02 | 31.23 | 3.35 | 10.63 | 38.28 | 45.25 | 2.23 | 1.18 | 2.44 |
| 11 | 2.48 | 14.74 | 31.42 | 2.95 | 11.42 | 36.99 | 46.16 | 2.13 | 1.25 | 2.28 |
| 12 | 2.37 | 14.34 | 32.20 | 2.76 | 11.50 | 36.83 | 46.54 | 2.25 | 1.26 | 2.21 |
| 13 | 2.78 | 14.37 | 32.02 | 2.81 | 12.33 | 35.69 | 46.39 | 2.23 | 1.30 | 1.95 |
| 14 | 3.39 | 11.68 | 28.73 | 2.07 | 15.94 | 38.19 | 40.41 | 2.46 | 1.06 | 1.08 |
| 15 | 2.45 | 14.60 | 31.25 | 2.68 | 13.93 | 35.09 | 45.85 | 2.14 | 1.31 | 1.59 |
| 16 | 2.97 | 15.97 | 33.14 | 2.36 | 11.95 | 33.61 | 49.11 | 2.08 | 1.46 | 1.38 |
| 17 | 3.14 | 15.05 | 36.57 | 2.16 | 14.83 | 28.25 | 51.62 | 2.43 | 1.83 | 1.63 |
| 18 | 3.12 | 16.45 | 40.18 | 1.81 | 14.26 | 24.18 | 56.63 | 2.44 | 2.34 | 1.51 |
| 19 | 3.11 | 16.18 | 40.48 | 1.78 | 13.92 | 24.53 | 56.66 | 2.50 | 2.31 | 1.29 |
| 20 | 2.86 | 16.00 | 39.87 | 1.77 | 13.85 | 25.65 | 55.87 | 2.49 | 2.18 | 1.19 |
| 21 | 2.66 | 15.67 | 39.13 | 1.77 | 14.35 | 26.42 | 54.80 | 2.50 | 2.07 | 1.19 |
| 22 | 4.47 | 13.26 | 35.70 | 1.16 | 15.73 | 29.68 | 48.96 | 2.69 | 1.65 | 0.72 |
| 23 | 2.72 | 15.86 | 38.54 | 1.64 | 13.89 | 27.35 | 54.40 | 2.43 | 1.99 | 0.91 |
| 24 | 3.81 | 14.47 | 36.50 | 1.33 | 18.10 | 25.79 | 50.97 | 2.52 | 1.98 | 1.15 |
| 25 | 2.39 | 13.68 | 36.66 | 0.94 | 19.13 | 27.20 | 50.34 | 2.68 | 1.85 | 1.21 |
| 26 | 2.72 | 13.55 | 36.77 | 0.87 | 19.08 | 27.01 | 50.32 | 2.71 | 1.86 | 1.22 |
| 27 | 2.76 | 13.31 | 37.24 | 1.23 | 18.63 | 26.83 | 50.55 | 2.80 | 1.88 | 1.30 |
| 28 | 2.54 | 12.55 | 35.64 | 1.33 | 19.93 | 28.01 | 48.19 | 2.84 | 1.72 | 1.33 |
| 29 | 2.44 | 13.69 | 38.51 | 1.35 | 17.22 | 26.79 | 52.20 | 2.81 | 1.95 | 1.28 |

EXAMPLE 5

This example shows that selectivity to the methylchlorohydrosilanes (MeSiH) is lower when nickel formate, rather than nickel powder, is used as the source of nickel promoter. Concurrently, the use of nickel formate results in higher methyltrichlorosilane formation. Two separate experiments are summarized in this example. Both experiments were performed in Reactor B.

Run 5A: A mixture of 42.5 g cuprous chloride catalyst, C-2, and 850 g of Si-3 was heated to 320° C. under nitrogen (2.5 lit/min, 1 atm.) fluidization. Hydrogen chloride gas (2.5 lit/min, 1 atm.) was then introduced for 30 min. The total weight of chlorosilanes collected was 108.6 g.

Reaction was performed with a mixture of 1.4 lit/min hydrogen and 1.4 lit/min methyl chloride at 325° ±2° C., 30 psig. During the reaction, quantities of nickel powder and silicon, Si-3, were added at hourly intervals. The amounts so added are shown in Table 15. The reaction product was collected hourly and analyzed by gas chromarography after the evaporation of unreacted methyl chloride. Reaction was continued for twenty-one hours altogether.

Table 16 sets forth the composition of the hourly samples and the pertinent rate and selectivity values. It is noteworthy that the activated silicon made from the silicon sample Si-3 and catalyst C-2 was unreactive to the 50 vol. % methyl chloride-hydrogen at 325°-330° C., 30 psig, in the absence of added nickel powder. The data of Table 16 show that with the addition of 0.1-1 wt % nickel powder that the total concentration of methylchlorohydrosilanes in the hourly reaction product was generally greater than fifty weight percent, that the ratio, MeSiH/D, was generally greater than 2 and that the concentration of methyltrichlorosilane was generally less than twenty weight percent. Addition of 0.1-0.2 wt % nickel powder in Run 5A (samples 7-10, Table 16) afforded the highest selectivity to the methylchlorohydrosilanes.

TABLE 15

| | Run 5A | | | | Run 5B | | | |
|---|---|---|---|---|---|---|---|---|
| Time (hr) | Si Added (gm) | Ni Powder Added (gm) | Si in Reactor (gm) | Ni Added (wt. %) | Si Added | Ni (OOCH)$_2$ Added (gm) | Si in Reactor (gm) | Ni Added (wt. %) |
| 1 | — | — | 824.48 | — | — | — | 766.73 | — |
| 2 | 40 | 0.85 | 859.19 | 0.099 | 25 | 2.5 | 785.36 | 0.10 |
| 3 | 17 | 0.85 | 873.17 | 0.097 | 20 | 2.5 | 801.50 | 0.099 |
| 4 | 14.3 | 0.90 | 884.31 | 0.10 | 20 | 2.5 | 818.33 | 0.096 |
| 5 | 15 | 0.9 | 895.56 | 0.10 | 14.3 | 2.5 | 829.03 | 0.095 |
| 6 | 0 | 0.9 | 891.58 | 0.10 | 10.5 | 2.5 | 836.04 | 0.095 |

TABLE 15-continued

| | Run 5A | | | | Run 5B | | | |
|---|---|---|---|---|---|---|---|---|
| Time (hr) | Si Added (gm) | Ni Powder Added (gm) | Si in Reactor (gm) | Ni Added (wt. %) | Si Added | Ni (OOCH)$_2$ Added (gm) | Si in Reactor (gm) | Ni Added (wt. %) |
| 7 | 14.1 | 1.3 | 900.98 | 0.14 | 11.0 | 2.5 | 844.25 | 0.094 |
| 8 | 10.4 | 1.7 | 906.87 | 0.19 | 20.4 | 5.1 | 862.09 | 0.19 |
| 9 | 10.6 | 1.7 | 913.89 | 0.19 | 12.5 | 5.3 | 867.83 | 0.19 |
| 10 | 10.6 | 1.7 | 919.82 | 0.18 | 12.1 | 5.0 | 869.61 | 0.18 |
| 11 | 11.2 | 4.2 | 925.56 | 0.45 | 10.1 | 5.0 | 868.73 | 0.18 |
| 12 | 10.4 | 4.2 | 929.44 | 0.45 | 10.1 | 5.0 | 867.88 | 0.18 |
| 13 | 10.8 | 4.3 | 934.16 | 0.45 | 13.3 | 5.5 | 871.55 | 0.20 |
| 14 | 11.2 | 4.2 | 937.97 | 0.45 | | | | |
| 15 | 30.1 | 9.5 | 960.60 | 0.99 | | | | |
| 16 | 0 | 0 | 951.04 | 0 | | | | |
| 17 | 0 | 0 | 942.78 | 0 | | | | |
| 18 | 0 | 0 | 935.80 | 0 | | | | |
| 19 | 0 | 0 | 928.17 | 0 | | | | |
| 20 | 0 | 0 | 922.17 | 0 | | | | |
| 21 | 0 | 0 | 917.08 | 0 | | | | |

TABLE 16

Composition of Hourly Samples in Run 5A

| Time (hr) | TC Wt. % | DM Wt. % | MD Wt. % | M Wt. % | T Wt. % | D Wt. % | MeSiH Wt. % | MD/DM | MeSiH/D | Rate, % Si/hr |
|---|---|---|---|---|---|---|---|---|---|---|
| 1 | 34.03 | 5.51 | 37.55 | 1.75 | 6.59 | 14.57 | 43.06 | 6.82 | 2.96 | 0.63 |
| 2 | 18.92 | 9.13 | 42.30 | 1.61 | 12.54 | 15.50 | 51.43 | 4.63 | 3.32 | 0.35 |
| 3 | 18.85 | 9.40 | 42.70 | 1.29 | 12.50 | 15.26 | 52.10 | 4.54 | 3.41 | 0.36 |
| 4 | 17.35 | 9.18 | 42.37 | 1.71 | 12.18 | 17.21 | 51.55 | 4.62 | 3.00 | 0.39 |
| 5 | 14.85 | 9.35 | 41.72 | 1.79 | 12.38 | 19.91 | 51.07 | 4.46 | 2.57 | 0.44 |
| 6 | 11.67 | 10.38 | 43.20 | 1.85 | 11.99 | 20.91 | 53.58 | 4.16 | 2.56 | 0.53 |
| 7 | 4.45 | 15.74 | 46.26 | 1.62 | 11.87 | 20.06 | 62.00 | 2.94 | 3.09 | 0.50 |
| 8 | 5.11 | 14.08 | 45.31 | 1.72 | 13.90 | 19.88 | 59.39 | 3.99 | 2.99 | 0.39 |
| 9 | 3.85 | 13.58 | 45.29 | 1.60 | 14.27 | 21.41 | 58.87 | 3.34 | 2.75 | 0.51 |
| 10 | 5.17 | 13.57 | 45.59 | 1.90 | 12.82 | 20.95 | 59.19 | 3.36 | 2.82 | 0.59 |
| 11 | 6.00 | 11.42 | 40.44 | 1.70 | 15.79 | 24.65 | 51.86 | 3.54 | 2.10 | 0.71 |
| 12 | 5.60 | 10.65 | 38.74 | 1.69 | 16.71 | 26.61 | 49.39 | 3.64 | 1.86 | 0.65 |
| 13 | 7.93 | 9.73 | 36.49 | 1.33 | 18.82 | 28.71 | 46.22 | 3.75 | 1.61 | 0.79 |
| 14 | 4.32 | 9.36 | 35.51 | 1.43 | 19.36 | 30.02 | 44.87 | 3.79 | 1.50 | 0.80 |
| 15 | 2.10 | 11.01 | 30.67 | 1.24 | 20.27 | 34.71 | 41.68 | 2.79 | 1.20 | 1.00 |
| 16 | 2.76 | 12.87 | 98.75 | 1.37 | 17.06 | 27.19 | 51.62 | 3.01 | 1.90 | 0.87 |
| 17 | 3.87 | 13.85 | 41.46 | 1.47 | 15.23 | 24.12 | 55.31 | 2.99 | 2.29 | 0.74 |
| 18 | 4.59 | 13.21 | 41.81 | 1.39 | 15.67 | 23.33 | 55.02 | 3.17 | 2.36 | 0.82 |
| 19 | 4.69 | 13.12 | 41.65 | 1.74 | 15.11 | 23.69 | 54.77 | 3.18 | 2.31 | 0.65 |
| 20 | 5.53 | 13.61 | 41.98 | 1.56 | 15.51 | 21.81 | 55.59 | 3.09 | 2.55 | 0.55 |
| 21 | 5.53 | 13.11 | 41.82 | 1.59 | 16.10 | 22.05 | 54.93 | 3.19 | 2.49 | 0.47 |

Run 5B: Anhydrous nickel formate (Ni(OOCH)$_2$) for use in the experiment of this example was prepared from nickel carbonate and formic acid according to the procedure of Bircumshaw and Edwards (Jour. Chem. Soc., p. 1800 (1950)). Dehydration was achieved by washing the green precipitate with acetone and drying it in vacuo (10$^{-5}$ torr) for 16 hours. Chemical analysis of the dried solid showed 31.60 wt % Ni. The nickel content calculated for the formula Ni(OOCH)$_2$ is 31.77%.

The activated silicon of this run was made by heating a mixture of 800 g silicon, Si-3, and 40.9 g cuprous chloride, C-2, under nitrogen (2.5 lit/min, 1 atm.) fluidization to 325° C. and then substituting HCl (2.5 lit/min, 1 atm) for nitrogen. HCl flow was continued for 30 min. The weight of chlorosilanes collected was 160.4 g.

Reaction was performed with a mixture of 1.4 lit/min hydrogen and 1.4 lit/min methyl chloride at 325°±2° C., 30 psig, for thirteen hours. Quantities of anhydrous nickel formate and 65×150 mesh silicon, Si-3, added to the reactor at hourly intervals are recorded in Table 15. Hourly samples were collected and analyzed as described above in Example 5A.

Table 17 sets forth the composition, selectivities and rate of each hourly sample. During 1-7 hours, the nickel additions were 0.1 wt % of the silicon contained in the reactor and 0.2 wt % thereafter, i.e. 7-13 hours. The data show that the MeSiH and MeSiH/D values of Table 17 are generally lower than those of 1-10 hours of Table 16. The use of nickel formate also resulted in lower (CH$_3$)$_2$SiHCl (DM) and higher CH$_3$SiCl$_3$ (T) than observed with the same equivalent weight of nickel powder. In fact, the CH$_3$SiCl$_3$ concentration in the hourly samples of Table 17 was generally above twenty weight percent.

TABLE 17

Composition of Hourly Samples in Run 5B

| Time (hr) | TC Wt. % | DM Wt. % | MD Wt. % | M Wt. % | T Wt. % | D Wt. % | MeSiH Wt/ % | MD/DM | MeSiH/D | Rate, % Si/hr |
|---|---|---|---|---|---|---|---|---|---|---|
| 1 | 30.20 | 2.75 | 22.49 | 2.69 | 8.12 | 33.75 | 25.24 | 8.18 | 0.75 | 0.83 |
| 2 | 23.94 | 3.34 | 30.30 | 1.20 | 20.25 | 20.97 | 33.64 | 9.07 | 1.60 | 0.49 |
| 3 | 26.22 | 3.39 | 27.16 | 1.04 | 28.83 | 18.36 | 30.55 | 8.01 | 1.66 | 0.40 |
| 4 | 24.54 | 3.98 | 27.22 | 1.06 | 24.08 | 19.12 | 31.20 | 6.84 | 1.63 | 0.44 |
| 5 | 21.30 | 4.58 | 27.27 | 1.15 | 24.45 | 21.25 | 31.85 | 5.95 | 1.50 | 0.42 |

TABLE 17-continued

Composition of Hourly Samples in Run 5B

| Time (hr) | TC Wt. % | DM Wt. % | MD Wt. % | M Wt. % | T Wt. % | D Wt. % | MeSiH Wt/ % | MD/DM | MeSiH/D | Rate, % Si/hr |
|---|---|---|---|---|---|---|---|---|---|---|
| 6 | 15.51 | 5.54 | 27.74 | 1.48 | 25.93 | 23.80 | 33.28 | 5.01 | 1.40 | 0.33 |
| 7 | 15.64 | 4.83 | 26.55 | 1.32 | 26.28 | 25.38 | 31.38 | 5.50 | 1.24 | 0.30 |
| 8 | 7.56 | 11.01 | 46.10 | 0.43 | 19.10 | 15.80 | 57.10 | 4.19 | 3.62 | 0.78 |
| 9 | 5.81 | 10.72 | 39.57 | 0.52 | 22.86 | 20.52 | 50.29 | 3.69 | 2.45 | 1.19 |
| 10 | 7.27 | 10.46 | 36.51 | 0.52 | 23.82 | 21.42 | 46.97 | 3.49 | 2.19 | 1.26 |
| 11 | 5.76 | 10.10 | 37.94 | 0.42 | 24.23 | 21.55 | 48.04 | 3.76 | 2.23 | 1.26 |
| 12 | 5.02 | 10.03 | 34.54 | 0.56 | 26.28 | 23.57 | 44.57 | 3.44 | 1.89 | 1.11 |
| 13 | 4.14 | 9.33 | 30.30 | 0.68 | 28.43 | 27.12 | 39.63 | 3.25 | 1.46 | 1.10 |

EXAMPLE 6

This example illustrates the high selectivity to the methylchlorohydrosilanes (MeSiH) resulting from the use of silicon containing about 60 ppm chromium distributed throughout all the particles in the activated silicon.

Runs 6A and 6B

Two experiments are summarized in this example. Both were performed in Reactor B. Silicon sample Si-1, containing a bulk chromium concentration of 60 ppm, was employed in the experiment of Run 6A and Si-4 containing 7.9 ppm chromium, was used in Run 6B. Cuprous chloride catalyst C-6 was used in both cases. The quantities of reagents employed and other experimental conditions pertinent to the experiments of Runs 6A and 6B are given in Table 18. The silicon activation procedure and the conduct of the experiments in Runs 6A and 6B were the same as those previously described in Runs 4A and 3C, respectively.

Table 18 also sets forth the average hourly composition and selectivity of the hourly samples collected during the two experiments. The data show that the silicon sample with 60 ppm Cr (Run 6A) afforded 72.65 wt % methylchlorohydrosilanes (MeSiH) while the one with 7.9 ppm Cr (Run 6B) gave 54.80 wt % (MeSiH) under the same reaction conditions. The ratio, MeSiH/D, was 4.5-5.0 for the former sample and 1.7-2.0 for the latter. However, the silicon sample with lower chromium content was more selective to dimethylchlorosilane, $(CH_3)_2SiHCl$. This was reflected in the lower MD/DM values for Run 6B (Table 18).

In general, selectivities to the methylchlorohydrosilanes of at least sixty weight percent were realized with silicon samples containing 30–1500 ppm Cr when the reaction was performed with 50/50 vol. % hydrogen-methyl chloride.

EXAMPLE 7

This example shows that, like zinc, antimony also inhibits selective synthesis of the methylchlorohydrosilanes (MeSiH).

Reactor A was charged with 290 g, Si-5, and heated to 325° C. with a fluidizing flow (1 lit/min) of nitrogen. HCl flow at the same rate was then substituted for nitrogen and maintained for 30 minutes. The temperature increased to 333° C. A mixture of 12 g copper catalyst, C-1, and 10 g silicon, Si-5, was added through the reservoir. HCl flow as continued for a further 15 minutes. Nitrogen (600 ml/min) was substituted for the nitrogen and the synthesis of methylchlorohydrosilanes (MeSiH) commenced. A total of 72,3 g chlorsilanes was collected from the HCl activation step.

During the synthesis of the methylchlorohydrosilanes, (MeSiH) 0.5 g catalyst, C-1, plus 0.5 g, silicon, Si-5, was added to the reacting mass every two hours through the reservoir. After the seventh hour the additive was changed to 0.1 g $SbCl_3$ plus 0.5 g silicon, Si-5, and the reaction was continued for two more hours. The reaction temperature was 330°±2° C. during the experiment.

Table 19 sets forth the composition and reaction parameters for the nine hourly samples collected. Addition of $SbCl_3$, (equivalent to 370 ppm $SbCl_3$ and 197.5 ppm Sb based on the silicon in the reactor) effectively destroyed the selectivity to the methylchlorohydrosilanes (MeSiH) and reduced the reaction rate. The formation of dimethyldichlorosilane, methyltrichlorosilane and methylchlorodisilanes was enhanced.

The level of antimony employed is within the range taught in the prior art (e.g. U.S. Pat. No. 4,656,301) for promoting dimethyldichlorosilane formation. Along with the prior experiments conducted in the absence of added antimony metal or compounds, this example shows that the antimony concentration in the activated

TABLE 18

Reaction Conditions and Reaction Performance in Runs 6A-6B

| Run | Si | Catalyst | Temp. °C. | Press. psig | $H_2$ lit/min | $CH_3Cl$ lit/min | DM Wt. % | MD Wt. % | D Wt. % | MeSiH Wt. % | MD/DM |
|---|---|---|---|---|---|---|---|---|---|---|---|
| 6A | 900 gm Si-1 | 45.1 gm C-7 | 310 | 30 | 1.25 | 12.66 ± 1.10 | 59.99 ± 0.84 | 15.85 ± 0.10 | 72.65 ± 1.90 | 4.58 ± 0.05 | 4.74 ± 0.52 |
| 6B | 900 gm Si-4 | 45 gm C-7 | 312 ± 2 | 30 | 2.17 | 16.84 ± 0.82 | 37.96 ± 0.80 | 29.81 ± 1.40 | 54.80 ± 1.25 | 1.84 ± 0.13 | 2.26 ± 0.12 | silicon must be maintained below 20 ppm in order that high selectivity to the methylchlorohydrosilanes (MeSiH) and high reaction rate can be realized simultaneously.

TABLE 19

Composition of Hourly Samples Collected in Example 7

| Time | TC | DM | MD | M | T | D | MeSiH | Rate, |

TABLE 19-continued

| (hr) | Wt. % | Wt. % | Wt. % | Wt. % | Wt. % | Wt. % | Wt. % | MD/DM | MeSiH/D | % Si/hr |
|---|---|---|---|---|---|---|---|---|---|---|
| 1 | 27.39 | 9.44 | 44.33 | 1.87 | 2.19 | 14.78 | 53.77 | 4.70 | 3.63 | 0.68 |
| 2 | 0.98 | 18.77 | 4033 | 4.03 | 3.93 | 31.94 | 59.10 | 2.15 | 1.85 | 0.39 |
| 3[a] | 0.29 | 16.37 | 35.15 | 4.04 | 8.03 | 36.06 | 51.52 | 2.15 | 1.43 | 0.92 |
| 4 | — | 16.84 | 30.16 | 5.58 | 7.46 | 39.93 | 47.00 | 1.79 | 1.18 | 0.68 |
| 5[a] | — | 15.34 | 27.04 | 4.90 | 8.50 | 44.23 | 42.38 | 1.76 | 0.96 | 1.12 |
| 6 | — | 13.69 | 22.03 | 5.85 | 8.97 | 49.36 | 35.72 | 1.61 | 0.72 | 0.90 |
| 7 | — | 15.14 | 24.32 | 4.89 | 9.27 | 46.28 | 39.46 | 1.61 | 0.85 | 1.14 |
| 8[b] | — | 5.82 | 10.77 | 5.05 | 16.18 | 61.45 | 16.59 | 1.85 | 0.27 | 0.36 |
| 9[b] | — | 1.75 | 7.19 | 4.39 | 14.74 | 68.43 | 8.94 | 4.11 | 0.13 | 0.30 |

[a]0.5 g C-1 plus 0.5 g Si-5 added at the beginning of the period.
[b]Methylchlorodisilanes were formed following SbCl$_3$ addition, viz: 0.75 wt % in #8 and 3.50 wt % in #9.

EXAMPLE 8

This example shows that the content of dimethylchlorohydrosilane, $(CH_3)_2SiHCl$, in the Direct Synthesis product can be increased relative to that of methyldichlorohydrosilane, $CH_3SiHCl_2$, by the addition of high purity CaSi$_2$ to the activated silicon.

Two experiments are summarized in this example. Both were performed in Reactor A with 300 g silicone, Si-1, and 25 g catalyst, C-2, using the HCl activation procedure described in Example 1A. In each case, reaction was conducted at 329°±2° C. with a mixture of CH$_3$Cl (528 ml/min) and H$_2$ (548 ml/min) for five hours prior to the addition of calcium silicide.

Run 8A CaSi$_2$ (Cerac, Inc.) of certified purity 99.5% was analyzed by x-ray diffraction and volumetric analysis and found to be 99±1 wt. % pure. The sample also contained 0.1 wt. % Al and 0.08 wt. % Fe. 20 g of this powder (−200 mesh particle size) was mixed with 10 g catalyst, C-2, and added to the reactor at the beginning of the sixth hour. The CaSi$_2$ added amounted to 7.5 wt. % of the silicon in the reactor. Reaction was continued another three hours with the 50.9 vol. % H$_2$—CH$_2$Cl mixture. The analysis of the cumulative sample is shown in Table 19.

Run 8B CaSi$_2$ (commercial grade from Elkem Metals Co.) was analyzed by x-ray diffraction and volumetric analysis to be 68±4 wt. %. The sample also contained 1.9 wt. % Al and 2.0 wt. % Fe. 20 g of the powder plus 13 g catalyst, C-2, was added to the reactor at the beginning of the sixth hour of the experiment. The CaSi$_2$ added amounted to 8.05 wt. % of the silicon in the reactor at that time. Reaction was continued with the 50.9 vol. % H$_2$—CH$_3$Cl mixture for five hours. Table 19 sets forth the analysis of the cumulative sample collected.

Table 19 also shows the average composition of the ten hourly control samples collected in the experiments of Runs 8A and 8B prior to the addition of calcium silicide. The data show that 7-8 hr. % high purity CaSi$_2$ afforded 20.1 wt. % $(CH_3)_2SiHCl$, i.e., ~40% increase over the control. In contrast, the lower purity CaSi$_2$ gave 9.55 wt. % $(CH_3)_2SiHCl$, approximately a 48% decrease relative to the control. Additionally, the formation of $(CH_3)_2SiHCl$ relative to $CH_3SiHCl_2$ is increased and the ratio MD/DM decreased compared to the control. This example also shows that additives to the reaction should preferably be substantially free of elements (e.g., Al, Fe) which reduce selectivity to the methylchlorohydrosilanes.

TABLE 19

Analytical, Selectivity and Rate Data for Runs 8A and 8B

| | TC Wt. % | DM Wt. % | MD Wt. % | M Wt. % | T Wt. % | D Wt. % | MeSiH Wt. % | MD/DM | MeSiH/D | Rate, % Si/hr |
|---|---|---|---|---|---|---|---|---|---|---|
| No CaSi$_2$ | — | 14.15 ± 1.67 | 26.64 ± 4.53 | 4.41 ± 1.51 | 6.22 ± 0.78 | 48.58 ± 3.52 | 40.79 ± 5.24 | 1.90 ± 0.32 | 0.84 ± 0.20 | 0.63 ± 0.10 |
| Run 8A Cerac CaSi$_2$ | — | 20.10 | 24.15 | 3.47 | 10.11 | 42.18 | 44.25 | 1.20 | 1.05 | 0.61 |
| Run 8B Elkem CaSi$_2$ | 0.51 | 9.55 | 43.54 | 2.69 | 7.30 | 36.41 | 53.09 | 4.56 | 1.46 | 0.73 |

EXAMPLE 9

This example illustrates the effect of hydrogen content of the methyl chloride-hydrogen mixture on the selectivity and rate parameters of the Direct Synthesis of methylchlorosilanes at atmospheric pressure.

Runs 9A to 9K

Eleven experiments are summarized in this example. Each was performed in Reactor A using the quantities of silicon and copper catalyst set forth in Table 20. The HCl activation procedure of Run 1A was employed. Table 20 also presents the flow rates of methyl chloride and hydrogen and the reaction performance data. The average reaction temperature during the experiments (7-8 hr) was 328°±3° C.

Runs 9A thru 9H were conducted with activated silicon containing <23 ppm tin, <2 ppm zinc, and 50 ppm nickel. The increase in hydrogen content brought about an increase in the selectivity to methylchlorohydrosilanes (MeSiH). In fact, the plot of wt. % MeSiH vs. vol. % H$_2$ was sigmoidal, the region of rapid MeSiH increase being 40–60 vol. % H$_2$. It follows that reactions conducted under these conditions are likely to show unstable reaction performance because a small change in hydrogen content can result in a large change in product composition. Hydrogen contents greater than 60 vol. % gave more stable selectivity values, but the relative molar conversion of hydrogen decreased with increasing hydrogen flow. Additionally, a sharp decrease in reaction rate occurred above 50 vol. % H$_2$. At approximately 50 vol. % H$_2$ (Runs 9C and 9D) the conversion of methyl chloride was about 11 mole percent and the conversion of hydrogen was about 2 mole percent.

The activated silicon in Runs 9I thru 9K each contained 18 ppm Ni, 15 ppm Sn, and 15 ppm Zn. Table 20 shows that hydrogen content had essentially no effect on the rate of the Direct Synthesis with this activated mass and that no change in methylchlorohydrosilanes MeSiH occurred between 48–64 vol. % $H_2$. However, the selectivity to methylchlorohydrosilanes was lower than in Runs 9A thru 9H. The presence of undesirable levels of tin exerted a major negative effect on the formation of $(CH_3)_2SiHCl$.

dure was that described in Run 2D. Flow rates of methyl chloride and hydrogen are listed in Table 21 along with the numerical results of the experiments. The average reaction temperature in Runs 10A, 10B, and 10C was 325°±3° C. and in Runs 10D, 10E, and 10F 329°±2° C. The pressure was held at 31±1 psig.

The data in Table 21 show that higher reaction rates

TABLE 20

| Example 9 | 9A | 9B | 9C | 9D | 9E | 9F | 9G | 9H | 9I | 9J | 9K |
|---|---|---|---|---|---|---|---|---|---|---|---|
| Silicon | Si-5 300 g | Si-5 300 g | Si-5 300 g | Si-5 300 g | Si-5 300 g | Si-5 300 g | Si-5 300 g | Si-5 300 g | Si-1 246.9 g | Si-1 246.9 g | Si-1 246.9 g |
| Catalyst | 25 g C-1 | 24 g C-1 | 25 g C-2 | 24 g C-1 | 50 g C-1 | 25 g C-1 | 25 g C-1 | 24 g C-1 | 3.1 g C-4 | 3.1 g C-4 | 3.1 g C-4 |
| $CH_3Cl$, ml/min | 823 | 700 | 528 | 615.8 | 278 | 228 | 228 | 175 | 1013 | 764 | 534 |
| $H_2$ ml/min | 195 | 548 | 548 | 653.5 | 653.5 | 790 | 790 | 790 | 472 | 708 | 944 |
| Vol. % $H_2$ | 19 | 44 | 51 | 52 | 68 | 78 | 78 | 81 | 32 | 48 | 64 |
| DM wt. % | 2.34 ± 0.12 | 9.73 ± 0.96 | 16.02 ± 2.17 | 17.76 ± 1.66 | 22.10 ± 2.22 | 21.23 ± 0.88 | 21.33 ± 1.42 | 22.78 ± 0.67 | 7.44 ± 1.22 | 9.50 ± 1.67 | 10.71 ± 1.66 |
| MD wt. % | 9.75 ± 0.80 | 18.96 ± 2.57 | 28.94 ± 2.60 | 32.48 ± 6.08 | 46.22 ± 6.26 | 46.64 ± 1.51 | 48.28 ± 1.73 | 46.71 ± 1.01 | 21.45 ± 1.79 | 27.54 ± 3.90 | 27.14 ± 1.80 |
| M wt. % | 6.49 ± 0.29 | 6.40 ± 0.23 | 4.93 ± 0.48 | 4.31 ± 0.59 | 1.94 ± 0.30 | 2.85 ± 0.08 | 2.58 ± 0.12 | 3.36 ± 0.20 | 2.87 ± 0.41 | 2.72 ± 0.09 | 2.67 ± 0.22 |
| T wt. % | 13.81 ± 0.79 | 9.06 ± 0.99 | 5.64 ± 0.54 | 6.76 ± 2.02 | 4.25 ± 1.60 | 2.92 ± 0.20 | 3.04 ± 0.39 | 3.45 ± 0.29 | 11.97 ± 1.78 | 10.51 ± 0.55 | 9.29 ± 0.68 |
| D wt. % | 67.62 ± 1.04 | 55.64 ± 2.38 | 44.16 ± 4.01 | 38.66 ± 5.00 | 25.39 ± 6.49 | 26.00 ± 1.92 | 24.62 ± 2.93 | 23.18 ± 1.11 | 55.17 ± 2.52 | 49.33 ± 5.18 | 50.05 ± 3.30 |
| MeSiH wt. % | 12.09 ± 0.85 | 28.69 ± 3.53 | 44.96 ± 4.49 | 50.24 ± 7.11 | 68.32 ± 8.23 | 67.87 ± 2.38 | 69.61 ± 3.13 | 69.49 ± 1.49 | 28.90 ± 1.57 | 37.04 ± 5.56 | 37.84 3.42 |
| MeSiH/D | 0.18 ± 0.02 | 0.52 ± 0.09 | 1.02 ± 0.10 | 1.35 ± 0.42 | 2.86 ± 0.77 | 2.63 ± 0.34 | 2.86 ± 0.46 | 3.01 ± 0.20 | 0.53 ± 0.05 | 0.77 ± 0.21 | 0.76 ± 0.12 |
| MD/DM | 4.17 ± 0.35 | 1.95 ± 0.07 | 1.82 ± 0.17 | 1.83 ± 0.27 | 2.09 ± 0.16 | 2.20 ± 0.03 | 2.27 ± 0.08 | 2.05 ± 0.05 | 2.97 ± 0.70 | 2.92 ± 0.16 | 2.58 ± 0.34 |
| Rate, % Si/hr | 1.08 ± 0.01 | 0.98 ± 0.09 | 0.96 ± 0.06 | 0.99 ± 0.59 | 0.47 ± 0.08 | 0.43 ± 0.06 | 0.48 ± 0.01 | 0.34 ± 0.03 | 1.13 ± 0.46 | 1.26 ± 0.13 | 1.29 ± 0.26 |

EXAMPLE 10

This sample illustrates that the unstable reaction performance in the production of methylchlorohydrosilanes (MeSiH) which may occur when using 40–60 vol. % $H_2$ at atmospheric (0 psig) can be avoided by conducting the reaction at superatmospheric pressure.

Runs 10A to 10F

Six experiments, all of which were performed in Reactor B, are summarized in this example. The experiments were run with activated silicon containing <2 ppm tin, <15 ppm Zn, and at least 80 ppm nickel in a catalytically effective form. The HCl activation procedure was realized at 30 psig than at 0 psig (Runs 9A–9H) and that reproducible results can be obtained with 50–72 vol. % $H_2$ at superatmospheric pressure. The rate decrease with increasing hydrogen content in the gas feed is less drastic at 30–60 psig than at atmospheric pressure. In Run 10B (62 vol. % $H_2$), the methyl chloride conversion was 28 mole % and the hydrogen conversion 2.8 mole %. These values increased at lower hydrogen partial pressure so that at 50 vol. % $H_2$ (Runs 10D), they were 33 mole % and 4.5 mol %, respectively. Consequently, more efficient utilization of silicon, methyl chloride and hydrogen occurs at pressures above 1 atm. absolute (0 psig).

TABLE 21

| | Reaction Conditions and Results for Runs 10A to 10F | | | | | |
|---|---|---|---|---|---|---|
| Run | 10A | 10B | 10C | 10D | 10E | 10F |
| Silicon g | Si-4 815 | Si-4 815 | Si-4 815 | Si-4 900 | Si-4 900 | Si-4 900 |
| Catalyst g | C-1 40.8 | C-1 40.8 | C-1 40.8 | C-6 45.0 | C-6 45.0 | C-6 45.0 |
| $CH_3Cl$, lit/min | 1.40 | 1.08 | 0.81 | 1.40 | 1.08 | 0.81 |
| $H_2$, lit/min | 1.40 | 1.76 | 2.03 | 1.40 | 1.76 | 2.03 |
| Duration, hr. | 7 | 7 | 8 | 13 | 6 | 8 |
| Vol. % $H_2$ | 50 | 62 | 71.5 | 50 | 62 | 71.5 |
| TC wt. % | 2.54 ± 0.36 | 2.63 ± 0.37 | 2.88 ± 0.08 | 2.31 ± 0.47 | 3.18 ± 0.36 | 2.64 ± 0.13 |
| DM wt. % | 16.93 ± 1.33 | 19.34 ± 1.33 | 19.99 ± 0.47 | 13.99 ± 1.25 | 16.89 ± 0.78 | 17.54 ± 0.24 |
| MD wt. % | 32.03 ± 1.72 | 40.20 ± 1.25 | 40.68 ± 0.61 | 30.88 ± 1.41 | 41.38 ± 1.09 | 44.15 ± 0.16 |
| M wt. % | 2.34 ± 0.37 | 3.22 ± 0.56 | 2.44 ± 0.18 | 3.73 ± 0.89 | 2.66 ± 0.13 | 1.95 ± 0.12 |
| T wt. % | 11.43 ± 0.72 | 10.51 ± 0.78 | 11.60 ± 0.33 | 11.05 ± 0.85 | 11.76 ± 0.87 | 10.04 ± 0.13 |
| D wt. % | 34.73 ± 2.78 | 24.10 ± 1.75 | 22.41 ± 0.73 | 38.04 ± 1.39 | 24.13 ± 0.48 | 23.68 ± 0.24 |
| MeSiH wt. % | 48.96 ± 2.82 | 59.54 ± 1.80 | 60.67 ± 0.66 | 44.87 ± 1.47 | 58.27 ± 1.85 | 61.69 ± 0.32 |

TABLE 21-continued

| Run | Reaction Conditions and Results for Runs 10A to 10F | | | | | |
|---|---|---|---|---|---|---|
| | 10A | 10B | 10C | 10D | 10E | 10F |
| MeSiH/D | 1.42 ± 0.20 | 2.48 ± 0.24 | 2.71 ± 0.11 | 1.18 ± 0.07 | 2.42 ± 0.12 | 2.60 ± 0.04 |
| MD/DM | 1.90 ± 0.12 | 2.09 ± 0.16 | 2.04 ± 0.06 | 2.23 ± 0.29 | 2.45 ± 0.05 | 2.54 ± 0.02 |
| Rate, % Si/hr | 2.72 ± 0.10 | 2.14 ± 0.06 | 1.66 ± 0.08 | 2.63 ± 0.34 | 2.18 ± 0.06 | 1.78 ± 0.06 |

EXAMPLE 11

This example illustrates the Direct Synthesis of methychlorohydrosilanes (MeSiH) containing $CH_3SiH_2Cl$ (DH).

Runs 11A to 11G

All seven experiments of this example were conducted in Reactor B using gas flow rates less than that required to fluidize the bed of activated silicon particles. For each experiment (11A thru 11G), the activated mass was prepared in a furnace at 980° C. from the quantities of silicon and copper catalyst shown in Table 22. However, just prior to reaction with methyl chloride and hydrogen, the mass was etched with HCl at 300° C. in Reactor B. The chlorosilanes formed were collected separately from the methylchlorohydrosilane (MeSiH) product and weighed. Table 22 sets forth the flow rates of methyl chloride and hydrogen, the reaction temperature and pressure, the duration and the composition of the reaction product of each experiment.

For comparison, $CH_3SiH_2Cl$ (DH) was prepared by disproportionation of $CH_3SiHCl_2$ (MD) with hexamethylphosphoramide (HMPA) as described by Dunogues, et al. (U.S. Pat. No. 3,445,200 issued May 20, 1969 to Dunogues et al.) and the product characterized by GC, GC/MS, and 29 Si NMR. GC/MS showed a parent peak at m/e 80, base peak at m/e 79 (loss of one H) and the following additional fragments: m/e 78 (loss of two H atoms), m/e 65 (loss of $CH_3$) and m/e 45 (loss of Cl). The 29 Si NMR resonance was observed at −10.80 ppm (relative to tetramethylsilane).

The data in Table 22 show that $CH_3SiH_2Cl$ (DH) was observed in the reaction products obtained at 0–50 psig and 300° C.-350° C. in a fixed bed reactor. In Runs 10A, 10C, 10F, and 10G, the presence of $CH_3SiH_2Cl$ (DH) was established by capillary GC/MS and the observation of an incompletely resolved shoulder on the falling edge of the methyl chloride peak in the packed column GC. There was insufficient resolution of $CH_3SiH_2Cl$ (DH) from $CH_3Cl$ in these examples to permit quantitative analysis by packed column GC. GC/FTIR was also used to show that the component co-eluting with methyl chloride in the packed column GC had SiH vibrations at approximately 2200 $cm^{-1}$, 960 $cm^{-1}$, 910 $cm^{-1}$, 680 $cm^{-1}$, and 510 $cm^{-1}$.

TABLE 22

| Run | Reaction Conditions and Results for Runs 11A to 11G | | | | | | |
|---|---|---|---|---|---|---|---|
| | 11A | 11B | 11C | 11D | 11E | 11F | 11G |
| Silicon, g | Si-1 921.5 | Si-1 783.6 | Si-5 1382 | Si-1 887.3 | Si-5 1425 | Si-5 1425 | Si-5 1425 |
| Catalyst, g | C-1 48.5 | C-1 41.2 | C-1 73 | C-1 46.7 | C-1 75 | C-2 75 | C-2 75 |
| Temp °C. | 311 ± 4 | 307 ± 1 | 307 ± 1 | 306 ± 1 | 329 ± 4 | 335 ± 4 | 346 ± 3 |
| Pressure, psig | 0 | 20 | 30 | 40 | 40 | 50 | 50 |
| $CH_3Cl$, lit/min | 0.42 | 0.42 | 0.73 | 0.59 | 0.71 | 1.00 | 1.00 |
| $H_2$, lit/min | 0.47 | 0.39 | 1.08 | 0.92 | 1.33 | 1.08 | 1.08 |
| Duration, hr. | 8 | 8 | 8 | 8 | 8 | 4 | 4 |
| Vol. % $H_2$ | 51 | 49 | 60 | 61 | 65 | 51 | 51 |
| DH wt. % | * | 5.94 | * | 5.17 | 0.79 | * | * |
| TC wt. % | — | 1.35 | 3.34 | 2.67 | 1.19 | 0.24 | 0.35 |
| DM wt. % | 0.31 | 3.82 | 14.82 | 0.54 | 3.06 | 10.88 | 1.85 |
| MD wt. % | 32.00 | 43.93 | 50.50 | 42.22 | 33.49 | 36.97 | 32.69 |
| M wt. % | 4.01 | 2.19 | 1.59 | 1.26 | 1.39 | 3.29 | 2.97 |
| T wt. % | 6.50 | 8.10 | 12.42 | 11.56 | 15.68 | 9.30 | 10.19 |
| D wt. % | 57.18 | 34.76 | 17.33 | 36.58 | 44.40 | 39.32 | 51.95 |
| MeSiH wt. % | 32.31 | 53.69 | 65.32 | 47.93 | 37.34 | 47.85 | 34.54 |
| MeSiH/D | 0.57 | 1.55 | 3.77 | 1.31 | 0.84 | 1.22 | 0.67 |
| MD/DM | 103 | 11.50 | 3.41 | 78 | 10.74 | 3.40 | 17.67 |
| Rate, % Si/hr | 0.33 | 0.47 | 1.96 | 0.38 | 2.33 | 0.95 | 1.36 |

*DH incompletely resolved from methyl chloride in GC. Pressence shown by capillary GC/MS and GC/FTIR.

EXAMPLE 12

This example illustrates the potentiating effect of the methylchlorosilanes (M, T, D) on the rate of the Direct Synthesis of methylchlorohydrosilanes (MeSiH). The experiment of this example was conducted for a total of 51 hours, over a nine day period, during which quantities of $(CH_3)_2SiCl_2$ (D), $CH_3SiCl_3$ (T), $(CH_3)_3SiCl$ (M) and their mixtures were injected intermittently into the fluidized-bed of activated silicon particles.

A mixture of 250 g silicon, Si-6, and 12.5 g catalyst, C-6, was charged to Reactor A. No additional silicon or catalyst was added to the reactor during the course of the experiment. The mixture was heated under argon (1 lit/min) fluidization to 350° C. Meanwhile, a syringe containing $(CH_3)_2SiCl_2$ (D) and mounted on a syringe pump was attached to the reactor inlet tube using leaktight, stainless steel Luerlok ® fittings. The point of attachment was approximately 4 inches away from the supporting frit at the base of the reactor. This point was also downstream of the methyl chloride and hydrogen inlets to ensure maximum transport of the methylchlorosilane vapor into the fluidized-bed. The reactor inlet tube was electrically heated and fully wrapped with insulation to ensure rapid and complete vaporization of the methylchlorosilane. A thermocouple in the line recorded the temperature of the vapor. When the reactor temperature reached 350° C. and the inlet temperature 110° C., hydrogen (1 lit/min) was substituted for argon and the injection of $(CH_3)_2SiCl_2$ (D) was started. In the ensuing hour, a total of 13.5 gm $(CH_3)_2SiCl_2$ (D) was delivered by the syringe pump. The $(CH_3)_2SiCl_2$ (D) vapor exiting the reactor was condensed with the dry ice/isopropanol refrigerant. However, it was observed visually that some $(CH_3)_2SiCl_2$ (D) escaped from the condenser along with the hydrogen.

Direct synthesis of the methylchlorohydrosilanes (MeSiH) was commenced after the reactor temperature had been reduced to 330° C. and the gas flow changed to 615 ml/min $CH_3Cl$ and 500 ml/min $H_2$ $(CH_3)_2SiCl_2$ (D) condensed during the activation step described above was included in the first hourly sample. Samples were collected hourly (except 23-24 hr) and analyzed by GC following evaporation of excess methyl chloride. The temperature of the bed was maintained at 330° C.-332° C. during the entire experiment.

The quantities of $(CH_3)_2SiCl_2$ (D), $CH_3SiCl_3$ (T), and $(CH_3)_2SiCl$ (M) injected during the experiment and the duration of the additions are listed in Table 23. When mixtures were employed (15-18 hr, 23-24 hr, 29-32 hr, 35 hr, 40 hr, 43 hr) the table also shows the composition of the mixture. For example, during 15-18 hr the mixture injected contained 86.4 wt. % $(CH_3)_2SiCl_2$ (D) and 13.6 wt. % $CH_3SiCl_3$ (T).

Table 23 also sets forth the absolute gravimetric amounts of the constituents of the hourly samples calculated from the quantitative GC analysis. In the table, sample weight refers to the total quantity of methylchlorosilanes (M, T, D), methylchlorohydrosilanes (MeSiH), trichlorosilane (TC) and unevaporated methyl chloride recovered during each sampling period.

Table 24 sets forth the percentage composition and performance parameters of the hourly samples. Product weight is the weight of methylchlorosilanes (M, T, D), methylchlorohydrosilanes (MeSiH) and trichlorosilane (TC) actually made during the Direct Synthesis. It was computed by subtracting the weight of methyl chloride and the weight of each compound injected from the sample weight. In computing the values in Table 24, it was considered that the following relationship applies to each compound in the sample Amount recovered = Amount injected +
Amount formed in reactor −
(Amount adsorbed in bed +
Amount reacted in bed +
Amount lost by evaporation)

Losses by adsorption, reaction, and evaporation occurred even when no injections were made. GC and GC/MS analyses of methylchlorosilanes recovered from injections in separate control experiments showed no detectable evidence of chemical transformation of the injected methylchlorosilane. Accordingly, it was assumed in the calculations that the losses were approximately constant and negligible. The difference between what was recovered and what was added is that which was formed in the Direct Synthesis. When the weight of a specific compound recovered in a sample was less than the quantity injected, the deficit was carried forward and subtracted from subsequent samples until net formation was realized. The blank entries in Table 24 for D, M, and T are for those cases in which deficits existed.

The data presented in Tables 23 and 24 show that during methylchlorosilane addition (5-8 hr, 15-18 hr, 23-24 hr, 30-33 hr, 36 hr, 41 hr, 44 hr) formation of the compound(s) introduced was suppressed and the overall rate of silicon conversion was decreased. There was also an increase in the percentage of methylchlorohydrosilanes (DM, MD, MeSiH) in the product, but the absolute amounts of these compounds formed was diminished. During 30-33 hr, injection of D+T was limited to the first 30 minutes of each hour. In that case, the hourly rate decrease during the addition was not evident and there was net formation of all products. Maximum rate of addition was 0.1-0.15 g per min. during the entire experiment.

Mixtures of D and T (15-18 hr, 23-24 hr, 30-33 hr) or M and T (36 hr, 41 hr, 44 hr) afforded a post-injection rate increase that was 2-5 times the pre-injection value. The high rates (up to 3.07% Si conversion per hr at 35 hr) attained in this experiment at 0 psig by the Direct Synthesis process of this invention for the production of methylchlorohydrosilanes (MeSiH) are unprecedented in the prior art. Table 23 shows that the increased product formation applies not just to the compound(s) previously injected but to all of the methylchlorosilanes and methylchlorohydrosilanes (MeSiH) Note, however, that the percentages of $(CH_3)_2SiHCl$ (DM) and $CH_3SiHCl_2$ (MD) decrease post-addition (Table 24). Accordingly, MeSiH/D can be less than 1.

The data also show that the MD/DM ratio can be controlled by the choice of methylchlorosilane compounds injected into the reactor. The ratio was generally >2 following addition of D or M+T, but <2 following addition of D+T.

TABLE 23

| | | Gravimetric Contents of Additives and Samples in Example 12 | | | | | | | | | |
|---|---|---|---|---|---|---|---|---|---|---|---|
| Time (hr) | Additive | Additive Wt. g | Duration min. | Sample Wt. g | $CH_3Cl$ g | TC g | DM g | MD g | M g | T g | D g |
| 1 | D | 13.5 | 60 | 15.09 | 1.796 | 0.122 | 0.973 | 2.520 | 0.238 | 0.448 | 8.994 |
| 2 | | | | 6.24 | 0.858 | 0.070 | 0.939 | 1.576 | 0.273 | 0.365 | 2.159 |
| 3 | | | | 6.67 | 0.870 | — | 0.929 | 1.930 | 0.311 | 0.412 | 2.218 |
| 4 | | | | 6.66 | 0.511 | 0.039 | 0.905 | 1.626 | 0.390 | 0.525 | 2.665 |
| 5 | D | 7.50 | 60 | 8.26 | 1.324 | — | 0.518 | 1.322 | 0.090 | 0.208 | 4.798 |
| 6 | | 7.58 | 60 | 11.09 | 1.857 | — | 0.670 | 1.553 | 0.145 | 0.260 | 6.607 |
| 7 | | 7.61 | 60 | 10.10 | 0.297 | — | 0.591 | 1.370 | 0.203 | 0.376 | 7.265 |

TABLE 23-continued

Gravimetric Contents of Additives and Samples in Example 12

| Time (hr) | Additive | Additive Wt. g | Duration min. | Sample Wt. g | CH₃Cl g | TC g | DM g | MD g | M g | T g | D g |
|---|---|---|---|---|---|---|---|---|---|---|---|
| 8 | | 7.62 | 60 | 12.58 | 1.478 | — | 0.823 | 1.751 | 0.281 | 0.499 | 7.747 |
| 9 | | | | 8.75 | 1.021 | — | 0.823 | 1.712 | 0.309 | 0.562 | 4.324 |
| 10 | | | | 7.04 | 0.608 | — | 0.815 | 1.689 | 0.327 | 0.601 | 3.000 |
| 11 | | | | 7.81 | 0.865 | — | 0.924 | 1.874 | 0.354 | 0.645 | 3.149 |
| 12 | | | | 4.90 | — | — | 9.346 | 0.723 | 0.267 | 0.542 | 3.022 |
| 13 | | | | 3.47 | 0.739 | — | 0.519 | 0.900 | 0.108 | 0.308 | 0.896 |
| 14 | | | | 4.54 | 0.596 | — | 0.592 | 1.400 | 0.117 | 0.359 | 1.530 |
| 15 | 86.4% D 13.6% T | 8.17 | 60 | 11.68 | 1.405 | — | 0.757 | 1.576 | 0.223 | 1.071 | 6.648 |
| 16 | | 8.02 | 60 | 13.41 | 1.855 | — | 0.945 | 1.781 | 0.304 | 1.193 | 7.331 |
| 17 | | 7.16 | 60 | 12.51 | 1.749 | — | 0.940 | 1.725 | 0.318 | 1.136 | 6.643 |
| 18 | | 7.77 | 60 | 15.33 | 2.396 | 0.120 | 1.099 | 1.222 | 0.414 | 1.473 | 8.606 |
| 19 | | | | 14.10 | 2.139 | — | 1.287 | 2.188 | 0.422 | 1.260 | 6.805 |
| 20 | | | | 18.71 | 1.218 | — | 1.639 | 2.735 | 0.748 | 1.976 | 10.393 |
| 21 | | | | 6.50 | 0.977 | — | 0.814 | 1.398 | 0.231 | 0.621 | 2.458 |
| 22 | | | | 9.86 | 1.030 | — | 1.130 | 1.961 | 0.338 | 0.928 | 3.474 |
| 23–24 | 75.0% D 25.0% T | 16.78 | 120 | 32.12 | 3.777 | — | 2.586 | 4.195 | 0.758 | 4.143 | 16.661 |
| 25 | | | | 14.47 | 1.810 | — | 1.538 | 2.146 | 0.433 | 1.738 | 6.805 |
| 26 | | | | 16.02 | 1.350 | — | 1.892 | 2.884 | 0.540 | 1.874 | 7.480 |
| 27 | | | | 25.23 | 1.491 | — | 2.632 | 3.999 | 0.923 | 3.171 | 13.014 |
| 28 | | | | 6.01 | 0.608 | — | 8.871 | 1.721 | 0.180 | 0.600 | 2.030 |
| 29 | | | | 9.64 | 1.320 | — | 1.149 | 2.146 | 0.246 | 0.854 | 3.925 |
| 30 | 83.2% D 16.8% T | 4.63 | 30 | 12.05 | 1.634 | — | 1.262 | 2.056 | 0.287 | 1.245 | 5.566 |
| 31 | | 1.94 | 30 | 14.24 | 1.972 | — | 1.584 | 2.500 | 0.356 | 1.424 | 6.4 4 |
| 32 | | 0.84 | 30 | 16.54 | 2.316 | — | 1.862 | 2.860 | 0.422 | 1.637 | 7.442 |
| 33 | | 4.62 | 30 | 20.18 | 2.763 | — | 2.177 | 3.370 | 0.462 | 2.331 | 9.077 |
| 34 | | | | 16.17 | 1.413 | — | 2.069 | 3.147 | 0.411 | 1.910 | 7.220 |
| 35 | | | | 27.25 | 1.760 | — | 3.087 | 5.180 | 0.755 | 3.214 | 13.254 |
| 36 | 83.5% M 16.5% T | 3.72 | 60 | 8.72 | 1.315 | — | 0.987 | 2.339 | 1.766 | 0.942 | 1.371 |
| 37 | | | | 11.61 | 1.498 | — | 1.325 | 3.116 | 0.526 | 1.047 | 4.098 |
| 38 | | | | 10.50 | 0.772 | — | 1.392 | 2.762 | 0.207 | 1.107 | 4.260 |
| 39 | | | | 13.10 | 1.652 | — | 1.715 | 3.402 | 0.238 | 1.381 | 4.712 |
| 40 | | | | 10.83 | 1.048 | — | 1.784 | 3.148 | 0.193 | 1.148 | 3.509 |
| 41 | 83.5% M 16.5% T | 4.84 | 60 | 13.05 | 1.650 | — | 1.917 | 3.646 | 1.341 | 1.331 | 3.165 |
| 42 | | | | 15.56 | 2.163 | — | 2.155 | 4.254 | 1.276 | 1.676 | 4.036 |
| 43 | | | | 21.53 | 1.182 | — | 2.513 | 5.604 | 0.883 | 2.973 | 8.375 |
| 44 | 76.2% 23.8% M | 6.37 | 60 | 8.12 | 1.000 | — | 1.047 | 2.990 | 0.592 | 1.773 | 0.718 |
| 45 | | | | 10.44 | 1.265 | — | 1.350 | 3.745 | 0.510 | 1.932 | 1.638 |
| 46 | | | | 10.25 | 1.168 | — | 1.533 | 3.797 | 0.261 | 1.481 | 2.010 |
| 47 | | | | 10.13 | 1.287 | — | 1.616 | 3.829 | 0.179 | 1.235 | 1.984 |
| 48 | | | | 12.19 | 1.716 | — | 1.885 | 4.290 | 0.145 | 1.252 | 2.932 |
| 49 | | | | 11.43 | 1.275 | — | 1.772 | 4.435 | 0.136 | 1.290 | 2.523 |
| 50 | | | | 11.89 | 2.197 | — | 1.877 | 5.378 | 0.105 | 1.124 | 2.109 |
| 51 | | | | 18.87 | 0.909 | — | 2.125 | 7.501 | 0.181 | 2.170 | 5.444 |

TABLE 24

Hourly Product Composition of Example 12

| Time (hr) | Additive | Product Wt. gms | TC Wt. % | DM Wt. % | MD Wt. % | M Wt. % | T Wt. % | D Wt. % | MeSiH Wt. % | MeSiH/D | MD/DM | Rate, % Si/hr |
|---|---|---|---|---|---|---|---|---|---|---|---|---|
| 1 | D | 4.30 | 2.84 | 22.62 | 58.59 | 5.53 | 10.42 | | 81.21 | | 2.59 | 0.43 |
| 2 | | 5.38 | 1.30 | 17.44 | 29.29 | 5.08 | 6.77 | 40.12 | 46.73 | 1.17 | 1.68 | 0.52 |
| 3 | | 5.80 | — | 16.01 | 33.28 | 5.04 | 6.73 | 39.80 | 49.29 | 1.24 | 2.08 | 0.57 |
| 4 | | 6.15 | 0.63 | 14.71 | 26.45 | 6.35 | 8.54 | 43.32 | 41.16 | 0.95 | 1.80 | 0.55 |
| 5 | D | 2.14 | — | 24.23 | 61.83 | 4.21 | 9.73 | | 86.06 | | 2.55 | 0.22 |
| 6 | D | 2.63 | — | 25.50 | 59.09 | 5.52 | 9.89 | | 84.59 | | 2.32 | 0.27 |
| 7 | D | 2.54 | — | 23.27 | 53.94 | 7.99 | 14.80 | | 77.21 | | 2.32 | 0.26 |
| 8 | D | 3.48 | — | 23.64 | 50.30 | 8.07 | 14.34 | 3.65 | 73.94 | 20.26 | 2.13 | 0.36 |
| 9 | | 3.71 | — | 22.18 | 46.15 | 8.33 | 15.15 | 8.19 | 68.33 | 8.34 | 2.08 | 0.38 |
| 10 | | 6.43 | — | 12.66 | 26.26 | 5.08 | 9.35 | 46.66 | 38.92 | 0.83 | 2.07 | 0.62 |
| 11 | | 6.95 | — | 13.30 | 26.98 | 5.09 | 9.29 | 45.34 | 40.28 | 0.89 | 2.03 | 0.68 |
| 12 | | 4.90 | — | 7.06 | 14.75 | 5.44 | 11.07 | 61.68 | 21.81 | 0.35 | 2.09 | 0.47 |
| 13 | | 2.73 | — | 19.00 | 32.95 | 3.95 | 11.29 | 32.81 | 51.95 | 1.58 | 1.73 | 0.28 |
| 14 | | 3.94 | — | 15.01 | 35.50 | 2.96 | 7.75 | 38.78 | 50.51 | 1.30 | 2.37 | 0.40 |
| 15 | 86.4% D 13.6% T | 2.56 | — | 29.62 | 61.66 | 8.72 | | | 91.28 | | 2.08 | 0.28 |
| 16 | 86.4% D 13.6% T | 3.10 | — | 30.51 | 57.51 | 9.82 | 2.16 | | 88.02 | | 1.89 | 0.34 |
| 17 | 86.4% D 13.6% T | 3.60 | — | 26.10 | 47.89 | 8.83 | 4.58 | 12.60 | 73.99 | 5.87 | 1.83 | 0.39 |
| 18 | 86.4% D 13.6% T | 5.15 | 2.33 | 21.34 | 23.73 | 8.04 | 8.14 | 36.43 | 45.07 | 1.24 | 1.11 | 0.53 |

TABLE 24-continued

Hourly Product Composition of Example 12

| Time (hr) | Additive | Product Wt. gm | TC Wt. % | DM Wt. % | MD Wt. % | M Wt. % | T Wt. % | D Wt. % | MeSiH Wt. % | MeSiH/D | MD/DM | Rate, % Si/hr |
|---|---|---|---|---|---|---|---|---|---|---|---|---|
| 19 | | 11.96 | — | 10.76 | 18.30 | 3.52 | 10.54 | 56.89 | 29.06 | 0.51 | 1.70 | 1.18 |
| 20 | | 17.49 | — | 9.37 | 15.64 | 4.28 | 11.30 | 59.42 | 25.01 | 0.42 | 1.67 | 1.74 |
| 21 | | 5.52 | — | 14.75 | 25.32 | 4.18 | 11.24 | 44.50 | 40.07 | 0.90 | 1.72 | 0.58 |
| 22 | | 7.83 | — | 14.43 | 25.04 | 4.32 | 11.85 | 44.36 | 39.47 | 0.89 | 1.74 | 0.82 |
| 23– 24 | 75.0% D 25.0% T | 11.62 | — | 22.15 | 36.11 | 6.52 | | 35.12 | 58.36 | 1.66 | 1.62 | 0.65 |
| 25 | | 12.66 | — | 12.15 | 16.95 | 3.42 | 13.73 | 53.75 | 29.10 | 0.54 | 1.40 | 1.32 |
| 26 | | 14.67 | — | 12.90 | 19.66 | 3.68 | 12.77 | 50.99 | 32.56 | 0.64 | 1.52 | 1.57 |
| 27 | | 23.74 | — | 11.09 | 16.85 | 3.89 | 13.36 | 54.82 | 27.94 | 0.51 | 1.52 | 2.55 |
| 28 | | 5.40 | — | 16.12 | 31.86 | 3.33 | 11.11 | 37.58 | 47.98 | 1.28 | 1.98 | 0.62 |
| 29 | | 8.32 | — | 13.81 | 25.79 | 2.96 | 10.26 | 47.18 | 39.60 | 0.84 | 1.87 | 0.64 |
| 30 | 83.2% D 16.8% T | 5.79 | — | 21.81 | 35.53 | 4.96 | 8.07 | 29.62 | 47.34 | 1.94 | 1.63 | 0.69 |
| 31 | 83.2% D 16.8% T | 10.33 | — | 15.33 | 24.21 | 3.45 | 10.63 | 46.38 | 39.54 | 0.85 | 1.58 | 1.20 |
| 32 | 83.2% D 16.8% T | 13.38 | — | 13.91 | 21.37 | 3.15 | 11.18 | 50.39 | 35.28 | 0.70 | 1.54 | 1.55 |
| 33 | 83.2% D 16.8% T | 12.80 | — | 17.01 | 26.33 | 3.62 | 12.14 | 40.90 | 43.34 | 1.06 | 1.55 | 1.53 |
| 34 | | 14.76 | — | 14.02 | 21.32 | 2.79 | 12.94 | 48.93 | 35.34 | 0.72 | 1.52 | 1.70 |
| 35 | | 25.49 | — | 12.11 | 20.32 | 2.96 | 12.61 | 52.00 | 32.43 | 0.62 | 1.68 | 3.07 |
| 36 | 83.5% M 16.5% T | 5.03 | — | 19.64 | 46.55 | | 6.53 | 27.28 | 66.19 | 2.43 | 2.37 | 0.66 |
| 37 | | 9.59 | — | 13.82 | 32.51 | | 10.92 | 42.75 | 46.33 | 1.03 | 2.35 | 1.22 |
| 38 | | 9.52 | — | 14.62 | 29.01 | | 11.63 | 44.74 | 43.63 | 0.98 | 1.98 | 1.23 |
| 39 | | 11.21 | — | 15.30 | 30.35 | | 12.32 | 42.03 | 45.65 | 1.09 | 1.98 | 1.46 |
| 40 | | 9.59 | — | 18.60 | 32.83 | | 11.97 | 36.59 | 51.43 | 1.41 | 1.77 | 1.29 |
| 41 | 83.5% M 16.5% T | 9.26 | — | 20.70 | 39.37 | | 5.75 | 34.18 | 60.07 | 1.76 | 1.90 | 1.29 |
| 42 | | 12.12 | — | 17.78 | 35.10 | | 13.82 | 33.30 | 52.88 | 1.59 | 1.97 | 1.67 |
| 43 | | 19.47 | — | 12.91 | 28.79 | | 15.27 | 43.03 | 41.70 | 0.97 | 2.23 | 2.66 |
| 44 | 76.2% T 23.8% M | 4.76 | — | 22.02 | 62.88 | | | 15.10 | 84.90 | 5.62 | 2.86 | 0.73 |
| 45 | | 6.73 | — | 20.05 | 55.62 | | | 24.23 | 75.67 | 3.11 | 2.77 | 1.02 |
| 46 | | 7.67 | — | 19.97 | 49.49 | | 4.34 | 26.20 | 69.46 | 2.65 | 2.48 | 1.16 |
| 47 | | 8.69 | — | 18.60 | 44.07 | 0.29 | 14.21 | 22.83 | 62.67 | 2.75 | 2.37 | 1.30 |
| 48 | | 10.47 | — | 17.71 | 40.96 | 1.38 | 11.95 | 27.99 | 58.67 | 2.10 | 2.31 | 1.59 |
| 49 | | 10.16 | — | 17.45 | 43.67 | 1.33 | 12.70 | 24.85 | 61.12 | 2.46 | 2.50 | 1.57 |
| 50 | | 10.59 | — | 17.72 | 50.77 | 0.99 | 10.61 | 19.91 | 68.49 | 3.44 | 2.87 | 1.68 |
| 51 | | 17.96 | — | 11.83 | 41.76 | 1.01 | 15.09 | 30.31 | 53.59 | 1.77 | 3.53 | 2.80 |

EXAMPLE 13

This example illustrates the benefits of injecting (CH₃)₃SiCl (M) and/or CH₃SiCl₃ (T) at rates >0.1 g per min. into the fluidized-bed Direct Synthesis of methylchlorohydrosilanes (MeSiH) of this invention. Silicon conversion rates >1% per hour and MeSiH/D>1 are simultaneously obtained.

Except as noted hereinbelow the two separate runs of this example were conducted in Reactor A in the manner described in Example 12. The range of methylchlorosilane injection rates in Run 13A was 0.2–0.9 g per min. The reaction temperature was 331°±2° C. In Run 13B, the addition rate was approximately 2 gm per min. and the reaction temperature was held at 355°±2° C.

Run 13A: 250 g. silicon, Si-6, and 12.83 g catalyst, C-6, were charged to the reactor and heated to 350° C. under argon (1 lit/min) fluidization. CH₃Cl (615 ml/min) and H₂ (508 ml/min) were then substituted for the argon. Simultaneously, CH₃SiCl₃ (T) was delivered from the syringe pump and vaporized in the reactor inlet line held at 100° C. A total of 15.3 g CH₃SiCl₃ (T) was injected during the next hour at an average rate of 0.26 g per minute. An exotherm up to 370° C. lasting about 30 minutes occurred during the injection. After the first hourly sample was removed from the condenser, the reactor temperature was reduced to 330° C.

This temperature was maintained (within 2° C.) during the remaining 32 hours of the experiment.

Table 25 sets forth the quantities of CH₃SiCl₃ (T) and (CH₃)₃SiCl (M) injected at other times during the experiment and the duration of the additions. The absolute weights of each compound present in the samples are also recorded in Table 25. Percentage composition and performance parameters for the hourly product mixtures are summarized in Table 26.

Run 13B: 250 g silicon, Si-6, and 12.8 g catalyst, C-6, were heated to 350° in Reactor A with argon as described above in Example 12. The bed was kept fluidized at 350° C. for 48 hr. prior to the start of the reaction. CH₃Cl (615 ml/min), H₂ (508 ml/min) and CH₃SiCl₃ (T) injection were all started simultaneously. 19.90 g CH₃SiCl₃ (T) were pumped into the heated reactor inlet (128° C.) during the 10 minute injection period. The absence of visible liquid in the inlet line during and immediately after the injection attested to the rapid vaporization and transport of the CH₃SiCl₃ (T) The reactor temperature was initially 353° C. No exotherm was observed in this experiment.

A second pulse of CH₃SiCl₃ (T), 20.21 g for 10 minutes, was applied during the second hour. Tables 27 and 28 set forth the data for the ten hours of this experiment.

The data of Tables 25–28 show that Direct Synthesis rates of >1% Si conversion per hour and advantageous selectivities (MeSiH>50 wt %, MeSiH/D>1) were realized when injections of methylchlorosilanes were completed within 30 minutes, and preferably within 20 minutes. Taken together with the results of Example 12, these data also show that it is beneficial to the overall reaction performance to use $(CH_3)_3SiCl$ (M) and/or $CH_3SiCl_3$ (T) as the additives. In mixtures, the $(CH_3)_3SiCl$ (M) content may be as low as 0.001 wt %, but it is preferably 10–30 wt %. Moreover, whenever $CH_3SiCl_3$ (T) is employed, it is advantageous to the formation of higher value products to repeat the addition at frequent intervals (1–10 hours in laboratory work) in order to suppress the formation of $CH_3SiCl_3$ (T), an economically less valuable product, to below 10 wt %.

The rates of methylchlorosilane addition employed in this example ranged from 0.25 g per minute to 2.02 g per minute. Higher rates are desirable for commercial scale operations. In fact, addition rates corresponding to gas flows up to that which completely elutriates all of the silicon from the reactor are beneficial. However, it is preferable to employ addition rates considerably less than these. Based on the flow rate of methyl chloride and the weight of silicon used in the experiments of this example, it can be calculated that during the injection period the quantity of methylchlorosilane(s) (M,T,D) added should be 0.2–2.0 times the weight of methyl chloride or 0.001–0.1 times the weight of silicon in the reactor.

TABLE 25

Gravimetric Contents of Additives and Samples in Run 13A

| Time (hr) | Additive | Additive Wt. g | Duration min. | Sample Wt. g | $CH_3Cl$ g | TC g | DM g | MD g | M g | T g | D g |
|---|---|---|---|---|---|---|---|---|---|---|---|
| 1 | T | 15.3 | 60 | 25.71 | 3.186 | — | 2.039 | 5.137 | 0.591 | 10.551 | 4.206 |
| 2 | | | | 9.13 | 1.173 | — | 0.801 | 2.320 | 0.255 | 2.126 | 2.455 |
| 3 | | | | 3.29 | 0.457 | 0.014 | 0.288 | 1.256 | 0.084 | 0.271 | 0.920 |
| 4 | | | | 3.39 | 0.589 | — | 0.296 | 1.165 | 0.082 | 0.247 | 1.011 |
| 5 | | | | 4.61 | 0.612 | — | 0.420 | 1.376 | 0.136 | 0.282 | 1.784 |
| 6 | T | 7.46 | 30 | 11.56 | 0.191 | — | 0.611 | 1.670 | 0.270 | 5.759 | 2.059 |
| 7 | | | | 8.91 | 0.687 | — | 0.710 | 2.045 | 0.368 | 1.019 | 4.081 |
| 8 | | | | 1.63 | 0.100 | — | 0.173 | 0.472 | 0.050 | 0.165 | 0.671 |
| 9 | T | 7.60 | 30 | 8.92 | 0.940 | — | 0.599 | 1.323 | 0.094 | 4.409 | 1.555 |
| 10 | | | | 7.72 | 0.931 | — | 1.132 | 2.057 | 0.186 | 0.831 | 2.583 |
| 11 | | | | 11.12 | 1.343 | — | 1.735 | 2.876 | 0.260 | 0.851 | 4.055 |
| 12 | 52.61% T. 47.39% T. | 5.17 | 21 | 15.90 | 1.918 | — | 1.868 | 3.196 | 1.773 | 2.323 | 4.822 |
| 13 | | 4.83 | 18 | 16.23 | 1.833 | — | 2.011 | 3.387 | 1.712 | 2.355 | 4.932 |
| 14 | | 5.04 | 16 | 19.09 | 2.212 | — | 2.463 | 4.435 | 1.842 | 2.591 | 5.547 |
| 15 | | 5.15 | 14 | 24.31 | 2.232 | — | 3.170 | 5.781 | 2.074 | 3.544 | 7.509 |
| 16 | M | 4.34 | 14 | 5.81 | 0.561 | 0.034 | 0.494 | 1.097 | 2.129 | 0.451 | 1.044 |
| 17 | | | | 8.78 | 0.750 | — | 1.449 | 2.549 | 0.355 | 0.930 | 2.748 |
| 18 | | | | 13.11 | 1.437 | — | 2.239 | 4.394 | 0.306 | 1.150 | 3.884 |
| 19 | | | | 14.72 | 1.615 | — | 2.703 | 4.949 | 0.274 | 1.526 | 3.653 |
| 20 | | | | 18.43 | 1.749 | — | 2.828 | 5.658 | 0.256 | 1.732 | 6.207 |
| 21 | | | | 20.30 | 1.886 | — | 3.043 | 8.388 | 0.229 | 1.870 | 4.884 |
| 22 | | | | 19.36 | 1.829 | — | 2.883 | 6.393 | 0.211 | 1.990 | 6.054 |
| 23 | | | | 34.23 | 0.969 | 0.257 | 3.666 | 9.608 | 0.599 | 6.819 | 12.312 |
| 24 | M | 11.85 | 14 | 21.74 | 3.200 | — | 1.120 | 3.035 | 8.070 | 4.259 | 2.056 |
| 25 | | | | 13.10 | 1.561 | — | 2.231 | 3.828 | 0.529 | 1.499 | 3.452 |
| 26 | | | | 18.05 | 2.520 | — | 3.005 | 5.115 | 0.316 | 1.942 | 5.152 |
| 27 | | | | 21.05 | 2.747 | — | 3.324 | 5.772 | 0.358 | 2.551 | 6.298 |
| 28 | | | | 20.77 | 2.316 | — | 2.951 | 5.346 | 0.289 | 2.414 | 7.454 |
| 29 | | | | 20.17 | 2.199 | — | 3.041 | 5.577 | 0.309 | 2.707 | 6.337 |
| 30 | | | | 20.99 | 2.506 | — | 2.800 | 5.472 | 0.254 | 2.517 | 7.441 |
| 31 | | | | 20.83 | 2.568 | — | 2.954 | 5.993 | 0.265 | 2.891 | 6.159 |
| 32 | | | | 19.95 | 2.541 | — | 2.576 | 5.766 | 0.206 | 2.569 | 6.292 |
| 33 | | | | 22.74 | 2.496 | — | 2.952 | 7.093 | 0.246 | 3.490 | 6.463 |

TABLE 26

Hourly Product Composition in Run 13A

| Time (hr) | Additive | Product Wt. gms | TC Wt. % | DM Wt. % | MD Wt. % | M Wt. % | T Wt. % | D Wt. % | MeSiH Wt. % | MeSiH/D | MD/DM | Rate, % Si/hr |
|---|---|---|---|---|---|---|---|---|---|---|---|---|
| 1 | T | 11.97 | — | 17.03 | 42.90 | 4.94 | | 35.13 | 59.93 | 1.71 | 2.52 | 1.17 |
| 2 | | 5.83 | — | 13.74 | 39.79 | 4.37 | | 42.10 | 53.53 | 1.27 | 2.90 | 0.57 |
| 3 | | 2.56 | 0.55 | 11.24 | 49.02 | 3.28 | | 35.91 | 60.26 | 1.68 | 4.36 | 0.25 |
| 4 | | 2.55 | — | 11.59 | 45.61 | 3.21 | | 39.59 | 57.20 | 1.44 | 3.94 | 0.25 |
| 5 | | 3.72 | — | 11.30 | 37.03 | 3.66 | | 48.01 | 48.33 | 1.01 | 3.28 | 0.36 |
| 6 | T | 4.61 | — | 13.25 | 36.23 | 5.86 | | 44.66 | 49.48 | 1.11 | 2.73 | 0.45 |
| 7 | | 7.20 | — | 9.86 | 28.39 | 5.10 | | 56.65 | 38.25 | 0.68 | 2.88 | 0.70 |
| 8 | | 1.53 | — | 11.31 | 30.84 | 3.26 | 10.76 | 43.83 | 42.15 | 0.96 | 2.73 | 0.15 |
| 9 | | 3.57 | — | 16.77 | 37.05 | 2.63 | | 43.55 | 53.82 | 1.24 | 2.21 | 0.36 |
| 10 | | 5.96 | — | 19.00 | 34.53 | 3.12 | | 43.35 | 53.53 | 1.23 | 1.82 | 0.60 |
| 11 | | 8.93 | — | 19.44 | 32.22 | 2.91 | | 45.43 | 51.66 | 1.14 | 1.66 | 0.91 |
| 12 | 52.61% T 47.39% M | 9.89 | — | 18.90 | 32.33 | | | 48.77 | 51.23 | 1.05 | 1.71 | 1.01 |
| 13 | 52.61% T 47.39% M | 10.33 | — | 19.47 | 32.79 | | | 47.74 | 52.26 | 1.10 | 1.58 | 1.07 |
| 14 | 52.61% T 47.39% M | 12.45 | — | 19.79 | 35.64 | | | 44.57 | 55.43 | 1.24 | 1.80 | 1.31 |
| 15 | 52.61% T 47.39% M | 16.65 | — | 19.04 | 34.72 | 1.14 | | 45.10 | 53.76 | 1.19 | 1.82 | 1.76 |

TABLE 26-continued

Hourly Product Composition in Run 13A

| Time (hr) | Additive | Product Wt. gms | TC Wt. % | DM Wt. % | MD Wt. % | M Wt. % | T Wt. % | D Wt. % | MeSiH Wt. % | MeSiH/D | MD/DM | Rate, % Si/hr |
|---|---|---|---|---|---|---|---|---|---|---|---|---|
| 16 | M | 3.12 | 1.09 | 15.83 | 35.16 | | 14.46 | 33.46 | 50.99 | 1.52 | 2.22 | 0.68 |
| 17 | | 7.68 | — | 18.88 | 33.21 | | 12.11 | 35.80 | 52.09 | 1.46 | 1.76 | 0.82 |
| 18 | | 11.37 | — | 19.70 | 38.65 | | 10.12 | 31.53 | 58.35 | 1.85 | 1.96 | 1.23 |
| 19 | | 12.83 | — | 21.07 | 38.57 | | 11.89 | 28.47 | 59.64 | 2.10 | 1.83 | 1.41 |
| 20 | | 16.43 | — | 17.22 | 34.45 | | 10.54 | 37.79 | 51.67 | 1.34 | 2.00 | 1.81 |
| 21 | | 18.19 | — | 16.73 | 46.13 | | 10.28 | 26.86 | 62.86 | 2.34 | 2.76 | 2.06 |
| 22 | | 17.32 | — | 16.65 | 36.91 | | 11.49 | 34.95 | 53.56 | 1.53 | 2.22 | 1.98 |
| 23 | | 32.68 | 0.79 | 11.22 | 29.40 | 0.06 | 20.86 | 37.67 | 40.62 | 1.08 | 2.62 | 3.67 |
| 24 | M | 10.47 | — | 10.70 | 28.99 | | 40.68 | 19.63 | 39.69 | 2.02 | 2.71 | 1.19 |
| 25 | | 11.01 | — | 20.26 | 34.77 | | 13.62 | 31.35 | 55.03 | 1.76 | 1.72 | 1.36 |
| 26 | | 15.21 | — | 19.75 | 33.62 | | 12.77 | 33.86 | 53.37 | 1.58 | 1.70 | 1.90 |
| 27 | | 17.95 | — | 18.52 | 32.17 | | 14.21 | 35.10 | 50.69 | 1.44 | 1.74 | 2.27 |
| 28 | | 18.17 | — | 16.25 | 29.43 | | 13.29 | 41.03 | 45.68 | 1.11 | 1.81 | 2.33 |
| 29 | | 17.66 | — | 17.22 | 31.58 | | 15.32 | 35.88 | 48.80 | 1.36 | 1.83 | 2.32 |
| 30 | | 18.23 | — | 15.36 | 30.02 | | 13.80 | 40.82 | 45.38 | 1.11 | 1.95 | 2.44 |
| 31 | | 18.00 | — | 16.42 | 33.30 | | 16.06 | 34.22 | 49.72 | 1.45 | 2.03 | 2.48 |
| 32 | | 17.21 | — | 14.97 | 33.52 | | 14.93 | 36.58 | 48.49 | 1.33 | 2.24 | 2.42 |
| 33 | | 20.00 | — | 14.76 | 35.47 | | 17.45 | 32.32 | 50.23 | 1.55 | 2.40 | 2.88 |

TABLE 27

Gravimetric Contents of Additives and Samples in Run 13B

| Time (hr) | Additive | Additive Wt. g | Duration min. | Sample Wt. g | CH₃Cl g | DM g | MD g | M g | T g | D g |
|---|---|---|---|---|---|---|---|---|---|---|
| 1 | T | 19.90 | 10 | 28.99 | 3.888 | 1.858 | 3.543 | 0.151 | 16.400 | 3.151 |
| 2 | T | 20.21 | 10 | 42.46 | 5.726 | 3.656 | 6.980 | 0.361 | 20.937 | 4.800 |
| 3 | | | | 27.45 | 3.947 | 4.098 | 9.635 | 0.387 | 2.446 | 6.937 |
| 4 | | | | 28.92 | 4.685 | 4.246 | 8.855 | 0.480 | 2.655 | 7.999 |
| 5 | | | | 29.66 | 4.614 | 4.298 | 9.628 | 0.436 | 2.652 | 8.032 |
| 6 | | | | 30.60 | 3.088 | 4.140 | 10.468 | 0.413 | 2.919 | 9.572 |
| 7 | | | | 29.43 | 3.281 | 2.602 | 7.072 | 0.506 | 3.552 | 12.417 |
| 8 | | | | 29.79 | 3.477 | 3.852 | 10.212 | 0.363 | 2.675 | 9.211 |
| 9 | | | | 30.61 | 3.465 | 3.747 | 11.669 | 0.245 | 2.482 | 9.002 |
| 10 | | | | 33.62 | 3.258 | 4.024 | 11.797 | 0.323 | 3.103 | 11.115 |

TABLE 28

Hourly Product Composition in Run 13B

| Time (hr) | Additive | Product Wt. gms | DM Wt. % | MD Wt. % | M Wt. % | T Wt. % | D Wt. % | MeSiH Wt. % | MeSiH/D | MD/DM | Rate, % Si/hr |
|---|---|---|---|---|---|---|---|---|---|---|---|
| 1 | T | 8.70 | 21.35 | 40.71 | 1.74 | | 36.20 | 62.06 | 1.71 | 1.91 | 0.93 |
| 2 | T | 15.80 | 23.14 | 44.19 | 2.29 | | 30.38 | 67.33 | 2.22 | 1.91 | 1.72 |
| 3 | | 21.06 | 19.46 | 45.76 | 1.84 | | 32.94 | 65.22 | 1.98 | 2.35 | 2.31 |
| 4 | | 23.91 | 17.76 | 37.04 | 2.01 | 9.74 | 33.45 | 54.80 | 1.64 | 2.09 | 2.61 |
| 5 | | 25.05 | 17.16 | 38.44 | 1.74 | 10.59 | 32.07 | 55.67 | 1.53 | 2.24 | 2.80 |
| 6 | | 27.51 | 15.05 | 38.05 | 1.50 | 10.61 | 34.79 | 53.10 | 0.83 | 2.53 | 3.15 |
| 7 | | 26.15 | 9.95 | 29.45 | 1.94 | 13.58 | 47.48 | 39.40 | 1.53 | 2.96 | 3.03 |
| 8 | | 26.31 | 14.64 | 38.81 | 1.38 | 10.17 | 35.00 | 53.45 | 1.71 | 2.65 | 3.20 |
| 9 | | 27.15 | 13.80 | 42.99 | 0.90 | 9.14 | 33.16 | 56.79 | 1.42 | 3.12 | 3.42 |
| 10 | | 30.37 | 13.25 | 38.85 | 1.06 | 10.22 | 36.62 | 52.10 | 2.85 | 2.93 | 3.93 |

EXAMPLE 14

This example illustrates that the potent action of the methylchlorosilane auxiliary agents is realized with methyl chloride-hydrogen mixtures and not with methyl chloride alone.

The experiment of this example was conducted with 250 g silicon, Si-6, and 13.5 g catalyst, C-6, in a manner similar to that described in Example 12. During the first nineteen hours, the Direct Synthesis was run with methyl chloride (1 lit/min) and intermittent injections of $(CH_3)_3SiCl$ (M) (1,8, 10 hrs.) and $(CH_3)_2SiCl_2$ (D) (16 hr.). $H_2$(508 ml/min) and $CH_3Cl$ (615 ml/min) were used during the next twenty-six hours along with injections of $(CH_3)_2SiCl_2$ (D) (21, 26 hrs.) and $CH_3SiCl_3$ (T) (36, 43 hrs.). The final four hours were again done with methyl chloride (1 lit/min) alone. The quantities of the methylchlorosilanes injected and the duration of the injections are set forth in Table 29.

Table 29-30 show that with methyl chloride alone (1–19 hrs.) the Direct Synthesis of methylchlorosilanes and methylchlorohydrosilanes (MeSiH) proceeded very poorly (rates <0.5% per hr.) despite the addition of $(CH_3)_3SiCl$ (M) and $(CH_3)_2SiCl_2$ (D) to the reactor at pulse rates of 1–1.5 g/min. Introduction of 45 vol. % $H_2$-55 vol. % $CH_3Cl$ and the injection of $(CH_3)_2SiCl_2$ (D) (1.44 g/min) at the twentieth hour resulted in increased formation of all products. This improved performance was sustained with further additions of $(CH_3)_2SiCl_2$ (D) (25 hr.) and of $CH_3SiCl_3$ (33,41 hrs.) and as long as the mixture of methyl chloride and hydrogen was the reactant (up to 45 hr.). Reintroduction of methyl chloride alone (46–49 hr.) at 1.0 lit/min caused a return to the low rates observed during the first nineteen hours.

In this example, the Direct Synthesis with methyl chloride alone was performed without the zinc and tin promoters which favor high selectivities to and high rates of formation of $(CH_3)_2SiCl_2$ (D) It was shown above in Examples 1 and 2 that these promoters disfavor the methylchlorohydrosilanes (MeSiH). The prior art teaches that in the Direct Synthesis with methyl chloride the reaction rate is directly proportional to the partial pressure of methyl chloride (DeCooker, Ph.D Diss. loc. cit. pp. 64–73; Sadowski, et al., *Z. Anorg. Allg. Chem.*, Vol. 443, p. 189 (1978); Gorbunov, et al., *Russ. Chem Rev.*, Vol. 43, p. 291 (1974). The observation of higher reaction rate with lower methyl chloride partial pressure, as illustrated in this Example of the Direct Synthesis of methylchlorohydrosilanes (MeSiH), is unprecedented in the prior art.

TABLE 29

Gravimetric Contents of Additives and Samples of Example 14

| Time (hr) | | Additive | Additive Wt. g | Duration min. | Sample Wt. g | $CH_3Cl$ g | TC g | DM g | MD g | M g | T g | D g |
|---|---|---|---|---|---|---|---|---|---|---|---|---|
| $CH_3Cl$ | 1 | M | 15.50 | 15.0 | 21.17 | 3.116 | 0.239 | 0.140 | 1.996 | 13.123 | 0.734 | 1.823 |
| | 2 | | | | 6.01 | 0.902 | — | 0.101 | 0.193 | 1.749 | 0.471 | 2.594 |
| | 3 | | | | 5.01 | 0.719 | — | 0.109 | 0.206 | 0.268 | 0.605 | 3.103 |
| | 4 | | | | 3.61 | 0.525 | — | 0.093 | 0.180 | 0.198 | 0.574 | 2.040 |
| | 5 | | | | 2.48 | 0.339 | — | 0.092 | 0.238 | 0.112 | 0.425 | 1.274 |
| | 6 | | | | 1.68 | 0.077 | — | 0.053 | 0.222 | 0.050 | 0.380 | 0.898 |
| | 7 | | | | 0.30 | 0.024 | — | 0.008 | 0.038 | 0.008 | 0.074 | 0.148 |
| | 8 | M | 8.79 | 7.5 | 12.71 | 2.216 | — | 0.160 | 0.445 | 8.746 | 0.365 | 0.778 |
| | 9 | | | | 1.16 | 0.173 | — | 0.039 | 0.169 | 0.043 | 0.224 | 0.512 |
| | 10 | M | 8.69 | 6.0 | 9.55 | 0.684 | — | 0.091 | 0.286 | 7.670 | 0.310 | 0.509 |
| | 11 | | | | 1.15 | 0.154 | — | 0.034 | 0.254 | 0.066 | 0.212 | 0.430 |
| | 12 | | | | 3.73 | 0.169 | — | 0.176 | 0.419 | 0.254 | 0.649 | 2.063 |
| | 13 | | | | 0.87 | 0.063 | — | 0.028 | 0.064 | 0.029 | 0.166 | 0.519 |
| | 14 | | | | 1.62 | 0.092 | — | 0.039 | 0.110 | 0.050 | 0.346 | 0.983 |
| | 15 | D | 19.14 | 14 | 19.68 | 3.214 | — | 0.077 | 0.303 | 0.256 | 0.496 | 15.334 |
| | 16 | | | | 4.49 | 0.226 | — | 0.151 | 0.184 | 0.214 | 0.885 | 2.830 |
| | 17 | | | | 3.16 | 0.118 | — | 0.130 | 0.142 | 0.150 | 0.795 | 1.825 |
| | 18 | | | | 2.24 | 0.212 | — | 0.098 | 0.128 | 0.080 | 0.618 | 1.104 |
| | 19 | | | | 2.07 | 0.339 | — | 0.081 | 0.110 | 0.063 | 0.418 | 1.059 |
| $CH_3Cl +$ | 20 | D | 17.31 | 12 | 23.09 | 2.879 | — | 1.510 | 3.960 | 0.118 | 0.605 | 14.018 |
| $H_2$ | 21 | | | | 7.13 | 0.478 | — | 1.386 | 3.183 | 0.109 | 0.533 | 1.441 |
| | 22 | | | | 8.63 | 0.922 | — | 1.639 | 3.345 | 0.180 | 0.617 | 2.030 |
| | 23 | | | | 8.30 | 0.996 | — | 1.550 | 2.933 | 0.180 | 0.611 | 2.030 |
| | 24 | | | | 13.85 | 0.079 | 0.073 | 1.593 | 3.272 | 0.368 | 4.295 | 4.170 |
| | 25 | D | 7.42 | 5 | 24.03 | — | 0.125 | 2.787 | 5.746 | 0.651 | 7.305 | 7.416 |
| | 26 | | | | 1.25 | 0.118 | — | 0.219 | 0.299 | 0.026 | 0.170 | 0.419 |
| | 27 | | | | 2.77 | 0.067 | — | 0.401 | 1.213 | 0.054 | 0.275 | 0.760 |
| | 28 | | | | 2.38 | 0.120 | — | 0.379 | 1.101 | 0.041 | 0.195 | 0.544 |
| | 29 | | | | 6.15 | 0.734 | — | 1.080 | 2.181 | 0.123 | 0.475 | 1.557 |
| | 30 | | | | 6.97 | 0.671 | — | 1.220 | 2.897 | 0.123 | 0.528 | 1.531 |
| | 31 | | | | 7.86 | 1.011 | — | 1.382 | 2.613 | 0.163 | 0.652 | 2.039 |
| | 32 | | | | 8.73 | 0.544 | — | 1.495 | 2.842 | 0.203 | 0.877 | 2.769 |
| | 33 | T | 22.02 | 11.5 | 15.17 | 1.846 | — | 0.772 | 1.748 | 0.065 | 9.469 | 1.270 |
| | 34 | | | | 10.98 | 1.519 | — | 1.780 | 2.947 | 0.209 | 1.207 | 3.318 |
| | 35 | | | | 14.86 | 1.791 | — | 2.447 | 3.965 | 0.291 | 1.675 | 4.691 |
| | 36 | | | | 16.88 | 2.184 | — | 2.723 | 4.453 | 0.333 | 1.826 | 5.361 |
| | 37 | | | | 17.32 | 2.094 | — | 2.782 | 4.652 | 0.348 | 2.002 | 5.442 |
| | 38 | | | | 16.99 | 2.046 | — | 2.718 | 4.730 | 0.340 | 1.877 | 5.279 |
| | 39 | | | | 16.63 | 2.017 | — | 2.646 | 4.713 | 0.328 | 1.829 | 5.097 |
| | 40 | | | | 15.44 | 0.954 | — | 2.511 | 4.799 | 0.324 | 1.814 | 5.038 |
| | 41 | T | 19.50 | 10 | 19.31 | 2.352 | — | 1.041 | 3.283 | 0.058 | 10.736 | 1.840 |
| | 42 | | | | 12.49 | 1.478 | — | 1.835 | 3.827 | 0.142 | 1.622 | 3.586 |
| | 43 | | | | 18.20 | 2.226 | — | 2.641 | 5.143 | 0.228 | 2.339 | 5.623 |
| | 44 | | | | 19.28 | 2.574 | — | 2.855 | 5.558 | 0.237 | 2.437 | 5.618 |
| | 45 | | | | 19.66 | 2.178 | — | 2.847 | 5.709 | 0.236 | 2.676 | 6.014 |
| $CH_3Cl$ | 46 | | | | 6.37 | 0.946 | — | 0.490 | 0.997 | 0.129 | 0.987 | 2.821 |
| | 47 | | | | 1.27 | 0.139 | — | 0.046 | 0.095 | 0.030 | 0.241 | 0.719 |
| | 48 | | | | 0.29 | | | | Samples Not Analyzed | | | |
| | 49 | | | | 0.28 | | | | Samples Not Analyzed | | | |

TABLE 30

Hourly Product Composition in Example 14

| Time (hr) | | Additive | Product Wt. gms | TC Wt. % | DM Wt. % | MD Wt. % | M Wt. % | T Wt. % | D Wt. % | MeSiH Wt. % | MeSiH/D | MD/DM | Rate, % Si/hr |
|---|---|---|---|---|---|---|---|---|---|---|---|---|---|
| $CH_3Cl$ | 1 | M | 4.93 | 4.85 | 2.84 | 40.47 | 14.88 | 36.96 | 43.31 | 1.17 | 14.25 | 0.45 |
| | 2 | | 3.36 | — | 3.01 | 5.75 | | 14.02 | 77.22 | 8.76 | 0.11 | 1.91 | 0.29 |
| | 3 | | 4.02 | — | 2.71 | 5.12 | | 15.04 | 77.13 | 7.83 | 0.10 | 1.89 | 0.35 |
| | 4 | | 2.89 | — | 3.22 | 6.24 | | 19.88 | 70.66 | 9.46 | 0.13 | 1.94 | 0.25 |
| | 5 | | 2.03 | — | 4.53 | 11.73 | | 20.95 | 62.79 | 16.26 | 0.26 | 2.59 | 0.18 |
| | 6 | | 1.55 | — | 3.42 | 14.32 | | 24.52 | 57.74 | 17.74 | 0.31 | 4.19 | 0.14 |
| | 7 | | 0.27 | — | 2.99 | 14.18 | | 27.61 | 55.22 | 17.17 | 0.31 | 4.74 | 0.02 |
| | 8 | M | 1.75 | — | 9.15 | 25.46 | | 20.88 | 44.51 | 34.61 | 0.78 | 2.78 | 0.16 |
| | 9 | | 0.94 | — | 4.13 | 17.90 | | 23.73 | 54.24 | 22.03 | 0.41 | 4.33 | 0.08 |
| | 10 | M | 1.20 | — | 7.61 | 23.91 | | 25.92 | 42.56 | 31.52 | 0.74 | 3.14 | 0.11 |
| | 11 | | 0.93 | — | 3.66 | 27.31 | | 22.80 | 46.23 | 30.97 | 0.67 | 7.46 | 0.08 |
| | 12 | | 3.31 | — | 5.32 | 12.67 | | 19.63 | 62.38 | 17.99 | 0.29 | 2.38 | 0.30 |
| | 13 | | 0.78 | — | 3.58 | 8.25 | | 21.40 | 66.77 | 11.83 | 0.18 | 2.30 | 0.07 |
| | 14 | | 1.48 | — | 2.64 | 7.44 | | 23.41 | 66.51 | 10.08 | 0.15 | 2.82 | 0.13 |

TABLE 30-continued

| | | | | Hourly Product Composition in Example 14 | | | | | | | | |
|---|---|---|---|---|---|---|---|---|---|---|---|---|
| Time (hr) | Additive | Product Wt. gms | TC Wt. % | DM Wt. % | MD Wt. % | M Wt. % | T Wt. % | D Wt. % | MeSiH Wt. % | MeSiH/D | MD/DM | Rate, % Si/hr |
| 15 | D | 1.13 | — | 6.80 | 26.77 | 22.62 | 43.81 | | 33.57 | | 3.94 | 0.11 |
| 16 | | 1.43 | — | 10.53 | 12.83 | 14.92 | 61.72 | | 23.36 | | 1.22 | 0.13 |
| 17 | | 2.07 | — | 6.29 | 6.87 | 7.26 | 38.48 | 41.10 | 13.16 | 0.32 | 1.09 | 0.18 |
| 18 | | 2.03 | — | 4.83 | 6.31 | 3.94 | 30.47 | 54.45 | 11.14 | 0.21 | 1.31 | 0.18 |
| 19 | | 1.73 | — | 4.68 | 6.36 | 3.64 | 24.15 | 61.17 | 11.04 | 0.18 | 1.36 | 0.16 |
| CH$_3$Cl 20 | D | 6.19 | — | 24.38 | 63.94 | 1.91 | 9.77 | | 88.32 | | 2.62 | 0.65 |
| + 21 | | 5.21 | — | 26.60 | 61.08 | 2.09 | 10.23 | | 87.68 | | 2.30 | 0.55 |
| H$_2$ 22 | | 5.86 | — | 27.98 | 57.11 | 3.07 | 10.53 | 1.31 | 85.09 | 64.95 | 2.04 | 0.62 |
| 23 | | 7.30 | — | 21.2 | 40.16 | 2.46 | 8.37 | 27.79 | 61.38 | 2.21 | 1.89 | 0.75 |
| 24 | | 13.77 | 0.53 | 11.57 | 23.76 | 2.67 | 31.19 | 30.28 | 35.33 | 1.17 | 2.05 | 1.31 |
| 25 | D | 16.61 | 0.75 | 16.78 | 34.58 | 3.92 | 43.97 | | 51.36 | | 2.06 | 1.63 |
| 26 | | 1.13 | — | 19.34 | 26.36 | 2.26 | 15.00 | 37.04 | 45.70 | 1.23 | 1.36 | 0.12 |
| 27 | | 2.70 | — | 14.84 | 44.88 | 2.00 | 10.17 | 28.11 | 59.72 | 2.13 | 3.02 | 0.28 |
| 28 | | 2.26 | — | 16.77 | 48.72 | 1.81 | 8.63 | 24.07 | 65.49 | 2.72 | 2.91 | 0.24 |
| 29 | | 5.42 | — | 19.94 | 40.27 | 2.27 | 8.77 | 28.75 | 60.21 | 2.09 | 2.02 | 0.58 |
| 30 | | 6.30 | — | 19.37 | 45.99 | 1.95 | 8.38 | 24.31 | 65.36 | 2.69 | 2.37 | 0.68 |
| 31 | | 6.85 | — | 20.18 | 38.15 | 2.38 | 9.52 | 29.77 | 58.33 | 1.96 | 1.89 | 0.74 |
| 32 | | 8.19 | — | 18.26 | 34.72 | 2.48 | 10.71 | 33.83 | 52.98 | 1.57 | 1.90 | 0.88 |
| 33 | T | 3.86 | — | 20.03 | 45.34 | 1.69 | | 32.94 | 65.37 | 1.99 | 2.26 | 0.43 |
| 34 | | 8.25 | — | 21.57 | 35.70 | 2.53 | | 40.20 | 57.27 | 1.43 | 1.66 | 0.92 |
| 35 | | 11.39 | — | 21.48 | 34.80 | 2.55 | | 41.17 | 56.28 | 1.37 | 1.62 | 1.28 |
| 36 | | 12.87 | — | 21.16 | 34.60 | 2.59 | | 41.65 | 55.76 | 1.34 | 1.64 | 1.46 |
| 37 | | 13.22 | — | 21.04 | 35.18 | 2.63 | | 41.15 | 56.22 | 1.37 | 1.67 | 1.53 |
| 38 | | 13.07 | — | 20.80 | 36.20 | 2.60 | | 40.40 | 57.00 | 1.41 | 1.74 | 1.53 |
| 39 | | 12.78 | — | 20.70 | 36.87 | 2.54 | | 39.87 | 57.57 | 1.44 | 1.78 | 1.52 |
| 40 | | 12.67 | — | 19.82 | 37.87 | 2.56 | | 39.75 | 57.69 | 1.45 | 1.91 | 1.53 |
| 41 | T | 6.22 | — | 16.73 | 52.77 | 0.93 | | 29.57 | 69.50 | 2.35 | 3.15 | 0.77 |
| 42 | | 9.39 | — | 19.54 | 40.76 | 1.51 | | 38.19 | 60.30 | 1.58 | 2.09 | 1.16 |
| 43 | | 13.64 | — | 19.37 | 37.72 | 1.67 | | 41.24 | 57.09 | 1.38 | 1.95 | 1.70 |
| 44 | | 14.27 | — | 20.01 | 38.95 | 1.66 | | 39.38 | 58.96 | 1.50 | 1.95 | 1.82 |
| 45 | | 15.12 | — | 18.83 | 37.77 | 1.56 | 2.06 | 39.78 | 56.60 | 1.42 | 2.01 | 1.94 |
| 46 | | 5.42 | — | 9.03 | 18.38 | 2.38 | 18.20 | 52.01 | 27.41 | 0.53 | 2.04 | 0.66 |
| 47 | | 1.13 | — | 4.04 | 8.40 | 2.67 | 21.32 | 63.57 | 12.44 | 0.20 | 2.08 | 0.13 |
| 48 | | | | Samples Not Analyzed | | | | | | | | 0.03 |
| 49 | | | | Samples Not Analyzed | | | | | | | | 0.03 |

What is claimed is:

1. A Direct Synthesis process for the selective production of organohalohydrosilanes of the general formula:

$$R_aH_bSiX_c \qquad (I)$$

by the reaction of activated silicon with a mixture of an organohalide of the general formula:

$$RX$$

and hydrogen in contact with a catalytic amount of catalyst at elevated temperature, in which:

R is a hydrocarbyl group having up to about 20 carbon atoms;

X is a halogen atom; and a, b and c are integer having a value of 1 or 2 with the proviso that the sum of a plus b plus c is 4 wherein the concentration of the following metal atoms in the activated silicon bed are as follows:

(i) Zn, Sb and Cd, individually or totally, less than 0.05 weight percent of the silicon;

(ii) Sn, less than 0.01 weight percent of the silicon;

(iii) Ni, from about 0.001 to about 0.02 weight percent of the silicon;

(iv) Cr, from about 0.001 to about 0.06 weight percent of the silicon; and (v) Cu, up to about 10 weight percent of the silicon.

2. The Direct Synthesis process as claimed in claim 1, wherein the concentrations of said metal atoms are:

(i) Zn, Sb and Cd, individually or totally, less than 0.01 weight percent;

(ii) Sn, less than 0.005 weight percent;

(iii) Ni, from about 0.002 to about 0.01 weight percent;

(iv) Cr, less than about 0.04 weight percent; and (v) Cu, from about 0.05 to about 3 weight percent.

3. The Direct Synthesis process as claimed in claim 1, wherein the concentrations of said metal atoms are:

(i) Zn, Sb and Cd, individually or totally, less than 0.005 weight percent;

(ii) Sn, less than 0.0005 weight percent;

(iii) Ni, from about 0.004 to about 0.008 weight percent;

(iv) Cr, from about 0.0005 to about 0.01 weight percent; and (v) Cu, from about 0.5 to about 1.5 weight percent.

4. The Direct Synthesis process as claimed in claim 1, wherein R is methyl and X is chlorine.

5. The Direct Synthesis process as claimed in claim 1, wherein said catalyst (v) is a copper, silver, or copper-silver mixture catalyst.

6. The Direct Synthesis process as claimed in claim 1, wherein said organohalohydrosilanes selectively produced are a mixture comprising R$_2$SiHX and RSiHX$_2$, wherein R and X are as defined in claim 1, said organohalide is methylchloride, said catalyst is a copper catalyst and the total concentration of Zn plus Sb plus Cd is less than 0.0008 weight percent, the concentration of Sn is about 0.0003 weight percent, the concentration of Ni is about 0.0018 weight percent, and concentration of Cr is about 0.006 weight percent.

7. The Direct Synthesis process as claimed in claim 1, wherein there is present in said activated silicon bed from about 1 to about 10 weight percent of a silicide of calcium, magnesium or copper.

8. The Direct Synthesis process as claimed in claim 1, wherein said organohalohydrosilanes selectively produced are a mixture comprising $R_2SiHX$ and $RSiHX_2$, wherein R and X are as defined in claim 1, said organohalide is methylchloride, said catalyst is a copper catalyst and wherein there is present in said activated silicon bed from about 2 to about 8 weight percent of calcium silicide.

9. The Direct Synthesis process as claimed in claim 1, wherein the pressure is atmospheric pressure.

10. The Direct Synthesis process as claimed in claim 1, wherein the pressure is superatmospheric pressure.

11. The Direct Synthesis as claimed in claim 6, wherein R is methyl and X is chlorine.

12. The Direct Synthesis process as claimed in claim 1, wherein said organohalohydrosilanes selectively produced are a mixture comprising $R_2SiHX$, $RSiHX_2$ and $RSiH_2X$, wherein R and X are defined in claim 1, said organohalide is methyl chloride, and said catalyst is a copper catalyst.

13. The Direct Synthesis process as claimed in claim 12, wherein there is present in said activated silicon bed from about 2 to about 8 weight percent of calcium silicide.

14. The Direct Synthesis process as claimed in claim 12, wherein R is methyl and X is chlorine.

15. The Direct Synthesis process as claimed in claim 1, wherein an auxiliary agent is introduced into said activated silicon bed from the group of (i) a halosilane of the general formula:

$$H_dSiX_e$$

wherein d has a value of 0 to 3, e has a value of 1 to 4 and the sum of d plus e is 4; or (ii) an organohalosilane of the general formula:

$$R'_fSiX_{4-f}$$

wherein R' is an alkyl group having from 1 to about 6 carbon atoms and f has a value of from 1 to 3; or (iii) an organohalohydrosilane of the general formula:

$$R_aH_bSiX_c \qquad (I)$$

as defined in claim 1.

16. The Direct Synthesis process as claimed in claim 15, wherein said auxiliary agent is introduced during the silicon activation.

17. The Direct Synthesis process as claimed in claim 15, wherein said auxiliary agent is injected into the activated silicon during the course of the Direct Synthesis reaction.

18. The Direct Synthesis process as claimed in claim 1 wherein a promoter is introduced into said activated silicon, said promoter being from the group of the nickel, chromium, rhodium and palladium atoms.

19. The Direct Synthesis process as claimed in claim 18, wherein said promoter is the nickel atom at a concentration of from about 0.002 to about 0.08 weight percent of the activated silicon.

20. The Direct Synthesis process as claimed in claim 18, wherein said promoter is the chromium atom at a concentration up to about 0.005 weight percent of the activated silicon.

21. The Direct Synthesis process as claimed in claim 18, wherein said promoter is the rhodium atom of a concentration up to about 1 weight percent of the activated silicon.

22. The Direct Synthesis process as claimed in claim 18, wherein said promoter is the palladium atom at a concentration up to about 0.5 weight percent of the activated silicon.

23. The Direct Synthesis process as claimed in claim 12, wherein said process is carried out in a fixed-bed reactor.

24. The Direct Synthesis process as claimed in claim 15, wherein the auxiliary agent is dimethyldichlorosilane.

25. The Direct Synthesis process as claimed in claim 15, wherein the auxiliary agent is methyltrichlorosilane.

26. The Direct Synthesis process as claimed in claim 15, wherein the auxiliary agent is trimethylchlorosilane.

27. An activated silicon composition for use in the Direct Synthesis of organohalohydrosilanes of the general formula:

$$R_aH_bSiX_c \qquad (I)$$

by the reaction of activated silicon with a mixture of an organohalide of the general formula:

$$RX$$

and hydrogen comprising silicon and
 (i) Zn, Sb and Cd, individually or totally, less than 0.05 weight percent of the silicon;
 (ii) Sn, less than 0.01 weight percent of the silicon;
 (iii) Ni, from about 0.001 to about 0.02 weight percent of the silicon;
 (iv) Cr, from about 0.001 to about 0.06 weight percent of the silicon; and
 (v) Cu, up to about 10 weight percent of the silicon.

28. An activated silicon composition as claimed in claim 27 comprising silicon and
 (i) Zn, Sb and Cd, individually or totally, less than 0.01 weight percent;
 (ii) Sn, less than 0.005 weight percent;
 (iii) Ni, from about 0.002 to about 0.01 weight percent;
 (iv) Cr, less than about 0.04 weight percent; and
 (v) Cu, from about 0.05 to about 3 weight percent.

29. An activated silicon composition as claimed in claim 27 comprising silicon and
 (i) Zn, Sb and Cd, individually or totally, less than 0.005 weight percent;
 (ii) Sn, less than 0.0005 weight percent;
 (iii) Ni, from about 0.004 to about 0.008 weight percent;
 (iv) Cr, from about 0.0005 to about 0.01 weight percent; and
 (v) Cu, from about 0.5 to about 1.5 weight percent.

30. An activated silicon composition as claimed in claim 27 comprising silicon wherein the total concentration of Zn plus Sb plus Cd is less than 0.0008 weight percent, the concentration of Sn is about 0.0003 weight percent, the concentration of Ni is about 0.0018 weight percent, and concentration of Cr is about 0.006 weight percent.

* * * * *